US006008035A

United States Patent [19]
Johnston et al.

[11] Patent Number: 6,008,035
[45] Date of Patent: Dec. 28, 1999

[54] SYSTEM FOR THE IN VIVO DELIVERY AND EXPRESSION OF HETEROLOGOUS GENES IN THE BONE MARROW

[75] Inventors: Robert E. Johnston; Nancy L. Davis, both of Chapel Hill; Dennis A. Simpson, Pittsboro, all of N.C.

[73] Assignee: The University of North Carolina at Chapel Hill, Chapel Hill, N.C.

[21] Appl. No.: 09/102,248

[22] Filed: Jun. 22, 1998

Related U.S. Application Data

[62] Division of application No. 08/801,263, Feb. 19, 1997, Pat. No. 5,811,407.
[51] Int. Cl.$^6$ .............................. C12N 7/00; C12N 5/10; C12N 7/01; C12N 15/11; C12N 15/40
[52] U.S. Cl. .................................... 435/235.1; 435/320.1; 435/325; 536/23.1; 536/23.72; 424/93.6
[58] Field of Search ............................. 435/235.1, 320.1, 435/325; 424/96.6; 536/23.1, 23.72

[56] References Cited

U.S. PATENT DOCUMENTS

| | | | |
|---|---|---|---|
| 4,650,764 | 3/1987 | Temin et al. | 435/350 |
| 5,091,309 | 2/1992 | Schlesinger et al. | 435/69.1 |
| 5,185,440 | 2/1993 | Davis et al. | 536/23.72 |
| 5,217,879 | 6/1993 | Huang et al. | 435/69.1 |
| 5,505,947 | 4/1996 | Johnston et al. | 424/218.1 |
| 5,639,650 | 6/1997 | Johnston et al. | 435/236 |
| 5,643,576 | 7/1997 | Johnston et al. | 424/199.1 |
| 5,739,026 | 4/1998 | Garoff et al. | 435/352 |
| 5,789,245 | 8/1998 | Dubensky, Jr. et al. | 435/320.1 |
| 5,792,462 | 8/1998 | Johnston et al. | 424/199.1 |
| 5,814,482 | 9/1998 | Dubensky, Jr. et al. | 435/69.3 |
| 5,843,723 | 12/1998 | Dubensky, Jr. et al. | 435/69.3 |

FOREIGN PATENT DOCUMENTS

| | | |
|---|---|---|
| WO92/10578 | 6/1992 | WIPO . |
| WO 95/07994 | 3/1995 | WIPO . |
| WO 95/27044 | 10/1995 | WIPO . |
| WO 95/31565 | 11/1995 | WIPO . |
| WO 96/17072 | 6/1996 | WIPO . |
| WO 96/37220 | 11/1996 | WIPO . |
| WO 96/37616 | 11/1996 | WIPO . |
| WO 97/38087 | 10/1997 | WIPO . |

OTHER PUBLICATIONS

Hahn et al. Infectious Sindbis virus transient expression vectors for studying antigen processing and presentation. Proc. Natl. Acad. Sci. USA vol. 89 pp. 2679–2683, 1992.

Orkin et al. Report and recommendations of the panel to assess the NIH investment in research on gene therapy. pp. 1–41, 1995.

Dubensky, Jr. et al.; Sindbis Virus DNA–Based Expression Vectors: Utility for In Vitro and In Vivo Gene Transfer, Journal of Virology, 70:(508–519) Jan. 1996.

Frolova et al.; Packaging Signals in Alphaviruses, Journal of Virology, 71:(248–258) Jan. 1997.

Liljeström; Alphavirus Vectors for Gene Delivery, OECD Documents, Gene Delivery Systems, 1996, pp. 109–118, XP002093351.

Liljeström; Alphavirus Expression Systems, Current Opinion in Biotechnology, 5:(495–500) 1994.

Sindbis Virus(HRSP and Wild–Type Strains) complete Genome, EMBL Database, Accession Nos. J02363, J02364, J02366, J02367 and V00073, Jul. 3, 1991.

Simpson et al.; Sindbis–like Virus Isolate–Girdwood S.A., Complete Genome, EMBL Database, Accession No. U38304, Jan. 3, 1996.

Russell et al.; Sindbis Virus Mutations Which Coordinately Affect Glycoprotein Processing, Penetration, and Virulence in Mice, Journal of Virology, vol. 63, No. 4, pp. 1619–1629, Apr. 1989.

Lemm et al.; Polypeptide requirements for assembly of functional Sindbis virus replication complexes: a model for the temporal regulation of minus–and plus–strand RNA, The EMBO Journal, vol. 13, No. 12, pp. 2925–2934, 1994.

Grieder et al.; Specific Restrictions in the Progression of Venezuelan Equine Encephalitis Virus–Induced Disease Resulting from Single Amino Acid Changes in the Glycoproteins, Virology 206, pp. 994–1006, 1995.

Corsini et al.; Efficiency of Transduction by Recombinant Sindbis Replicon Virus Among Cell Lines, Including Mosquito Cells and Rat Sensory Neurons, BioTechniques, vol. 21, No. 3, pp. 492–497, Sep. 1996.

McKnight et al.; Deduced Consensus Sequence of Sindbus Virus Strain AR339: Mutations Contained in Laboratory Strains Which Affect Cell Culture and In Vivo Phenotypes, J. of Virology, 70(3):1981–1989 (1996).

Simpson et al.; Complete Nucleotide Sequence and Full–Length cDNA Clone of S.A.AR86, a South African Alphavirus Related to Sindbis, Virology, 222 464–469 (1996).

Bredenbeek et al.; Sindbis Virus Expression Vectors: Packaging of RNA Replicons by Using Defective Helper RNAs, J. of Virology, 67(11):6439–6446 (1993).

Davis et al.; Attenuated Mutants of Venezuelan Equine Encephalitis Virus Containing Lethal Mutations in the PE2 Cleavage Signal Combined with a Second–Site Suppressor Mutation in E1, Virology 212:102–110 (1995).

(List continued on next page.)

*Primary Examiner*—John S. Brusca
*Attorney, Agent, or Firm*—Myers Bigel Sibley & Sajovec, P.A.

[57] ABSTRACT

The present invention provides a method of delivering immunogenic or therapeutic proteins to bone marrow cells using alphavirus vectors. The alphavirus vectors disclosed herein target specifically to bone marrow tissue, and viral genomes persist in bone marrow for at least three months post-infection. No or very low levels of virus were detected in quadricep, brain, and sera of treated animals. The sequence of a consensus Sindbis cDNA clone, pTR339, and infectious RNA transcripts, infectious virus particles, and pharmaceutical formulations derived therefrom are also disclosed. The sequence of the genomic RNA of the Girdwood S.A. virus, and cDNA clones, infectious RNA transcripts, infectious virus particles, and pharmaceutical formulations derived therefrom are also disclosed.

52 Claims, No Drawings

OTHER PUBLICATIONS

Davis et al.; A Genetically Engineered Live Virus Vaccine for Venezuelan Equine Encephalitis (Abstract N404), *J. Cell Biochemistry*, Supplement 0 No. 17 Part D:79 (1993).

Davis et al.; Attenuating Mutations in the E2 Glycoprotein Gene of Venezuelan Equine Encephalitis Virus: Construction of Single and Multiple Mutants in a Full–Length cDNA Clone, *Virology*, 183:20–31 (1991).

Frolov et al.; Alphavirus–based expression vectors: Strategies and applications, *Proc. Natl. Acad. Sci. USA*, 93:11371–11377 (1996).

Hahn et al., Infectious Sindbis virus transient expression vectors for studying antigen processing and presentation, *Proc. Natl. Acad. Sci. USA* 89:2679–2683 (1992).

Liljeström et al.; A New Generation of Animal Cell Expression Vectors Based on the Semliki Forest Virus Replicon, *Bio/Technology*, 9:1356–1361 (1991).

London et al., Infectious enveloped RNA virus antigenic chimeras, *Proc. Natl. Acad. Sci. USA*, 89:207–211 (1992).

Morgenstern et al.; Advanced mammalian gene transfer: high titre retroviral vectors with multiple drug selection markers and a complementary helper–free packaging cell line, *Nucleic Acids Research*, 18(12):3587–3596 (1990).

Polo et al.; Attenuating Mutations in Glycoproteins E1 and E2 of Sindbis Virus Produce a Highly Attenuated Strain When Combined In Vitro, *J. of Virology*, 64(9):4438–4444 (1990).

Schoepp et al.; Directed Mutagenesis of a Sindbis Virus Pathogenesis Site, *Virology*, 193:149–159 (1993).

Strauss et al.; The Alphaviruses: Gene Expression, Replication, and Evolution, Biological Reviews, 58(3):491–562 (1994).

Suomalainen et al.; Spike Protein–Nucleocapsid Drive the Budding of Alphavirus, *J. of Virology* 66(8):4737–4747 (1992).

SYSTEM FOR THE IN VIVO DELIVERY AND EXPRESSION OF HETEROLOGOUS GENES IN THE BONE MARROW

RELATED APPLICATIONS

This application is a divisional of U.S. application Ser. No. 08/801,263, filed on Feb. 19, 1997, U.S. Pat. No. 5,811,407 which is hereby incorporated by reference in its entirety.

FEDERALLY SPONSORED RESEARCH

This invention was made with Government support under Grant Number 5 RO1 AI22186 from the National Institutes of Health. The Government has certain rights to this invention.

FIELD OF THE INVENTION

The present invention relates to recombinant DNA technology, and in particular to introducing and expressing foreign DNA in a eukaryotic cell.

BACKGROUND OF THE INVENTION

The Alphavirus genus includes a variety of viruses all of which are members of the Togaviridae family. The alphaviruses include Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African Arbovirus No. 86 (S.A.AR 86), Girdwood S.A. virus, Ockelbo virus, Semliki Forest virus, Middelburg virus, Chikungunya virus, O'Nyong-Nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, and Buggy Creek virus.

The alphavirus genome is a single-stranded, messenger-sense RNA, modified at the 5'-end with a methylated cap, and at the 3'-end with a variable-length poly (A) tract. The viral genome is divided into two regions: the first encodes the nonstructural or replicase proteins (nsP1–nsP4) and the second encodes the viral structural proteins. Strauss and Strauss, *Microbiological Rev.* 58, 491–562, 494 (1994). Structural subunits consisting of a single viral protein, C, associate with themselves and with the RNA genome in an icosahedral nucleocapsid. In the virion, the capsid is surrounded by a lipid envelope covered with a regular array of transmembranal protein spikes, each of which consists of a heterodimeric complex of two glycoproteins, E1 and E2. See Paredes et al., *Proc. Natl. Acad. Sci. USA* 90, 9095–99 (1993); Paredes et al., *Virology* 187, 324–32 (1993); Pedersen et al., *J. Virol.* 14:40 (1974).

Sindbis virus, the prototype member of the alphavirus genus of the family Togaviridae, and viruses related to Sindbis are broadly distributed throughout Africa, Europe, Asia, the Indian subcontinent, and Australia, based on serological surveys of humans, domestic animals and wild birds. Kokemot et al., *Trans. R. Soc. Trop Med. Hyg.* 59, 553–62 (1965); Redaksie, *S. Afr. Med. J.* 42, 197 (1968); Adekolu-John and Fagbami, *Trans. R. Soc. Trop. Med. Hyg.* 77, 149–51 (1983); Darwish et al., *Trans. R. Soc. Trop. Med. Hyg.* 77, 442–45 (1983); Lundström et al., *Epidemiol. Infect.* 106, 567–74 (1991); Morrill et al., *J. Trop. Med. Hyg.* 94, 166–68 (1991). The first isolate of Sindbis virus (strain AR339) was recovered from a pool of Culex sp. mosquitoes collected in Sindbis, Egypt in 1953 (Taylor et al., *Am. J. Trop. Med. Hyg.* 4, 844–62 (1955)), and is the most extensively studied representative of this group. Other members of the Sindbis group of alphaviruses include South African Arbovirus No. 86, Ockelbo82, and Girdwood S.A. These viruses are not strains of the Sindbis virus; they are related to Sindbis AR339, but they are more closely related to each other based on nucleotide sequence and serological comparisons. Lundström et al., *J. Wildl. Dis.* 29, 189–95 (1993); Simpson et al., *Virology* 222, 464–69 (1996). Ockelbo82, S.A.AR86 and Girdwood S.A. are all associated with human disease, whereas Sindbis is not. The clinical symptoms of human infection with Ockelbo82, S.A.AR86, or Girdwood S.A. are a febrile illness, general malaise, macropapular rash, and joint pain that occasionally progresses to a polyarthralgia sometimes lasting from a few months to a few years.

The study of these viruses has led to the development of beneficial techniques for vaccinating against the alphavirus diseases, and other diseases through the use of alphavirus vectors for the introduction of foreign DNA. See U.S. Pat. No. 5,185,440 to Davis et al., and PCT Publication WO 92/10578. It is intended that all United States patent references be incorporated in their entirety by reference.

It is well known that live, attenuated viral vaccines are among the most successful means of controlling viral disease. However, for some virus pathogens, immunization with a live virus strain may be either impractical or unsafe. One alternative strategy is the insertion of sequences encoding immunizing antigens of such agents into a vaccine strain of another virus. One such system utilizing a live VEE vector is described in U.S. Pat. No. 5,505,947 to Johnston et al.

Sindbis virus vaccines have been employed as viral carriers in virus constructs which express genes encoding immunizing antigens for other viruses. See U.S. Pat. No. 5,217,879 to Huang et al. Huang et al. describes Sindbis infectious viral vectors. However, the reference does not describe the cDNA sequence of Girdwood S.A. and TR339, nor clones or viral vectors produced therefrom.

Another such system is described by Hahn et al., *Proc. Natl. Acad. Sci. USA* 89:2679 (1992), wherein Sindbis virus constructs which express a truncated form of the influenza hemagglutinin protein are described. The constructs are used to study antigen processing and presentation in vitro and in mice. Although no infectious challenge dose is tested, it is also suggested that such constructs might be used to produce protective B- and T-cell mediated immunity.

London et al., *Proc. Natl. Acad. Sci, USA* 89, 207–11 (1992), disclose a method of producing an immune response in mice against a lethal Rift Valley Fever (RVF) virus by infecting the mice with an infectious Sindbis virus containing an RVF epitope. London does not disclose using Girdwood S.A. or TR339 to induce an immune response in animals.

Viral carriers can also be used to introduce and express foreign DNA in eukaryotic cells. One goal of such techniques is to employ vectors that target expression to particular cells and/or tissues. A current approach has been to remove target cells from the body, culture them ex vivo, infect them with an expression vector, and then reintroduce them into the patient.

PCT Publication No. WO 92/10578 to Garoff and Liljeström provide a system for introducing and expressing foreign proteins in animal cells using alphaviruses. This reference discloses the use of Semliki Forest virus to introduce and express foreign proteins in animal cells. The use of Girdwood S.A. or TR339 is not discussed. Furthermore, this reference does not provide a method of targeting and introducing foreign DNA into specific cell or tissue types.

Accordingly, there remains a need in the art for full-length cDNA clones of positive-strand RNA viruses, such as Girdwood S.A and TR339. In addition, there is an ongoing need in the art for improved vaccination strategies. Finally, there remains a need in the art for improved methods and nucleic acid sequences for delivering foreign DNA to target cells.

SUMMARY OF THE INVENTION

A first aspect of the present invention is a method of introducing and expressing heterologous RNA in bone marrow cells, comprising: (a) providing a recombinant alphavirus, the alphavirus containing a heterologous RNA segment, the heterologous RNA segment comprising a promoter operable in bone marrow cells operatively associated with a heterologous RNA to be expressed in bone marrow cells; and then (b) contacting the recombinant alphavirus to the bone marrow cells so that the heterologous RNA segment is introduced and expressed therein.

As a second aspect, the present invention provides a helper cell for expressing an infectious, propagation defective, Girdwood S.A. virus particle, comprising, in a Girdwood S.A.-permissive cell: (a) a first helper RNA encoding (i) at least one Girdwood S.A. structural protein, and (ii) not encoding at least one other Girdwood S.A. structural protein; and (b) a second helper RNA separate from the first helper RNA, the second helper RNA (i) not encoding the at least one Girdwood S.A. structural protein encoded by the first helper RNA, and (ii) encoding the at least one other Girdwood S.A. structural protein not encoded by the first helper RNA, and with all of the Girdwood S.A. structural proteins encoded by the first and second helper RNAs assembling together into Girdwood S.A. particles in the cell containing the replicon RNA; and wherein the Girdwood S.A. packaging segment is deleted from at least the first helper RNA.

A third aspect of the present invention is a method of making infectious, propagation defective, Girdwood S.A. virus particles, comprising: transfecting a Girdwood S.A.-permissive cell with a propagation defective replicon RNA, the replicon RNA including the Girdwood S.A. packaging segment and an inserted heterologous RNA; producing the Girdwood S.A. virus particles in the transfected cell; and then collecting the Girdwood S.A. virus particles from the cell. Also disclosed are infectious Girdwood S.A. RNAs, cDNAs encoding the same, infectious Girdwood S.A. virus particles, and pharmaceutical formulations thereof.

As a fourth aspect, the present invention provides a helper cell for expressing an infectious, propagation defective, TR339 virus particle, comprising, in a TR339-permissive cell: (a) a first helper RNA encoding (i) at least one TR339 structural protein, and (ii) not encoding at least one other TR339 structural protein; and (b) a second helper RNA separate from the first helper RNA, the second helper RNA (i) not encoding the at least one TR339 structural protein encoded by the first helper RNA, and (ii) encoding the at least one other TR339 structural protein not encoded by the first helper RNA, and with all of the TR339 structural proteins encoded by the first and second helper RNAs assembling together into TR339 particles in the cell containing the replicon RNA; and wherein the TR339 packaging segment is deleted from at least the first helper RNA.

A fifth aspect of the present invention is a method of making infectious, propagation defective, TR339 virus particles, comprising: transfecting a TR339-permissive cell with a propagation defective replicon RNA, the replicon RNA including the TR339 packaging segment and an inserted heterologous RNA; producing the TR339 virus particles in the transfected cell; and then collecting the TR339 virus particles from the cell. Also disclosed are infectious TR339 RNAs, cDNAs encoding the same, infectious TR339 virus particles, and pharmaceutical formulations thereof.

As a sixth aspect, the present invention provides a recombinant DNA comprising a cDNA coding for an infectious Girdwood S.A. virus RNA transcript, and a heterologous promoter positioned upstream from the cDNA and operatively associated therewith. The present invention also provides infectious RNA transcripts encoded by the above-mentioned cDNA and infectious viral particles containing the infectious RNA transcripts.

As a seventh aspect, the present invention provides a recombinant DNA comprising a cDNA coding for a Sindbis strain TR339 RNA transcript, and a heterologous promoter positioned upstream from the cDNA and operatively associated therewith. The present invention also provides infectious RNA transcripts encoded by the above-mentioned cDNA and infectious viral particles containing the infectious RNA transcripts.

The foregoing and other aspects of the present invention are described in the detailed description set forth below.

DETAILED DESCRIPTION OF THE INVENTION

The production and use of recombinant DNA, vectors, transformed host cells, selectable markers, proteins, and protein fragments by genetic engineering are well-known to those skilled in the art. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col 3 line 26 to Col 14 line 12; and U.S. Pat. No. 4,879,224 to Wallner at Col. 6 line 8 to Col. 8 line 59.

The term "alphavirus" has its conventional meaning in the art, and includes the various species of alphaviruses such as Eastern Equine Encephalitis virus (EEE), Venezuelan Equine Encephalitis virus (VEE), Everglades virus, Mucambo virus, Pixuna virus, Western Encephalitis virus (WEE), Sindbis virus, South African Arbovirus No. 86, Girdwood S.A. virus, Ockelbo virus, Semliki Forest virus, Middelburg virus, Chikungunya virus, O'Nyong-Nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, Buggy Creek virus, and any other virus classified by the International Committee on Taxonomy of Viruses (ICTV) as an alphavirus. The preferred alphaviruses for use in the present invention include Sindbis virus strains (e.g., TR339), Girdwood S.A., S.A.AR86, and Ockelbo82.

An "Old World alphavirus" is a virus that is primarily distributed throughout the Old World. Alternately stated, an Old World alphavirus is a virus that is primarily distributed throughout Africa, Asia, Australia and New Zealand, or Europe. Exemplary Old World viruses include SF group alphaviruses and SIN group alphaviruses. SF group alphaviruses include Semliki Forest virus, Middelburg virus, Chikungunya virus, O'Nyong-Nyong virus, Ross River virus, Barmah Forest virus, Getah virus, Sagiyama virus, Bebaru virus, Mayaro virus, and Una virus. SIN group alphaviruses include Sindbis virus, South African Arbovirus No. 86, Ockelbo virus, Girdwood S.A. virus, Aura virus, Whataroa virus, Babanki virus, and Kyzylagach virus.

Acceptable alphaviruses include those containing attenuating mutations. The phrases "attenuating mutation" and "attenuating amino acid," as used herein, mean a nucleotide sequence containing a mutation, or an amino acid encoded by a nucleotide sequence containing a mutation, which mutation results in a decreased probability of causing disease in its host (i.e., a loss of virulence), in accordance with standard terminology in the art, whether the mutation be a substitution mutation or an in-frame deletion mutation. See, e.g., B. DAVIS ET AL., MICROBIOLOGY 132 (3d ed. 1980). The phrase "attenuating mutation" excludes mutations or combinations of mutations which would be lethal to the virus.

Appropriate attenuating mutations will be dependent upon the alphavirus used. Suitable attenuating mutations within the alphavirus genome will be known to those skilled in the art. Exemplary attenuating mutations include, but are not limited to, those described in U.S. Pat. No. 5,505,947 to Johnston et al., U.S. Pat. No. 5,792,462 to Johnston et al., and U.S. Pat. No. 5,639,650 to Johnston et al. It is intended that all United States patent references be incorporated in their entirety by reference.

Attenuating mutations may be introduced into the RNA by performing site-directed mutagenesis on the cDNA which encodes the RNA, in accordance with known procedures. See, Kunkel, *Proc. Natl. Acad. Sci. USA* 82, 488 (1985), the disclosure of which is incorporated herein by reference in its entirety. Alternatively, mutations may be introduced into the RNA by replacement of homologous restriction fragments in the cDNA which encodes for the RNA, in accordance with known procedures.

I. Methods for Introducing and Expressing Heterologous RNA in Bone Marrow Cells

The present invention provides methods of using a recombinant alphavirus to introduce and express a heterologous RNA in bone marrow cells. Such methods are useful as vaccination strategies when the heterologous RNA encodes an immunogenic protein or peptide. Alternatively, such methods are useful in introducing and expressing in bone marrow cells an RNA which encodes a desirable protein or peptide, for example, a therapeutic protein or peptide.

The present invention is carried out using a recombinant alphavirus to introduce a heterologous RNA into bone marrow cells. Any alphavirus that targets and infects bone marrow cells is suitable. Preferred alphaviruses include Old World alphaviruses, more preferably SF group alphaviruses and SIN group alphaviruses, more preferably Sindbis virus strains (e.g., TR339), S.A.AR86 virus, Girdwood S.A. virus, and Ockelbo virus. In a more preferred embodiment, the alphavirus contains one or more attenuating mutations, as described hereinabove.

Two types of recombinant virus vector are contemplated in carrying out the present invention. In one embodiment employing "double promoter vectors," the heterologous RNA is inserted into a replication and propagation competent virus. Double promoter vectors are described in U.S. Pat. No. 5,505,947 to Johnston et al. With this type of viral vector, it is preferable that heterologous RNA sequences of less than 3 kilobases are inserted into the viral vector, more preferably those less than 2 kilobases, and more preferably still those less than 1 kilobase. In an alternate embodiment, propagation-defective "replicon vectors," as described in U.S. Pat. No. 5,792,462, will be used. One advantage of replicon viral vectors is that larger RNA inserts, up to approximately 4–5 kilobases in length can be utilized. Double promoter vectors and replicon vectors are described in more detail hereinbelow.

The recombinant alphaviruses of the claimed method target the heterologous RNA to bone marrow cells, where it expresses the encoded protein or peptide. Heterologous RNA can be introduced and expressed in any cell type found in the bone marrow. Bone marrow cells that may be targeted by the recombinant alphaviruses of the present invention include, but are not limited to, polymorphonuclear cells, hemopoietic stem cells (including megakaryocyte colony forming units (CFU-M), spleen colony forming units (CFU-S), erythroid colony forming units (CFU-E), erythroid burst forming units (BFU-E), and colony forming units in culture (CFU-C)), erythrocytes, macrophages (including reticular cells), monocytes, granulocytes, megakaryoctyes, lymphocytes, fibroblasts, osteoprogenitor cells, and stromal cells.

By targeting to the cells of the bone marrow, it is meant that the primary site in which the virus will be localized in vivo is the cells of the bone marrow. Alternately stated, the alphaviruses of the present invention target bone marrow cells, such that titers in bone marrow two days after infection are greater than 100 PFU/g crushed bone, preferably greater than 200 PFU/g crushed bone, more preferably greater than 300 PFU/g crushed bone, and more preferably still greater than 500 PFU/g crushed bone. Virus may be detected occasionally in other cell or tissue types, but only sporadically and usually at low levels. Virus localization in the bone marrow can be demonstrated by any suitable technique known in the art, such as in situ hybridization.

Bone marrow cells are long-lived and harbor infectious alphaviruses for a prolonged period of time, as demonstrated in the Examples below. These characteristics of bone marrow cells render the present invention useful not only for the purpose of supplying a desired protein or peptide to skeletal tissue, but also for expressing proteins or peptides in vivo that are needed by other cell or tissue types.

The present invention can be carried out in vivo or with cultured bone marrow cells in vitro. Bone marrow cell cultures include primary cultures of bone marrow cells, serially-passaged cultures of bone marrow cells, and cultures of immortalized bone marrow cell lines. Bone marrow cells may be cultured by any suitable means known in the art.

The recombinant alphaviruses of the present invention carry a heterologous RNA segment. The heterologous RNA segment encodes a promoter and an inserted heterologous RNA. The inserted heterologous RNA may encode any protein or a peptide which is desirably expressed by the host bone marrow cells. Suitable heterologous RNA may be of prokaryotic (e.g., RNA encoding the Botulinus toxin C), or eukaryotic (e.g., RNA encoding malaria Plasmodium protein cs1) origin. Illustrative proteins and peptides encoded by the heterologous RNAs of the present invention include hormones, growth factors, interleukins, cytokines, chemokines, enzymes, and ribozymes. Alternately, the heterologous RNAs encode any therapeutic protein or peptide. As a further alternative, the heterologous RNAs of the present invention encode any immunogenic protein or peptide.

An immunogenic protein or peptide, or "immunogen," may be any protein or peptide suitable for protecting the subject against a disease, including but not limited to microbial, bacterial, protozoal, parasitic, and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV envelope GP160 protein and the HIV matrix/capsid proteins). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia), a flavivirus immunogen (e.g., a yellow fever virus immunogen or a Japanese encephalitis virus immunogen), a filovirus immunogen (e.g., an Ebola virus immunogen, or a Marburg virus immunogen), a bunyavirus immunogen (e.g., RVFV, CCHF, and SFS viruses), or a coronavirus immunogen (e.g., an infectious human coronavirus immunogen, such as the human coronavirus envelope glycoprotein gene, or a transmissible gastroenteritis virus immunogen for pigs, or an infectious bronchitis virus immunogen for chickens).

Alternatively, the present invention can be used to express heterologous RNAs encoding antisense oligonucleotides. In general, "antisense" refers to the use of small, synthetic oligonucleotides to inhibit gene expression by inhibiting the function of the target mRNA containing the complementary sequence. Milligan, J. F. et al., *J. Med. Chem.* 36(14), 1923–1937 (1993). Gene expression is inhibited through hybridization to coding (sense) sequences in a specific mRNA target by hydrogen bonding according to Watson-Crick base pairing rules. The mechanism of antisense inhibition is that the exogenously applied oligonucleotides decrease the mRNA and protein levels of the target gene. Milligan, J. F. et al., *J. Med. Chem.* 36(14), 1923–1937 (1993). See also Helene, C. and Toulme, *J., Biochim. Biophys. Acta* 1049, 99–125 (1990); Cohen, J. S., Ed., OLIGODEOXYNUCLEOTIDES AS ANTISENSE INHIBITORS OF GENE EXPRESSION, CRC Press:Boca Raton, Fla. (1987).

Antisense oligonucleotides may be of any suitable length, depending on the particular target being bound. The only limits on the length of the antisense oligonucleotide is the capacity of the virus for inserted heterologous RNA. Antisense oligonucleotides may be complementary to the entire mRNA transcript of the target gene or only a portion thereof. Preferably the antisense oligonucleotide is directed to an mRNA region containing a junction between intron and exon. Where the antisense oligonucleotide is directed to an intron/exon junction, it may either entirely overlie the junction or may be sufficiently close to the junction to inhibit splicing out of the intervening exon during processing of precursor mRNA to mature mRNA (e.g., with the 3' or 5' terminus of the antisense oligonucleotide being positioned within about, for example, 10, 5, 3 or 2 nucleotides of the intron/exon junction). Also preferred are antisense oligonucleotides which overlap the initiation codon.

When practicing the present invention, the antisense oligonucleotides administered may be related in origin to the species to which it is administered. When treating humans, human antisense may be used if desired.

Promoters for use in carrying out the present invention are operable in bone marrow cells. An operable promoter in bone marrow cells is a promoter that is recognized by and functions in bone marrow cells. Promoters for use with the present invention must also be operatively associated with the heterologous RNA to be expressed in the bone marrow. A promoter is operably linked to a heterologous RNA if it controls the transcription of the heterologous RNA, where the heterologous RNA comprises a coding sequence. Suitable promoters are well known in the art. The Sindbis 26S promoter is preferred when the alphavirus is a strain of Sindbis virus. Additional preferred promoters beyond the Sindbis 26S promoter include the Girdwood S.A. 26S promoter when the alphavirus is Girdwood S.A., the S.A.AR86 26S promoter when the alphavirus is S.A.AR86, and any other promoter sequence recognized by alphavirus polymerases. Alphavirus promoter sequences containing mutations which alter the activity level of the promoter (in relation to the activity level of the wild-type) are also suitable in the practice of the present invention. Such mutant promoter sequences are described in Raju and Huang, *J. Virol.* 65, 2501–2510 (1991), the disclosure of which is incorporated in its entirety by reference.

The heterologous RNA is introduced into the bone marrow cells by contacting the recombinant alphavirus carrying the heterologous RNA segment to the bone marrow cells. By contacting, it is meant bringing the recombinant alphavirus and the bone marrow cells in physical proximity. The contacting step can be performed in vitro or in vivo. In vitro contacting can be carried out with cultures of immortalized or non-immortalized bone marrow cells. In one particular embodiment, bone marrow cells can be removed from a subject, cultured in vitro, infected with the vector, and then introduced back into the subject. Contacting is performed in vivo when the recombinant alphavirus is administered to a subject. Pharmaceutical formulations of recombinant alphavirus can be administered to a subject parenterally (e.g., subcutaneous, intracerebral, intradermal, intramuscular, intravenous and intraarticular) administration. Alternatively, pharmaceutical formulations of the present invention may be suitable for administration to the mucus membranes of a subject (e.g., intranasal administration, by use of a dropper, swab, or inhaler). Methods of preparing infectious virus particles and pharmaceutical formulations thereof are discussed in more detail hereinbelow.

By "introducing" the heterologous RNA segment into the bone marrow cells it is meant infecting the bone marrow cells with recombinant alphavirus containing the heterologous RNA, such that the viral vector carrying the heterologous RNA enters the bone marrow cells and can be expressed therein. As used with respect to the present invention, when the heterologous RNA is "expressed," it is meant that the heterologous RNA is transcribed. In particular embodiments of the invention in which it is desired to produce a protein or peptide, expression further includes the steps of post-transcriptional processing and translation of the mRNA transcribed from the heterologous RNA. In contrast, where the heterologous RNA encodes an antisense oligonucleotide, expression need not include post-transcriptional processing and translation. With respect to embodiments in which the heterologous RNA encodes an immunogenic protein or a protein being administered for therapeutic purposes, expression may also include the further step of post-translational processing to produce an immunogenic or therapeutically-active protein.

The present invention also provides infectious RNAs, as described hereinabove, and cDNAs encoding the same. Preferably the infectious RNAs and cDNAs are derived from the S.A.AR86, Girdwood S.A., TR339, or Ockelbo viruses. The cDNA clones can be generated by any of a variety of suitable methods known to those skilled in the art. A preferred method is the method set forth in U.S. Pat. No. 5,185,440 to Davis et al., the disclosure of which is incorporated in its entirety by reference, and Gubler et al., *Gene* 25:263 (1983).

RNA is preferably synthesized from the DNA sequence in vitro using purified RNA polymerase in the presence of ribonucleotide triphosphates and cap analogs in accordance with conventional techniques. However, the RNA may also be synthesized intracellularly after introduction of the cDNA.

A. Double Promoter Vectors

In one embodiment of the invention, double promoter vectors are used to introduce the heterologous RNA into the target bone marrow cells. A double promoter virus vector is a replication and propagation competent virus. Double promoter vectors are described in U.S. Pat. No. 5,505,947 to Johnston et al., the disclosure of which is incorporated in its entirety by reference. Preferred alphaviruses for constructing the double promoter vectors are S.A.AR86, Girdwood S.A., TR339 and Ockelbo viruses. More preferably, the double promoter vector contains one or more attenuating mutations. Attenuating mutations are described in more detail hereinabove.

The double promoter vector is constructed so as to contain a second subgenomic promoter (i.e., 26S promoter) inserted 3' to the virus RNA encoding the structural proteins. The heterologous RNA is inserted between the second subgenomic promoter, so as to be operatively associated therewith, and the 3' UTR of the virus genome. Heterologous RNA sequences of less than 3 kilobases, more preferably those less than 2 kilobases, and more preferably still those less than 1 kilobase, can be inserted into the double promoter vector. In a preferred embodiment of the invention, the double promoter vector is derived from Girdwood S.A., and the second subgenomic promoter is a duplicate of the Girdwood S.A. subgenomic promoter. In an alternate preferred embodiment, the double promoter vector is derived from TR339, and the second subgenomic promoter is a duplicate of the TR339 subgenomic promoter.

B. Replicon Vectors

Replicon vectors, which are propagation-defective virus vectors can also be used to carry out the present invention. Replicon vectors are described in more detail in U.S. Pat. No. 5,792,462, the disclosure of which is incorporated in its entirety by reference. Preferred alphaviruses for constructing the replicon vectors are S.A.AR86, Girdwood S.A., TR339, and Ockelbo.

In general, in the replicon system, a foreign gene to be expressed is inserted in place of at least one of the viral structural protein genes in a transcription plasmid containing an otherwise full-length cDNA copy of the alphavirus genome RNA. RNA transcribed from this plasmid contains an intact copy of the viral nonstructural genes which are responsible for RNA replication and transcription. Thus, if the transcribed RNA is transfected into susceptible cells, it will be replicated and translated to give the nonstructural proteins. These proteins will transcribe the transfected RNA to give high levels of subgenomic mRNA, which will then be translated to produce high levels of the foreign protein. The autonomously replicating RNA (i.e., replicon) can only be packaged into virus particles if the alphavirus structural protein genes are provided on one or more "helper" RNAs, which are cotransfected into cells along with the replicon RNA. The helper RNAs do not contain the viral nonstructural genes for replication, but these functions are provided in trans by the replicon RNA. Similarly, the transcriptase functions translated from the replicon RNA transcribe the structural protein genes on the helper RNA, resulting in the synthesis of viral structural proteins and packaging of the replicon into virus-like particles. As the packaging or encapsidation signal for alphavirus RNAs is located within the nonstructural genes, the absence of these sequences in the helper RNAs precludes their incorporation into virus particles.

Alphavirus-permissive cells employed in the methods of the present invention are cells which, upon transfection with the viral RNA transcript, are capable of producing viral particles. Preferred alphavirus-permissive cells are TR339-permissive cells, Girdwood S.A.-permissive cells, S.A.AR86-permissive cells, and Ockelbo-permissive cells. Alphaviruses have a broad host range. Examples of suitable host cells include, but are not limited to Vero cells, baby hamster kidney (BHK) cells, and chicken embryo fibroblast cells.

The phrase "structural protein" as used herein refers to the encoded proteins which are required for encapsidation (e.g., packaging) of the RNA replicon, and include the capsid protein, E1 glycoprotein, and E2 glycoprotein. As described hereinabove, the structural proteins of the alphavirus are distributed among one or more helper RNAs (i.e., a first helper RNA and a second helper RNA). In addition, one or more structural proteins may be located on the same RNA molecule as the replicon RNA, provided that at least one structural protein is deleted from the replicon RNA such that the resulting alphavirus particle is propagation defective. As used herein, the terms "deleted" or "deletion" mean either total deletion of the specified segment or the deletion of a sufficient portion of the specified segment to render the segment inoperative or nonfunctional, in accordance with standard usage. See, e.g., U.S. Pat. No. 4,650,764 to Temin et al. The term "propagation defective" as used herein, means that the replicon RNA cannot be encapsidated in the host cell in the absence of the helper RNA. The resulting alphavirus particles are propagation defective inasmuch as the replicon RNA does not include all of the alphavirus structural proteins required for encapsidation, at least one of the required structural proteins being deleted therefrom, such that the packaged replicon RNA is not capable of replicating the entire viral genome.

The helper cell for expressing the infectious, propagation defective alphavirus particle comprises a set of RNAs, as described above. The set of RNAs principally include a first helper RNA and a second helper RNA. The first helper RNA includes RNA encoding at least one alphavirus structural protein but does not encode all alphavirus structural proteins. In other words, the first helper RNA does not encode at least one alphavirus structural protein; the at least one non-coded alphavirus structural protein being deleted from the first helper RNA. In one embodiment, the first helper RNA includes RNA encoding the alphavirus E1 glycoprotein, with the alphavirus capsid protein and the alphavirus E2 glycoprotein being deleted from the first helper RNA. In another embodiment, the first helper RNA includes RNA encoding the alphavirus E2 glycoprotein, with the alphavirus capsid protein and the alphavirus E1 glycoprotein being deleted from the first helper RNA. In a third, preferred embodiment, the first helper RNA includes RNA encoding the alphavirus E1 glycoprotein and the alphavirus E2 glycoprotein, with the alphavirus capsid protein being deleted from the first helper RNA.

The second helper RNA includes RNA encoding at least one alphavirus structural protein which is different from the at least one structural protein encoded by the first helper RNA. Thus, the second helper RNA encodes at least one alphavirus structural protein which is not encoded by the first helper RNA. The second helper RNA does not encode the at least one alphavirus structural protein which is encoded by the first helper RNA, thus the first and second helper RNAs do not encode duplicate structural proteins. In the embodiment wherein the first helper RNA includes RNA encoding only the alphavirus E1 glycoprotein, the second helper RNA may include RNA encoding one or both of the alphavirus capsid protein and the alphavirus E2 glycoprotein which are deleted from the first helper RNA. In the embodiment wherein, the first helper RNA includes RNA encoding only the alphavirus E2 glycoprotein, the second helper RNA may include RNA encoding one or both of the alphavirus capsid protein and the alphavirus E1 glycoprotein which are deleted from the first helper RNA. In the embodiment wherein the first helper RNA includes RNA encoding both the alphavirus E1 glycoprotein and the alphavirus E2 glycoprotein, the second helper RNA may include RNA encoding the alphavirus capsid protein which is deleted from the first helper RNA.

In one embodiment, the packaging segment (RNA comprising the encapsidation or packaging signal) is deleted from at least the first helper RNA. In a preferred embodiment, the packaging segment is deleted from both the first helper RNA and the second helper RNA.

In the preferred embodiment wherein the packaging segment is deleted from both the first helper RNA and the second helper RNA, the helper cell is co-transfected with a replicon RNA in addition to the first helper RNA and the second helper RNA. The replicon RNA encodes the packaging segment and an inserted heterologous RNA. The inserted heterologous RNA may be RNA encoding a protein or a peptide. In a preferred embodiment, the replicon RNA, the first helper RNA and the second helper RNA are provided on separate molecules such that a first molecule, i.e., the replicon RNA, includes RNA encoding the packaging segment and the inserted heterologous RNA, a second molecule, i.e., the first helper RNA, includes RNA encoding at least one but not all of the required alphavirus structural proteins, and a third molecule, i.e., the second helper RNA, includes RNA encoding at least one but not all of the required alphavirus structural proteins. For example, in one preferred embodiment of the present invention, the helper cell includes a set of RNAs which include (a) a replicon RNA including RNA encoding an alphavirus packaging sequence and an inserted heterologous RNA, (b) a first helper RNA including RNA encoding the alphavirus E1 glycoprotein and the alphavirus E2 glycoprotein, and (c) a second helper RNA including RNA encoding the alphavirus capsid protein so that the alphavirus E1 glycoprotein, the alphavirus E2 glycoprotein and the capsid protein assemble together into alphavirus particles in the host cell.

In an alternate embodiment, the replicon RNA and the first helper RNA are on separate molecules, and the replicon RNA and RNA encoding a structural gene not encoded by the first helper RNA are on another single molecule together, such that a first molecule, i.e., the first helper RNA, including RNA encoding at least one but not all of the required alphavirus structural proteins, and a second molecule, i.e., the replicon RNA, including RNA encoding the packaging segment, the inserted heterologous RNA, and the remaining structural proteins not encoded by the first helper RNA. For example, in one preferred embodiment of the present invention, the helper cell includes a set of RNAs including (a) a replicon RNA including RNA encoding an alphavirus packaging sequence, an inserted heterologous RNA, and an alphavirus capsid protein, and (b) a first helper RNA including RNA encoding the alphavirus E1 glycoprotein and the alphavirus E2 glycoprotein so that the alphavirus E1 glycoprotein, the alphavirus E2 glycoprotein and the capsid protein assemble together into alphavirus particles in the host cell, with the replicon RNA packaged therein.

In one preferred embodiment of the present invention, the RNA encoding the alphavirus structural proteins, i.e., the capsid, E1 glycoprotein and E2 glycoprotein, contains at least one attenuating mutation, as described hereinabove. Thus, according to this embodiment, at least one of the first helper RNA and the second helper RNA includes at least one attenuating mutation. In a more preferred embodiment, at least one of the first helper RNA and the second helper RNA includes at least two, or multiple, attenuating mutations. The multiple attenuating mutations may be positioned in either the first helper RNA or in the second helper RNA, or they may be distributed randomly with one or more attenuating mutations being positioned in the first helper RNA and one or more attenuating mutations positioned in the second helper RNA. Alternatively, when the replicon RNA and the RNA encoding the structural proteins not encoded by the first helper RNA are located on the same molecule, an attenuating mutation may be positioned in the RNA which codes for the structural protein not encoded by the first helper RNA. The attenuating mutations may also be located within the RNA encoding non-structural proteins (e.g., the replicon RNA).

Preferably, the first helper RNA and the second helper RNA also include a promoter. It is also preferred that the replicon RNA also includes a promoter. Suitable promoters for inclusion in the first helper RNA, second helper RNA and replicon RNA are well known in the art. One preferred promoter is the Girdwood S.A. 26S promoter for use when the alphavirus is Girdwood S.A. Another preferred promoter is the TR339 26S promoter for use when the alphavirus is TR339. Additional promoters beyond the Girdwood S.A. and TR339 promoters include the VEE 26S promoter, the Sindbis 26S promoter, the Semliki Forest 26S promoter, and any other promoter sequence recognized by alphavirus polymerases. Alphavirus promoter sequences containing mutations which alter the activity level of the promoter (in relation to the activity level of the wild-type) are also suitable in the practice of the present invention. Such mutant promoter sequences are described in Raju and Huang, *J. Virol.* 65, 2501–2510 (1991), the disclosure of which is incorporated herein in its entirety. In the system wherein the first helper RNA, the second helper RNA, and the replicon RNA are all on separate molecules, the promoters, if the same promoter is used for all three RNAs, provide a homologous sequence between the three molecules. It is preferred that the selected promoter is operative with the non-structural proteins encoded by the replicon RNA molecule.

In cases where vaccination with two immunogens provides improved protection against disease as compared to vaccination with only a single immunogen, a double-promoter replicon would ensure that both immunogens are produced in the same cell. Such a replicon would be the same as the one described above, except that it would contain two copies of the 26S RNA promoter, each followed by a different multiple cloning site, to allow for the insertion and expression of two different heterologous proteins. Another useful strategy is to insert the IRES sequence from the picornavirus, EMC virus, between the two heterologous genes downstream from the single 26S promoter of the replicon described above, thus leading to expression of two immunogens from the single replicon transcript in the same cell.

C. Uses of the Present Invention

The alphavirus vectors, RNAs, cDNAs, helper cells, infectious virus particles, and methods of the present invention find use in in vitro expression systems, wherein the inserted heterologous RNA encodes a protein or peptide which is desirably produced in vitro. The RNAs, cDNAs, helper cells, infectious virus particles, methods, and pharmaceutical formulations of the present invention are additionally useful in a method of administering a protein or peptide to a subject in need of the protein or peptide, as a method of treatment or otherwise. In this embodiment of the invention, the heterologous RNA encodes the desired protein or peptide, and pharmaceutical formulations of the present invention are administered to a subject in need of the desired protein or peptide. In this manner, the protein or peptide may thus be produced in vivo in the subject. The subject may be in need of the protein or peptide because the subject has a deficiency thereof, or because the production of the protein or peptide in the subject may impart some therapeutic effect, as a method of treatment or otherwise.

Alternately, the claimed methods provide a vaccination strategy, wherein the heterologous RNA encodes an immunogenic protein or peptide.

The methods and products of the invention are also useful as antigens and for evoking the production of antibodies in animals such as horses and rabbits, from which the antibodies may be collected and then used in diagnostic assays in accordance with known techniques.

A further aspect of the present invention is a method of introducing and expressing antisense oligonucleotides in bone marrow cell cultures to regulate gene expression. Alternately, the claimed method finds use in introducing and expressing a protein or peptide in bone marrow cell cultures.

II. Girdwood S.A. and TR339 Clones

Disclosed hereinbelow are genomic RNA sequences encoding live Girdwood S.A. virus, live S.A.AR86 virus, and live Sindbis strain TR339 virus, cDNAs derived therefrom, infectious RNA transcripts encoded by the cDNAs, infectious viral particles containing the infectious RNA transcripts, and pharmaceutical formulations derived therefrom.

The cDNA sequence of Girdwood S.A. is given herein as SEQ ID NO:4. Alternatively, the cDNA may have a sequence which differs from the cDNA of SEQ ID NO:4, but which has the same protein sequence as the cDNA given herein as SEQ ID NO:4. Thus, the cDNA may include one or more silent mutations.

The phrase "silent mutation" as used herein refers to mutations in the CDNA coding sequence which do not produce mutations in the corresponding protein sequence translated therefrom.

Likewise, the cDNA sequence of TR339 is given herein as SEQ ID NO:8. Alternatively, the cDNA may have a sequence which differs from the cDNA of SEQ ID NO:8, but which has the same protein sequence as the cDNA given herein as SEQ ID NO:8. Thus, the cDNA may include one or more silent mutations.

The cDNAs encoding infectious Girdwood S.A. and TR339 virus RNA transcripts of the present invention include those homologous to, and having essentially the same biological properties as, the cDNA sequences disclosed herein as SEQ ID NO:4 and SEQ ID NO:8, respectively. Thus, cDNAs that hybridize to cDNAs encoding infectious Girdwood S.A. or TR339 virus RNA transcripts disclosed herein are also an aspect of this invention. Conditions which will permit other cDNAs encoding infectious Girdwood S.A. or TR339 virus transcripts to hybridize to the cDNAs disclosed herein can be determined in accordance with known techniques. For example, hybridization of such sequences may be carried out under conditions of reduced stringency, medium stringency, or even high stringency conditions (e.g., conditions represented by a wash stringency of 35–40% formamide with 5× Denhardt's solution, 0.5% SDS and 1× SSPE at 37° C.; conditions represented by a wash stringency of 40–45% formamide with 5× Denhardt's solution, 0.5% SDS, and 1× SSPE at 42° C.; and conditions represented by a wash stringency of 50% formamide with 5× Denhardt's solution, 0.5% SDS and 1× SSPE at 42° C., respectively, to cDNA encoding infectious Girdwood S.A. or TR339 virus RNA transcripts disclosed herein in a standard hybridization assay. See J. SAMBROOK ET AL., MOLECULAR CLONING: A LABORATORY MANUAL (2d ed. 1989)). In general, cDNA sequences encoding infectious Girdwood S.A. or TR339 virus RNA transcripts that hybridize to the cDNAs disclosed herein will be at least 30% homologous, 50% homologous, 75% homologous, and even 95% homologous or more with the cDNA sequences encoding infectious Girdwood S.A. or TR339 virus RNA transcripts disclosed herein.

Promoter sequences and Girdwood S.A. virus or Sindbis virus strain TR339 cDNA clones are operatively associated in the present invention such that the promoter causes the cDNA clone to be transcribed in the presence of an RNA polymerase which binds to the promoter. The promoter is positioned on the 5' end (with respect to the virion RNA sequence), of the cDNA clone. An excessive number of nucleotides between the promoter sequence and the cDNA clone will result in the inoperability of the construct. Hence, the number of nucleotides between the promoter sequence and the cDNA clone is preferably not more than eight, more preferably not more than five, still more preferably not more than three, and most preferably not more than one.

Examples of promoters which are useful in the cDNA sequences of the present invention include, but are not limited to T3 promoters, T7 promoters, cytomegalovirus (CMV) promoters, and SP6 promoters. The DNA sequence of the present invention may reside in any suitable transcription vector. The DNA sequence preferably has a complementary DNA sequence bound thereto so that the double-stranded sequence will serve as an active template for RNA polymerase. The transcription vector preferably comprises a plasmid. When the DNA sequence comprises a plasmid, it is preferred that a unique restriction site be provided 3' (with respect to the virion RNA sequence) to the cDNA clone. This provides a means for linearizing the DNA sequence to allow the transcription of genome-length RNA in vitro.

The cDNA clones can be generated by any of a variety of suitable methods known to those skilled in the art. A preferred method is the method set forth in U.S. Pat. No. 5,185,440 to Davis et al., the disclosure of which is incorporated in its entirety by reference, and Gubler et al., *Gene* 25:263 (1983).

RNA is preferably synthesized from the DNA sequence in vitro using purified RNA polymerase in the presence of ribonucleotide triphosphates and cap analogs in accordance with conventional techniques. However, the RNA may also be synthesized intracellularly after introduction of the cDNA.

The Girdwood S.A. and TR339 cDNA clones and the infectious RNAs and infectious virus particles produced therefrom of the present invention are useful for the preparation of pharmaceutical formulations, such as vaccines. In addition, the cDNA clones, infectious RNAs, and infectious viral particles of the present invention are useful for administration to animals for the purpose of producing antibodies to the Girdwood S.A. virus or the Sindbis virus strain TR339, which antibodies may be collected and used in known diagnostic techniques for the detection of Girdwood S.A. virus or Sindbis virus strain TR339. Antibodies can also be generated to the viral proteins expressed from the cDNAs disclosed herein. As another aspect of the present invention, the claimed cDNA clones are useful as nucleotide probes to detect the presence of Girdwood S.A. or TR339 genomic RNA or transcripts.

III. Infectious Virus Particles and Pharmaceutical Formulations

The infectious virus particles of the present invention include those containing double promoter vectors and those containing replicon vectors as described hereinabove. Alternately, the infectious virus particles contain infectious RNAs encoding the Girdwood S.A. or TR339 genome. When the infectious RNA comprises the Girdwood S.A. genome, preferably the RNA has the sequence encoded by the cDNA given as SEQ ID NO:4. When the infectious RNA comprises the TR339 genome, preferably the RNA has the sequence encoded by the cDNA given as SEQ ID NO:8.

The infectious, alphavirus particles of the present invention may be prepared according to the methods disclosed herein in combination with techniques known to those skilled in the art. These methods include transfecting an alphavirus-permissive cell with a replicon RNA including the alphavirus packaging segment and an inserted heterologous RNA, a first helper RNA including RNA encoding at least one alphavirus structural protein, and a second helper RNA including RNA encoding at least one alphavirus structural protein which is different from that encoded by the first helper RNA. Alternately, and preferably, at least one of the helper RNAs is produced from a cDNA encoding the helper RNA and operably associated with an appropriate promoter, the cDNA being stably transfected and integrated into the cells. More preferably, all of the helper RNAs will be "launched" from stably transfected cDNAs. The step of transfecting the alphavirus-permissive cell can be carried out according to any suitable means known to those skilled in the art, as described above with respect to propagation-competent viruses.

Uptake of propagation-competent RNA into the cells in vitro can be carried out according to any suitable means known to those skilled in the art. Uptake of RNA into the cells can be achieved, for example, by treating the cells with DEAE-dextran, treating the RNA with LIPOFECTIN® before addition to the cells, or by electroporation, with electroporation being the currently preferred means. These techniques are well known in the art. See e.g., U.S. Pat. No. 5,185,440 to Davis et al., and PCT Publication No. WO 92/10578 to Bioption AB, the disclosures of which are incorporated herein by reference in their entirety. Uptake of propagation-competent RNA into the cell in vivo can be carried out by administering the infectious RNA to a subject as described in Section I above.

The infectious RNAs may also contain a heterologous RNA segment, where the heterologous RNA segment contains a heterologous RNA and a promoter operably associated therewith. It is preferred that the infectious RNA introduces and expresses the heterologous RNA in bone marrow cells as described in Section I above. According to this embodiment, it is preferable that the promoter operatively associated with the heterologous RNA is operable in bone marrow cells. The heterologous RNA may encode any protein or peptide, preferably an immunogenic protein or peptide, a therapeutic protein or peptide, a hormone, a growth factor, an interleukin, a cytokine, a chemokine, an enzyme, a ribozyme, or an antisense oligonucleotide as described in more detail in Section I above.

The step of facilitating the production of the infectious viral particles in the cells may be carried out using conventional techniques. See e.g., U.S. Pat. No. 5,185,440 to Davis et al., PCT Publication No. WO 92/10578 to Bioption AB, and U.S. Pat. No. 4,650,764 to Temin et al. (although Temin et al., relates to retroviruses rather than alphaviruses). The infectious viral particles may be produced by standard cell culture growth techniques.

The step of collecting the infectious virus particles may also be carried out using conventional techniques. For example, the infectious particles may be collected by cell lysis, or collection of the supernatant of the cell culture, as is known in the art. See e.g., U.S. Pat. No. 5,185,440 to Davis et al., PCT Publication No. WO 92/10578 to Bioption AB, and U.S. Pat. No. 4,650,764 to Temin et al. Other suitable techniques will be known to those skilled in the art. Optionally, the collected infectious virus particles may be purified if desired. Suitable purification techniques are well known to those skilled in the art.

Pharmaceutical formulations, such as vaccines, of the present invention comprise an immunogenic amount of the infectious, virus particles in combination with a pharmaceutically acceptable carrier. An "immunogenic amount" is an amount of the infectious virus particles which is sufficient to evoke an immune response in the subject to which the pharmaceutical formulation is administered. An amount of from about $10^3$ to about $10^7$ particles, and preferably about $10^4$ to $10^6$ particles per dose is believed suitable, depending upon the age and species of the subject being treated, and the immunogen against which the immune response is desired.

Pharmaceutical formulations of the present invention for therapeutic use comprise a therapeutic amount of the infectious virus particles in combination with a pharmaceutically acceptable carrier. A "therapeutic amount" is an amount of the infectious virus particles which is sufficient to produce a therapeutic effect (e.g., triggering an immune response or supplying a protein to a subject in need thereof) in the subject to which the pharmaceutical formulation is administered. The therapeutic amount will depend upon the age and species of the subject being treated, and the therapeutic protein or peptide being administered. Typical dosages are an amount from about $10^1$ to about $10^5$ infectious units.

Exemplary pharmaceutically acceptable carriers include, but are not limited to, sterile pyrogen-free water and sterile pyrogen-free physiological saline solution. Subjects which may be administered immunogenic amounts of the infectious virus particles of the present invention include but are not limited to human and animal (e.g., pig, cattle, dog, horse, donkey, mouse, hamster, monkeys) subjects.

Pharmaceutical formulations of the present invention include those suitable for parenteral (e.g., subcutaneous, intracerebral, intradermal, intramuscular, intravenous and intraarticular) administration. Alternatively, pharmaceutical formulations of the present invention may be suitable for administration to the mucus membranes of a subject (e.g., intranasal administration by use of a dropper, swab, or inhaler). The formulations may be conveniently prepared in unit dosage form and may be prepared by any of the methods well known in the art.

The following examples are provided to illustrate the present invention, and should not be construed as limiting thereof. In these examples, PBS means phosphate buffered saline, EDTA means ethylene diamine tetraacetate, ml means milliliter, $\mu$l means microliter, mM means millimolar, $\mu$M means micromolar, u means unit, PFU means plaque forming units, g means gram, mg means milligram, $\mu$g means microgram, cpm means counts per minute, ic means intracerebral or intracerebrally, ip means intraperitoneal or intraperitoneally, iv means intravenous or intravenously, and sc means subcutaneous or subcutaneously.

Amino acid sequences disclosed herein are presented in the amino to carboxyl direction, from left to right. The amino and carboxyl groups are not presented in the sequence. Nucleotide sequences are presented herein by single strand only in the 5' to 3' direction, from left to right. Nucleotides and amino acids are represented herein in the manner recommended by the IUPAC-IUB Biochemical Nomenclature Commission, or (for amino acids) by either one letter or three letter code, in accordance with 37 CFR § 1.822 and established usage. Where one letter amino acid code is used, the same sequence is also presented elsewhere in three letter code.

EXAMPLE 1

Cells and Virus Stocks

S.A.AR86 was isolated in 1954 from a pool of Culex sp. mosquitoes collected near Johannesburg, South Africa. Weinbren et al., *S. Afr. Med. J.* 30, 631–36 (1956). Ockelbo82 was isolated from Culiseta sp. mosquitoes collected in Edsbyn, Sweden in 1982 and was associated serologically with human disease. Niklasson et al., *Am. J. Trop. Med. Hyg.* 33, 1212–17 (1984). Girdwood S.A. was isolated from a human patient in the Johannesburg area of South Africa in 1963. Malherbe et al., *S. Afr. Med. J.* 37, 547–52 (1963). Molecularly cloned virus TR339 represents the deduced consensus sequence of Sindbis AR339. McKnight et al., *J. Virol.* 70, 1981–89 (1996); William Klimstra, personal communication. TRSB is a laboratory strain of Sindbis isolate AR339 derived from a cDNA clone pTRSB and differing from the AR339 consensus sequence at three codons. McKnight et al., *J. Virol.* 70, 1981–89 (1996). pTR5000 is a full-length cDNA clone of Sindbis AR339 following the SP6 phage promoter and containing mostly Sindbis AR339 sequences.

Stocks of all molecularly cloned viruses were prepared by electroporating genome length in vitro transcripts of their respective cDNA clones in BHK-21 cells. Heidner et al., *J. Virol.* 68, 2683–92 (1994). Girdwood S.A. (Malherbe et al., *S. Afr. Med. J.* 37, 547–52 (1963)) and Ockelbo82 (Espmark and Niklasson, *Am. J. Trop. Med. Hyg.* 33, 1203–11 (1984); Niklasson et al., *Am. J. Trop. Med. Hyg.* 33, 1212–17 (1984)) were passed one to three times in BHK-21 cells in order to produce amplified stocks of virus. All virus stocks were stored at −70° C. until needed. The titers of the virus stocks were determined on BHK-21 cells from aliquots of frozen virus.

EXAMPLE 2

Cloning the S.A.AR86 and Girdwood S.A. Genomic Sequences

The sequences of S.A.AR86 (SEQ ID NO: 1) and Girdwood S.A. (SEQ ID NO:4) were determined from uncloned reverse transcriptase-polymerase chain reaction (RT-PCR) fragments amplified from virion RNA. Heidner et al., *J. Virol.* 68, 2683–92 (1994). The sequence of the 5' 40 nucleotides was determined by directly sequencing the genomic RNA. Sanger et al., *Proc. Natl. Acad. Sci. USA* 74, 5463–67 (1977); Zimmern and Kaesberg, *Proc. Natl. Acad. Sci. USA* 75, 4257–61 (1978); Ahlquist et al., *Cell* 23, 183–89 (1981).

The S.A.AR86 genome was 11,663 nucleotides in length, excluding the 5' CAP and 3' poly(A) tail, 40 nucleotides shorter than the alphavirus prototype Sindbis strain AR339. Strauss et al., *Virology* 133, 92–110 (1984). Compared with the consensus sequence of Sindbis virus AR339 (McKnight et al., *J. Virol.* 70 1981–89 (1996)), S.A.AR86 contained two separate 6-nucleotide insertions, and one 3-nucleotide insertion in the 3' half of the nsP3 gene, a region not well conserved among alphaviruses. The two 6-nucleotide insertions were found immediately 3' of nucleotides 5403 and 5450, and the 3-nucleotide insertion was immediately 3' of nucleotide 5546 compared with the AR339 genome. In addition, S.A.AR86 contained a 54-nucleotide deletion in nsP3 which spanned nucleotides 5256 to 5311 of AR339. As a result of these deletions and insertions, S.A.AR86 nsP3 was 13 amino acids smaller than AR339, containing an 18-amino acid deletion and a total of 5 amino acids inserted. The 3' untranslated region of S.A.AR86 contained, with respect to AR339, two 1-nucleotide deletions at nucleotides 11,513 and 11,602, and one 1-nucleotide insertion following nucleotide 11,664. The total numbers of nucleotides and predicted amino acids comprising the remaining genes of S.A.AR86 were identical to those of AR339.

The cDNA sequence of S.A.AR86 is presented in SEQ ID NO:1. Nucleotides 1 through 59 represent the 5' UTR, the non-structural polyprotein is encoded by nucleotides 60 through 7559 (nsP1-nt60 through nt1679; nsP2-nt1680 through nt4099; nsP3-nt4100 through nt5729; nsP4-nt5730 through nt7559), the structural polyprotein is encoded by nucleotides 7608 through 11342 (capsid-nt7608 through nt8399; E3-nt8400 through nt8591; E2-nt8592 through nt9860; 6K-nt9861 through nt10025; E1-nt10026 through nt11342), and the 3' UTR is represented by nucleotides 11346 through 11663.

A notable feature of the deduced amino acid sequence of S.A.AR86 (SEQ ID NO:2 and SEQ ID NO:3) was the cysteine codon in place of an opal termination codon between nsP3 and nsP4. S.A.AR86 is the only alphavirus of the Sindbis group, and one of just three alphavirus isolates sequenced to date, which do not contain an opal termination codon between nsP3 and nsP4. Takkinen, K., *Nucleic Acids Res.* 14, 5667–5682 (1986); Strauss et al., *Virology* 164, 265–74 (1988).

The genome of Girdwood S.A. was 11,717 nucleotides long excluding the 5' CAP and 3' poly(A) tail. The nucleotide sequence (SEQ ID NO:4) of the Girdwood S.A. genome and the putative amino acid sequence (SEQ ID NO:5 and SEQ ID NO:6) of the Girdwood S.A. gene products are shown in the accompanying sequence listings. The asterisk at nucleotides 5763 to 5765 in SEQ ID NO:5 indicates the position of the opal termination codon in the coding region of the nonstructural polyprotein. The extra nucleotides relative to AR339 were in the nonconserved half of nsP3, which contained insertions totalling 15 nucleotides, and in the 3' untranslated region which contained two 1-nucleotide deletions and a 1-nucleotide insertion with respect to the consensus Sindbis AR339 genome. The insertions found in the nsP3 gene of Girdwood S.A. were identical in position and content to those found in S.A.AR86, although Girdwood S.A. did not have the large nsP3 deletion characteristic of S.A.AR86. The remaining portions of the genome contained the same number of nucleotides and predicted amino acids as Sindbis AR339.

The cDNA sequence of Girdwood S.A. is presented in SEQ ID NO:4. An "N" in the sequence indicates that the identity of the nucleotide at that position is unknown. Nucleotides 1 through 59 represent the 5' UTR, the non-structural polyprotein is encoded by nucleotides 60 through 7613 (nsP1-nt60 through nt1679; nsP2-nt1680 through nt4099; nsP3-nt4100 through nt5762 or nt5783; nsP4-nt5784 through nt7613), the structural polyprotein is encoded by nucleotides 7662 through 11396 (capsid-nt7662 through nt8453; E3-nt8454 through nt8645; E2-nt8646 through nt9914, 6K-9915 through nt10079; E1-nt10080 through nt11396), and the 3' UTR is represented by nucleotides 11400 through 11717. There is an opal termination codon at nucleotides 5763 through 5765.

Overall, Girdwood S.A. was 94.5% identical to the consensus Sindbis AR339 sequence, differing at 655 nucleotides not including the insertions and deletions. These nucleotide differences resulted in 88 predicted amino acid changes or a difference of 2.3%. A plurality of amino acid differences were concentrated in the nsP3 gene, which contained 32 of the amino acid changes, 25 of which were in the nonconserved 3' half.

The Girdwood S.A. nucleotides at positions 1, 3, and 11,717 could not be resolved. Because the primer used during the RT-PCR amplification of the 3' end of the genome assumed a cytosine in the 3' terminal position, the identity of this nucleotide could not be determined with certainty. However, in all alphaviruses sequenced to date there is a cytosine in this position. This, combined with the fact that no difficulty was encountered in obtaining RT-PCR product for this region with an oligo(dT) primer ending with a 3'G, suggested that Girdwood S.A. also contains a cytosine at this position. The ambiguity at nucleotide positions 1 and 3 resulted from strong stops encountered during the RNA sequencing.

EXAMPLE 3

Comparison of S.A.AR86 and Girdwood S.A. Sequences With Other Sindbis-Related Virus Sequences Table 1 examines the relationship of S.A.AR86 and Girdwood S.A. to each other and to other Sindbis-related viruses. This was accomplished by aligning the nucleotide and deduced amino acid sequences of Ockelbo82, AR339 and Girdwood S.A. to those of S.A.AR86 and then calculating the percentage identity for each gene using the programs contained within the Wisconsin GCG package (Genetics Computer Group, 575 Science Drive, Madison Wis. 53711), as described in more detail in McKnight et al., J. Virol. 70, 1981–89 (1996).

The analysis suggests that S.A.AR86 is most similar to the other South African isolate, Girdwood S.A., and that the South African isolates are more similar to the Swedish Ockelbo82 isolate than to the Egyptian Sindbis AR339 isolate. These results also suggest that it is unlikely that S.A.AR86 is a recombinant virus like WEE virus. Hahn et al., Proc. Natl. Acad. Sci. USA 85, 5997–6001 (1988).

TABLE 1

Comparison of the Nucleotide and Amino Add Sequences of S.A.AR86 Virus with Those of Sindbis AR339, Ockelbo82, and Girdwood S.A. Viruses[a]

|  | Nucleotide Differences[b] | | | Amino Acid Differences[b] | | |
| --- | --- | --- | --- | --- | --- | --- |
| Regions | AR339 | OCK82 Number (%) | GIRD | AR339 | OCK82 Number (%) | GIRD |
| 5' untranslated | 0 (0.0) | 0 (0.0) | 1 (1.7) | — | — | — |
| nsP1 | 76 (4.7) | 37 (2.3) | 15 (0.9) | 9 (1.7) | 6 (1.1) | 2 (0.4) |
| nsP2 | 137 (5.7) | 86 (3.6) | 45 (1.9) | 15 (1.9) | 8 (1.0) | 12 (1.5) |
| nsP3 | | | | | | |
| Conserved[c] | 51 (5.7) | 35 (3.9) | 13 (1.6) | 6 (2.0) | 1 (0.3) | 1 (0.4) |
| Nonconserved[d] | 116 (6.6) | 83 (4.4) | 70 (2.2) | 45 (9.7) | 34 (7.0) | 27 (3.7) |
| nsP4 | 111 (6.1) | 68 (3.7) | 19 (1.1) | 8 (1.3) | 2 (0.3) | 4 (0.6) |
| 26s junction | 1 (2.1) | 0 (0.0) | 1 (2.1) | — | — | — |
| Capsid | 36 (4.5) | 26 (3.3) | 7 (0.9) | 1 (0.4) | 3 (1.1) | 0 (0.0) |
| E3 | 17 (8.9) | 5 (2.6) | 4 (2.1) | 1 (1.6) | 0 (0.0) | 0 (0.0) |
| E2 | 71 (5.6) | 43 (3.4) | 18 (1.4) | 12 (2.6) | 6 (1.4) | 2 (0.5) |
| 6K | 10 (6.1) | 9 (5.4) | 4 (2.4) | 2 (3.6) | 2 (3.6) | 1 (1.8) |
| E1 | 49 (3.7) | 31 (2.3) | 16 (1.2) | 7 (1.6) | 6 (1.4) | 2 (0.9) |
| 3' untranslated | 14 (4.5) | 8 (2.5) | 1 (0.3) | — | — | — |
| Totals | 689 (5.5) | 431 (3.3) | 214 (1.4) | 106 (2.3) | 68 (1.4) | 51 (0.9) |

[a]All nucleotide positions and gene boundaries are numbered according to those used for the Sindbis AR339, $HR_{sp}$ variant Genebank Accession No. J02363; Strauss et al., Virology 133, 92–110 (1984).
[b]Differences include insertions and deletions.
[c]Conserved region nucleotides 4100 to 5000 (aa 1 to aa300).
[d]Nonconserved region nucleotides 5001 to 5729 (aa301 to aa542, S.A.AR86 numbering).

EXAMPLE 4

Neurovirulence of S.A.AR86 and Girdwood S.A.

Girdwood S.A., Ockelbo82, and S.A.AR86 are related by sequence; in contrast, it has previously been reported that only S.A.AR86 displayed the adult mouse neurovirulence phenotype. Russell et al., J. Virol. 63, 1619–29 (1989). These findings were confirmed by the present investigations. Briefly, groups of four female CD-1 mice (3–6 weeks of age) were inoculated ic with $10^3$ plaque-forming units (PFU) of S.A.AR86, Girdwood S.A., or Ockelbo82. Neither Girdwood S.A. nor Ockelbo82 infection produced any clinical signs of infection. Infection with S.A.AR86 produced neurological signs within four to five days and ultimately killed 100% of the mice as previously demonstrated.

Table 2 lists those amino acids of S.A.AR86 which might explain the neurovirulence phenotype in adult mice. A position was scored as potentially related to the S.A.AR86 adult neurovirulence phenotype if the S.A.AR86 amino acid differed from that which otherwise was absolutely conserved at that position in the other viruses.

TABLE 2

Divergent Amino Acids in S.A.AR86
Potentially Related to the Adult Neurovirulence Phenotype

|       | Position in S.A.AR86 | S.A.AR86 Amino Acid | Conserved Amino Acid |
|-------|----------------------|---------------------|----------------------|
| nsP1  | 583                  | Thr                 | Ile                  |
| nsP2  | 256                  | Arg                 | Ala                  |
|       | 648                  | Ile                 | Val                  |
|       | 651                  | Lys                 | Glu                  |
| nsP3  | 344                  | Gly                 | Glu                  |
|       | 386                  | Tyr                 | Ser                  |
|       | 441                  | Asp                 | Gly                  |
|       | 445                  | Ile                 | Met                  |
|       | 537                  | Cys                 | Opal                 |
| E2    | 243                  | Ser                 | Leu                  |
| 6K    | 30                   | Val                 | Ile                  |
| E1    | 112                  | Val                 | Ala                  |
|       | 169                  | Leu                 | Ser                  |

EXAMPLE 5 pS55 Molecular Clone of S.A.AR86

As a first step in investigating the unique adult mouse neurovirulence phenotype of S.A.AR86, a full-length cDNA clone of the S.A.AR86 genome was constructed. The sources of cDNA included conventional cDNA clones (Davis et al., Virology 171, 189–204 (1989)) as well as uncloned RT-PCR fragments derived from the S.A.AR86 genome. As described previously, these were substituted, starting at the 3' end, into pTR5000 (McKnight et al., J. Virol. 70, 1981–89 (1996)), a full-length Sindbis clone from which infectious genomic replicas could be derived by transcription with SP6 polymerase in vitro.

The end result was pS55, a molecular clone of S.A.AR86 from which infectious transcripts could be produced and which contained four nucleotide changes (G for A at nt 215; G for C at nt 3863; G for A at nt 5984; and C for T at nt 9113) but no amino acid coding differences with respect to the S.A.AR86 genenomic RNA (amino acid sequence of S.A.AR86 presented in SEQ ID NO:2 and SEQ ID NO:3. The nucleotide sequence of clone pS55 is presented in SEQ ID NO:7.

As has been described by Simpson et al., Virology 222, 464–69 (1996), neurovirulence and replication of the virus derived from pS55 (S55) were compared with those of S.A.AR86. It was found that S55 exhibits the distinctive adult neurovirulence characteristic of S.A.AR86. Like S.A.AR86, S55 produces 100% mortality in adult mice infected with the virus and the survival times of animals infected with both viruses were indistinguishable. In addition, S55 and S.A.AR86 were found to replicate to essentially equivalent titers in vivo, and the profiles of S55 and S.A.AR86 virus growth in the central nervous system and periphery were very similar.

From these data it was concluded that the silent changes found in virus derived from clone pS55 had little or no effect on its growth or virulence, and that this molecularly cloned virus accurately represents the biological isolate, S.A.AR86.

EXAMPLE 6

Construction of the Consensus AR339 Virus TR339

The consensus sequence of the Sindbis virus AR339 isolate, the prototype alphavirus was deduced. The consensus AR339 sequence was inferred by comparison of the TRSB sequence (a laboratory-derived AR339 strain) with the complete or partial sequences of $HR_{sp}$ (the Gen Bank sequence; Strauss et al., Virology 133, 92–110 (1984)), SV1A, and NSV (AR339-derived laboratory strains; Lustig et al., J. Virol 62, 2329–36 (1988)), and SIN (a laboratory-derived AR339 strain; Davis et al., Virology 161, 101–108 (1987), Strauss et al., J. Virol. 65, 4654–64 (1991)). Each of these viruses was descended from AR339. Where these sequences differed from each other, they also were compared with the amino acid sequences of other viruses related to Sindbis virus: Ockelbo82, S.A.AR86, Girdwood S.A., and the somewhat more distantly related Aura virus. Rumenapf et al., Virology 208, 621–33 (1995).

The details of determining a consensus AR339 sequence and constructing the consensus virus TR339 have been described elsewhere. McKnight et al., J. Virol. 70, 1981–89 (1996); Klimstra et al., manuscript in preparation. The nucleotide sequence of pTR339 is presented in SEQ ID NO:8. The deduced amino acid sequences of the pTR339 non-structural and structural polyproteins are shown as SEQ ID NO:9 and SEQ ID NO:10, respectively. Referring to SEQ ID NO:8, nucleotides 1 through 59 represent the 5' UTR, the non-structural polyprotein is encoded by nucleotides 60 through 7598 (nsP1-nt60 through nt11679; nsP2-nt1680 through nt4099; nsP3-nt4100 through nt5747 or 5768; nsP4-nt5769 through nt7598), the structural polyprotein is encoded by nucleotides 7647 through 11381 (capsid-nt7647 through nt8438; E3-nt8439 through nt8630; E2-nt8631 through nt9899; 6K-nt9900 through nt10064; E1-nt10065 through nt11381), and the 3' UTR is represented by nucleotides 11382 through 11703. There is an opal termination codon at nucleotides 5748 through 5750. The asterisk at nucleotides 5748 to 5750 in SEQ ID NO:9 indicates the position of the opal termination codon in the coding region of the nonstructural polyprotein. The consensus nucleotide sequence diverged from the pTRSB sequence at three coding positions (nsP3 528, E2 1, and E1 72). These differences are illustrated in Table 3.

TABLE 3

Amino Acid Differences Between
Laboratory Strain TRSB and Molecular Clone TR339

|       | nsP3 528 (nt5683) | E2 1 (nt8633) | E1 72 (nt10279) |
|-------|-------------------|---------------|------------------|
| TR339 | Arg (CGA)         | Ser (AGC)     | Ala (GCU)        |
| TRSB  | Gln (CAA)         | Arg (AGA)     | Val (GUU)        |

EXAMPLE 7

Animals Used for In Vivo Localization Studies

Specific pathogen free CD-1 mice were obtained from Charles River Breeding Laboratories (Raleigh, N.C.) at 21 days of age and maintained under barrier conditions until approximately 37 days of age. Intracerebral (ic) inoculations were performed as previously described, Simpson et al., Virol. 222, 464–49 (1996), with 500 PFU of S51 (an attenuated mutant of S55) or $10^3$ PFU of S55. Animals inoculated peripherally were first anesthetized with METOFANE®. Then, 25 µl of diluent (PBS, pH 7.2, 1% donor calf serum, 100 u/ml penicillin, 50 µg/ml streptomycin, 0.9 mM $CaCl_2$, and 0.5 mM $MgCl_2$) containing $10^3$ PFU of virus were injected either intravenously (iv) into the tail vein, subcutaneously (sc) into the skin above the shoulder blades on the middle of the back, or intraperitoneally (ip) in the lower right abdomen. Animals were sacrificed at various times post-inoculation as previously described. Simpson et al., *Virol.* 222, 464–49 (1996). Brains (including brainstems) were homogenized in diluent to 30% w/v, and right quadriceps were homogenized in diluent to 25% w/v. Homogenates were handled and titered as described previously. Simpson et al., *Virol.* 222, 464–49 (1996). Bone marrow was harvested by crushing both femurs from each animal in sufficient diluent to produce a 30% w/v suspension (calculated as weight of uncrushed femurs in volume of diluent). Samples were stored at −70° C. For titration, samples were thawed and clarified by centrifugation at 1,000×g for 20 minutes at 4° C. before being titered by conventional plaque assay on BHK-21 cells.

EXAMPLE 8

Tissue Preparation for In Situ Hybridization Studies

Animals were anesthetized by ip injection of 0.5 ml AVERTIN® at various times post-inoculation followed by perfusion with 60 to 75 ml of 4% paraformaldehyde in PBS (pH 7.2) at a flow rate of 10 ml per minute. The entire carcass was decalcified for 8 to 10 weeks in 4% parafomaldehyde containing 8% EDTA in PBS (pH 6.8) at 4° C. This solution was changed twice during the decalcification period. Selected tissues were cut into blocks approximately 3 mm thick and placed into biopsy cassettes for paraffin embedding and sectioning. Blocks were embedded, sectioned and hematoxylinfeosin stained by Experimental Pathology Laboratories (Research Triangle Park, N.C.) or North Carolina State University Veterinary School Pathology Laboratory (Raleigh, N.C.).

EXAMPLE 9

In Situ Hybridization

Hybridizations were performed using a [$^{35}$S]-UTP labeled S.A.AR86 specific riboprobe derived from pDS-45. Clone pDS-45 was constructed by first amplifying a 707 base pair fragment from pS55 by PCR using primers 7241 (5'-CTGCGGCGGATTCATCTTGC-3', SEQ ID NO:11) and SC-3 (5'-CTCCAACTTAAGTG-3', SEQ ID NO:12). The resulting 707 base pair fragment was purified using a GENE CLEAN® kit (Bio101, CA), digested with HhaI, and cloned into the SmaI site of pSP72 (Promega). Linearizing pDS-45 with EcoRV and performing an in vitro transcription reaction with SP6 DNA-dependent, RNA polymerase (Promega) in the presence of [$^{35}$S]-UTP resulted in a riboprobe approximately 500 nucleotides in length of which 445 nucleotides were complementary to the S.A.AR86 genome (nucleotides 7371 through 7816). A riboprobe specific for the influenza strain PR-8 hemagglutinin (HA) gene was used as a control probe to test non-specific binding. The in situ hybridizations were performed as described previously (Charles et al., *Virol.* 208, 662–71 (1995)) using 10$^5$ cpm of probe per slide.

EXAMPLE 10

Replication of S.A.AR86 in Bone Marrow

Three groups of six adult mice each were inoculated peripherally (sc, ip, or iv) with 1200 PFU of S55 (a molecular clone of S.A.AR86) in 25 µl of diluent. Under these conditions, the infection produced no morbidity or mortality. Two mice from each group were anesthetized and sacrificed at 2, 4 and 6 days post-inoculation by exsanguination. The serum, brain (including brainstem), right quadricep, and both femurs were harvested and titered by plaque assay. Virus was never detected in the quadricep samples of animals inoculated sc (Table 4). A single animal inoculated ip (two days post-inoculation) and two mice inoculated iv (at four and six days post-inoculation) had detectable virus in the right quadricep, but the titer was at or just above the limit of detection (6.25 PFU/g tissue). Virus was present sporadically or at low levels in the brain and serum of animals regardless of the route of inoculation. Virus was detected in the bone marrow of animals regardless of the route of inoculation. However, the presence of virus in bone marrow of animals inoculated sc or ip was more sporadic than animals inoculated iv, where five out of six animals had detectable virus. These results suggest that S55 targets to the bone marrow, especially following iv inoculation.

The level and frequency of virus detected in the serum and muscle suggested that virus detected in the bone marrow was not residual virus contamination from blood or connective tissue remaining in bone marrow samples. The following experiment also suggested that virus in bone marrow was not due to tissue or serum contamination. Mice were inoculated ic with 1200 PFU of S55 in 25 µl of diluent. Animals were sacrificed at 0.25, 0.5, 1, 1.5, 2, 3, 4, 5, and 6 days post-inoculation, and the carcasses were decalcified as described in Example 8. Coronal sections taken at approximately 3 mm intervals through the head, spine (including shoulder area), and hips were probed with an S55-specific [$^{35}$S]-UTP labeled riboprobe derived from pDS-45. Positive in situ hybridization signal was detected by one day post-inoculation in the bone marrow of the skull (data not shown). Weak signal also was present in some of the chondrocytes of the vertebrae, suggesting that S55 was replicating in these cells as well. Although the frequency of positive bone marrow cells was low, the signal was very intense over individual positive cells. This result strongly suggests that S55 replicates in vivo in a subset of cells contained in the bone marrow.

EXAMPLE 11

Other Sindbis Group Viruses

It was of interest to determine if the ability to replicate in the bone marrow of mice was unique to S55 or was a general feature of other viruses, both Sindbis and non-Sindbis viruses, in the Sindbis group. Six 38-day-old female CD-1 mice were inoculated iv with 25 µl of diluent containing 10$^3$ PFU of S55, Ockelbo82, Girdwood S.A., TR339, or TRSB. At 2, 4 and 6 days post-inoculation two mice from each group were sacrificed and whole blood, serum, brain (including brainstem), right quadricep, and both femurs were harvested for virus titration.

The results of this experiment were similar to those with S55. TRSB infected animals had no virus detectable in serum or whole blood in any animal at any time, and with the other viruses tested, no virus was detected in the serum or whole blood of any animal beyond two days post-inoculation (detection limit, 25 PFU/ml). Neither TRSB nor TR339 was detectable in the brains of infected animals at any time post-inoculation. S55, Girdwood S.A., and Ockelbo82 were present in the brains of infected animals sporadically with the titers being at or near the 75 PFU/g level of detection. All the tested viruses were found sporadically at or slightly above the 50 PFU/g detection limit in the right quadricep of infected animals except for a single animal four days post-inoculation with TRSB which had nearly $10^5$ PFU/g of virus in its quadricep.

The frequency at which the different viruses were detected in bone marrow varied widely, with S55 and Girdwood S.A. being the most frequently isolated (five out of six animals) and Ockelbo82 and TRSB being the least frequently isolated from bone marrow (one out of six animals and two out of six animals, respectively) (Table 4). Girdwood S.A. and S55 gave nearly identical profiles in all tissues. Girdwood S.A., unlike S.A.AR86, is not neurovirulent in adult mice (Example 4), suggesting that the adult neurovirulence phenotype is distinct from the ability of the virus to replicate efficiently in bone marrow.

S51 differs from S55 by a threonine for isoleucine substitution at amino acid residue 538 of nsP1 and is attenuated in adult mice inoculated intracerebrally. Like S55, S51 targeted to and replicated in the bone marrow of 37-day-old female CD-1 mice following ic inoculation. Mice were inoculated ic with 500 PFU of S51 and sacrificed at 4, 8, 16, and 30 days post-inoculation for determination of bone marrow and serum titers. At no time post-inoculation was virus detected in the serum above the 6.25 PFU/ml detection limit. Virus was detectable in the bone marrow samples of both animals sampled at four days post-inoculation and in one animal eight days post-inoculation (Table 5). No virus was detectable by sitration on BHK-21 cells in any of the bone marrow samples beyond eight days post-inoculation. These results suggested that the attenuating mutation present in S51, which reduces the neurovirulence of the virus, did not impair acute viral replication in the bone marrow.

It was notable that the plaque size on BHK-21 cells of virus recovered on day 4 post-inoculation was smaller than the size of plaques produced by the inoculum virus, and that plaques produced from virus recovered from the day 8 post-inoculation samples were even smaller and barely visible. This suggests a strong selective pressure in the bone marrow for virus that is much less efficient in forming plaques on BHK-21 cells.

TABLE 4

Titers Following IV Inoculation of Virus

| Virus | Animal | Days Post-Inoculation | Bone Marrow (PFU/g) | Serum (PFU/ml) | Blood (PFU/ml) | Brain (PFU/g) | Quadricep (PFU/g) |
|---|---|---|---|---|---|---|---|
| S55 | A | 2 | 1125 | N.D.[a] | N.D. | N.D. | N.D. |
| | B | | 488 | 50 | 200 | N.D. | N.D. |
| | A | 4 | 863 | N.D. | N.D. | N.D. | 550 |
| | B | | 113 | N.D. | N.D. | 75 | N.D. |
| | A | 6 | N.D. | N..D. | N.D. | N.D. | 50 |
| | B | | 37.5 | N.D. | N.D. | N.D. | N.D. |
| | Limit of Detection | | 37.5 | 25 | 25 | 75 | 50 |
| TR339 | A | 2 | N.D. | N.D. | N.D. | N.D. | N.D. |
| | B | | 1500 | 75 | 700 | N.D. | N.D. |
| | A | 4 | 1050 | N.D. | N.D. | N.D. | N.D. |
| | B | | 1762 | N.D. | N.D. | N.D. | 400 |
| | A | 6 | N.D. | N.D. | N.D. | N.D. | N.D. |
| | B | | N.D. | N.D. | N.D. | N.D. | N.D. |
| | Limit of Detection | | 37.5 | 25 | 25 | 37.5 | 50 |
| TRSB | A | 2 | N.D. | N.D. | N.D. | N.D. | N.D. |
| | B | | N.D. | N.D. | N.D. | N.D. | N.D. |
| | A | 4 | 150 | N.D. | N.D. | N.D. | 1000 |
| | B | | N.D. | N.D. | N.D. | N.D. | 100000 |
| | A | 6 | N.D. | N.D. | N.D. | N.D. | N.D. |
| | B | | 37.5 | N.D. | N.D. | N.D. | N.D. |
| | Limit of Detection | | 37.5 | 25 | 25 | 37.5 | 50 |
| Girdwood S.A. | A | 2 | 22000 | 2325 | 1450 | 300 | 50 |
| | B | | 2500 | 1200 | 2600 | N.D. | N.D. |
| | A | 4 | 788 | N.D. | N.D. | N.D. | N.D. |
| | B | | 113 | N.D. | N.D. | 75 | N.D. |
| | A | 6 | N.D. | N.D. | N.D. | N.D. | N.D. |
| | B | | 75 | N.D. | N.D. | 1700 | N.D. |
| | Limit of Detection | | 37.5 | 25 | 25 | 75 | 50 |
| Ockelbo82 | A | 2 | N.D. | 125 | 150 | N.D. | N.D. |
| | B | | N.D. | 50 | 500 | N.D. | 200 |
| | A | 4 | N.D. | N.D. | N.D. | 300 | N.D. |
| | B | | 300 | N.D. | N.D. | N.D. | N.D. |
| | A | 6 | N.D. | N.D. | N.D. | 100000 | N.D. |
| | B | | N.D. | N.D. | N.D. | N.D. | N.D. |
| | Limit of Detection | | 37.5 | 25 | 25 | 75 | 50 |

[a]"N.D." indicates that the virus titers were below the limit of detection.

EXAMPLE 12

Virus Persistence in Bone Marrow

The next step in our investigations was to evaluate the possibility that S.A.AR86 persisted long-term in bone marrow. S51 is a molecularly cloned, attenuated mutant of S55.

To demonstrate that S51 virus genomes were present in bone marrow cells long after acute infection, four to six-week-old female CD-1 mice were inoculated ic with 500 PFU of S51. Three months post-inoculation two animals were sacrificed, perfused with paraformaldehyde and decalcified as described in Example 8. The heads and hind limbs from these animals were paraffin embedded, sectioned, and probed with a S.A.AR86 specific [$^{35}$S]-UTP labeled riboprobe derived from clone pDS-45. In situ hybridization signal was clearly present in discrete cells of the bone and bone marrow of the legs (data not shown). Furthermore, no in situ hybridization signal was detected in an adjacent control section probed with an influenza virus HA gene specific riboprobe. As the relative sensitivity of in situ hybridization is reduced in decalcified tissues (Peter Charles, personal communication), these cells likely contain a relatively high number of viral sequences, even at three months post-inoculation. No in situ hybridization signal was observed in mid-sagital sections of the heads with the S.A.AR86 specific probe, although focal lesions were observed in the brain indicative of the prior acute infection with S51.

TABLE 5

S51 Titers in Bone Marrow Following IC Inoculation of 500 PFU

| Days Post- | Titers (Total PFU/Animal) | | Limit of |
|---|---|---|---|
| Inoculation | Animal A | Animal B | Detection |
| 4 | 2100 | 380 | 62.5 |
| 8 | 62.5 | N.D.[a] | 62.5 |
| 16 | N.D. | N.D. | 62.5 |
| 30 | N.D. | N.D. | 62.5 |

[a]"N.D." indicates that the virus titers were below the limit of detection.

That which is claimed is:

1. A helper cell for expressing an infectious, propagation defective, TR339 virus particle, comprising, in a TR339-permissive cell:

(a) a first helper RNA encoding (i) at least one TR339 structural protein, and (ii) not encoding at least one other TR339 structural protein; and (b) a second helper RNA separate from said first helper RNA, said second helper RNA (i) not encoding said at least one TR339 structural protein encoded by said first helper RNA, and (ii) encoding said at least one other TR339 structural protein not encoded by said first helper RNA, and with all of said TR339 structural proteins encoded by said first and second helper RNAs assembling together into TR339 particles in said cell containing a replicon RNA;

and wherein a TR339 packaging segment is deleted from at least said first helper RNA.

2. The helper cell according to claim 1 comprising no more than two helper RNAs.

3. The helper cell according to claim 1, wherein said first and second helper RNAs lack an alphavirus packaging segment.

4. The helper cell according to claim 1, wherein at least one of the helper RNAs comprises an attenuating mutation.

5. The helper cell according to claim 1, wherein the helper RNAs are expressed from cDNA introduced into said helper cell.

6. The helper cell according to claim 1, wherein said cDNA is stably integrated into said helper cell.

7. The helper cell according to claim 1, further containing a replicon RNA;

said replicon RNA encoding an alphavirus packaging segment and an inserted heterologous RNA;

and wherein said replicon RNA, said first helper RNA, and said second helper RNA are all separate molecules from one another.

8. The helper cell according to claim 7, wherein at least one of the helper RNAs or said replicon RNA comprises an attenuating mutation.

9. The helper cell according to claim 7, wherein the helper RNAs and said replicon RNA are expressed from cDNA introduced into said helper cell.

10. The helper cell according to claim 7, wherein said helper cell is transfected with RNAs comprising said replicon RNA and the helper RNAs.

11. The helper cell according to claim 7, wherein said heterologous RNA encodes an immunogenic protein or peptide.

12. The helper cell according to claim 7, wherein said heterologous nucleic acid encodes a therapeutic protein or peptide.

13. The helper cell according to claim 7, wherein said replicon RNA comprises two separate promoter sequences, each of which directs the expression of a different heterologous RNA sequence.

14. The helper cell according to claim 13, wherein said two separate promoter sequences are TR339 26S promoter sequences.

15. The helper cell according to claim 7, wherein said replicon RNA comprises a promoter sequence which directs the expression of a first heterologous RNA sequence and an IRES sequence upstream of a second heterologous RNA sequence.

16. The helper cell according to claim 7, wherein said replicon RNA comprises two different heterologous RNA sequences.

17. The helper cell according to claim 16, wherein said two different heterologous RNA sequences each encode an immunogenic protein or peptide which are different from each other.

18. The helper cell according to claim 1, further containing a replicon RNA;

said replicon RNA encoding an alphavirus packaging segment and an inserted heterologous RNA;

wherein said replicon RNA and said first helper RNA are separate molecules;

and wherein the molecule containing said replicon RNA further contains RNA encoding said at least one TR339 structural protein not encoded by said first helper RNA.

19. The helper cell according to claim 18, wherein at least one of the helper RNAs or said replicon RNA comprises an attenuating mutation.

20. The helper cell according to claim 18, wherein the helper RNAs and said replicon RNA are expressed from cDNA introduced into said helper cell.

21. The helper cell according to claim 18, wherein said helper cell is transfected with RNAs comprising said replicon RNA and the helper RNAs.

22. The helper cell according to claim 1, wherein said first helper RNA encodes both a TR339 E1 glycoprotein and a TR339 E2 glycoprotein, and wherein said second helper RNA encodes a TR339 capsid protein.

23. A method of making infectious, propagation defective, TR339 virus particles, comprising:

transfecting a TR339-permissive cell according to claim 1 with a propagation defective replicon RNA, said replicon RNA including an alphavirus packaging segment and an inserted heterologous RNA;

producing said TR339 virus particles in said transfected cell; and then collecting said TR339 virus particles from said cell.

24. Infectious TR339 virus particles produced by the method of claim 23.

25. A pharmaceutical formulation comprising infectious TR339 virus particles according to claim 24 in a pharmaceutically acceptable carrier.

26. The pharmaceutical formulation according to claim 25, wherein said infectious TR339 virus particles are included therein in an immunogenic amount.

27. Infectious TR339 virus particles containing a replicon RNA encoding a promoter, an inserted heterologous RNA, and wherein RNA encoding at least one TR339 structural protein is deleted therefrom so that said virus particle is propagation defective.

28. A recombinant DNA comprising a cDNA coding for a Sindbis strain TR339 RNA transcript and a heterologous promoter positioned upstream from said cDNA and operatively associated therewith.

29. An infectious RNA transcript encoded by a cDNA according to claim 28.

30. An infectious RNA according to claim 29, said infectious TR339 RNA transcript containing a heterologous RNA segment, said heterologous RNA segment comprising a promoter operably associated with a heterologous RNA.

31. Infectious viral particles containing an RNA transcript according to claim 29.

32. The recombinant DNA of claim 28 further comprising a heterologous DNA sequence.

33. A helper cell for expressing an infectious, propagation defective, alphavirus particle, comprising, in an alphavirus-permissive cell:

(a) a first helper RNA encoding (i) at least one alphavirus structural protein, and (ii) not encoding at least one other alphavirus structural protein;

(b) a second helper RNA separate from said first helper RNA, said second helper RNA (i) not encoding said at least one alphavirus structural protein encoded by said first helper RNA, and (ii) encoding said at least one other alphavirus structural protein not encoded by said first helper RNA; and (c) a TR339 replicon RNA, said TR339 replicon RNA encoding an alphavirus packaging segment and a heterologous RNA;
wherein an alphavirus packaging segment is absent from at least said first helper RNA;
and further wherein all of said alphavirus structural proteins encoded by the helper RNAs assemble together into alphavirus particles in said cell containing said TR339 replicon RNA.

34. The helper cell according to claim 33, wherein said TR339 replicon RNA, said first helper RNA, and said second helper RNA are all separate molecules from one another.

35. The helper cell according to claim 33, wherein said TR339 replicon RNA and said first helper RNA are separate molecules, and further wherein the molecule comprising said TR339 replicon RNA further comprises RNA encoding said at least one alphavirus structural protein not encoded by said first helper RNA.

36. A helper cell for expressing an infectious, propagation defective, alphavirus particle, comprising, in an alphavirus-permissive cell:

(a) a first helper RNA encoding (i) at least one TR339 structural protein, and (ii) not encoding at least one other TR339 structural protein;

(b) a second helper RNA separate from said first helper RNA, said second helper RNA (i) not encoding said at least one TR339 structural protein encoded by said first helper RNA, and (ii) encoding said at least one other TR339 structural protein not encoded by said first helper RNA; and (c) an alphavirus replicon RNA, said alphavirus replicon RNA encoding an alphavirus packaging segment and a heterologous RNA;

wherein an alphavirus packaging segment is absent from at least said first helper RNA;

and further wherein all of said TR339 structural proteins encoded by the helper RNAs assemble together into alphavirus particles in said cell containing said alphavirus replicon RNA.

37. The helper cell according to claim 36, wherein said alphavirus replicon RNA, said first helper RNA, and said second helper RNA are all separate molecules from one another.

38. The helper cell according to claim 36, wherein said alphavirus replicon RNA and said first helper RNA are separate molecules, and further wherein the molecule comprising said alphavirus replicon RNA further comprises RNA encoding said at least one TR339 structural protein not encoded by said first helper RNA.

39. A composition comprising infectious, propagation defective, virus particles, wherein each particle comprises a TR339 replicon RNA, and wherein the replicon RNA comprises an alphavirus packaging signal, one or more heterologous RNA sequences, and a sequence encoding at least one TR339 structural protein, and further wherein the replicon RNA lacks a sequence encoding at least one TR339 structural protein.

40. A pharmaceutical formulation comprising the composition according to claim 39 in a pharmaceutically-acceptable carrier.

41. The pharmaceutical formulation according to claim 40, wherein said composition is included therein in an immunogenic amount.

42. A composition comprising infectious, propagation defective, virus particles, wherein each particle comprises a TR339 nucleocapsid and an alphavirus replicon RNA, wherein the replicon RNA comprises an alphavirus packaging signal, one or more heterologous RNA sequences, and further wherein the replicon RNA lacks sequences encoding TR339 structural proteins.

43. The composition according to claim 42, wherein said alphavirus replicon RNA is from TR339.

44. A pharmaceutical formulation comprising the composition according to claim 42 in a pharmaceutically-acceptable carrier.

45. The pharmaceutical formulation according to claim 44, wherein said composition is included therein in an immunogenic amount.

46. A composition comprising infectious, propagation defective, virus particles, wherein each particle comprises an alphavirus nucleocapsid and a TR339 replicon RNA, wherein the TR339 replicon RNA comprises an alphavirus packaging signal, one or more heterologous RNA sequences, and further wherein the TR339 replicon RNA lacks sequences encoding alphavirus structural proteins.

47. A pharmaceutical formulation comprising the composition according to claim 46 in a pharmaceutically-acceptable carrier.

48. The pharmaceutical formulation according to claim 47, wherein said composition is included therein in an immunogenic amount.

49. A cDNA encoding a TR339 virus genome.

50. The cDNA of claim 49, wherein said cDNA has the sequence given as SEQ ID NO:8.

51. An RNA comprising a TR339 virus genome.

52. The RNA of claim 51, wherein said RNA has a sequence encoded by the cDNA of SEQ ID NO:8.

* * * * *

UNITED STATES PATENT AND TRADEMARK OFFICE
Certificate

Patent No. 6,008,035                                                                             Patented: December 28, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Robert E. Johnston, Chapel Hill, NC; Dennis A. Simpson, Pittsboro, NC; and William B. Klimstra, Shreveport, LA.

Signed and Sealed this Twenty-third Day of May 2006.

*ARDIN MARSCHEL, Ph. D.*
*Supervisory Patent Examiner*
Art Unit 1631

UNITED STATES PATENT AND TRADEMARK OFFICE
CERTIFICATE OF CORRECTION

| | |
|---|---|
| PATENT NO. | : 6,008,035 |
| APPLICATION NO. | : 09/102248 |
| DATED | : December 28, 1999 |
| INVENTOR(S) | : Johnston et al. |

It is certified that error appears in the above-identified patent and that said Letters Patent is hereby corrected as shown below:

In the Claims:

Column 141, line 1 (immediately following the Sequence Listing) through Column 146, end should read:

-- 1. A helper cell for expressing an infectious, propagation defective, TR339 virus particle, comprising, in a TR339-permissive cell:
 (a) a first helper RNA encoding *(i)* at least one TR339 structural protein, and *(ii)* not encoding at least one other TR339 structural protein; and
 (b) a second helper RNA separate from said first helper RNA, said second helper RNA *(i)* not encoding said at least one TR339 structural protein encoded by said first helper RNA, and *(ii)* encoding said at least one other TR339 structural protein not encoded by said first helper RNA, and with all of said TR339 structural proteins encoded by said first and second helper RNAs assembling together into TR339 particles in said cell containing a replicon RNA;
 and wherein a TR339 packaging segment is deleted from at least said first helper RNA.

2. The helper cell according to claim 1 comprising no more than two helper RNAs.

3. The helper cell according to claim 1, wherein said first and second helper RNAs lack an alphavirus packaging segment.

4. The helper cell according to claim 1, wherein at least one of the helper RNAs comprises an attenuating mutation.

5. The helper cell according to claim 1, wherein the helper RNAs are expressed from cDNA introduced into said helper cell.

6. The helper cell according to claim 5, wherein said cDNA is stably integrated into said helper cell.

7. The helper cell according to claim 1, further containing a TR339 replicon RNA;
 said replicon RNA encoding an alphavirus packaging segment and an inserted heterologous RNA;
 and wherein said replicon RNA, said first helper RNA, and said second helper RNA are all separate molecules from one another.

UNITED STATES PATENT AND TRADEMARK OFFICE
CERTIFICATE OF CORRECTION

| | |
|---|---|
| PATENT NO. | : 6,008,035 |
| APPLICATION NO. | : 09/102248 |
| DATED | : December 28, 1999 |
| INVENTOR(S) | : Johnston et al. |

It is certified that error appears in the above-identified patent and that said Letters Patent is hereby corrected as shown below:

8.     The helper cell according to claim 7, wherein at least one of the helper RNAs or said replicon RNA comprises an attenuating mutation.

9.     The helper cell according to claim 7, wherein the helper RNAs and said replicon RNA are expressed from cDNA introduced into said helper cell.

10.     The helper cell according to claim 7, wherein said helper cell is transfected with RNAs comprising said replicon RNA and the helper RNAs.

11.     The helper cell according to claim 7, wherein said heterologous RNA encodes an immunogenic protein or peptide.

12.     The helper cell according to claim 7, wherein said heterologous nucleic acid encodes a therapeutic protein or peptide.

13.     The helper cell according to claim 7, wherein said replicon RNA comprises two separate promoter sequences, each of which directs the expression of a different heterologous RNA sequence.

14.     The helper cell according to claim 13, wherein said two separate promoter sequences are TR339 26S promoter sequences.

15.     The helper cell according to claim 7, wherein said replicon RNA comprises a promoter sequence which directs the expression of a first heterologous RNA sequence and an IRES sequence upstream of a second heterologous RNA sequence.

16.     The helper cell according to claim 7, wherein said replicon RNA comprises two different heterologous RNA sequences.

17.     The helper cell according to claim 16, wherein said two different heterologous RNA sequences each encode an immunogenic protein or peptide which are different from each other.

18.     The helper cell according to claim 7, wherein said replicon RNA encodes a TR339 packaging segment.

UNITED STATES PATENT AND TRADEMARK OFFICE
CERTIFICATE OF CORRECTION

| | |
|---|---|
| PATENT NO. | : 6,008,035 |
| APPLICATION NO. | : 09/102248 |
| DATED | : December 28, 1999 |
| INVENTOR(S) | : Johnston et al. |

It is certified that error appears in the above-identified patent and that said Letters Patent is hereby corrected as shown below:

19. The helper cell according to claim 1, further containing a TR339 replicon RNA;
said replicon RNA encoding an alphavirus packaging segment and an inserted heterologous RNA;
wherein said replicon RNA and said first helper RNA are separate molecules;
and wherein the molecule containing said replicon RNA further contains RNA encoding said at least one TR339 structural protein not encoded by said first helper RNA.

20. The helper cell according to claim 19, wherein at least one of the helper RNAs or said replicon RNA comprises an attenuating mutation.

21. The helper cell according to claim 19, wherein the helper RNAs and said replicon RNA are expressed from cDNA introduced into said helper cell.

22. The helper cell according to claim 19, wherein said helper cell is transfected with RNAs comprises said replicon RNA and the helper RNAs.

23. The helper cell according to claim 19, wherein said replicon RNA encodes a TR339 packaging segment.

24. The helper cell according to claim 1, wherein said first helper RNA encodes both a TR339 E1 glycoprotein and a TR339 E2 glycoprotein, and wherein said second helper RNA encodes a TR339 capsid protein.

25. A method of making infectious, propagation defective, TR339 virus particles, comprising:
transfecting a TR339-permissive cell according to claim 1 with a propagation defective replicon RNA, said replicon RNA including an alphavirus packaging segment and an inserted heterologous RNA;
producing said TR339 virus particles in said transfected cell; and then
collecting said TR339 virus particles from said cell.

26. Infectious TR339 virus particles produced by the method of claim 25.

27. A pharmaceutical formulation comprising infectious TR339 virus particles according to claim 26 in a pharmaceutically acceptable carrier.

UNITED STATES PATENT AND TRADEMARK OFFICE
CERTIFICATE OF CORRECTION

| | |
|---|---|
| PATENT NO. | : 6,008,035 |
| APPLICATION NO. | : 09/102248 |
| DATED | : December 28, 1999 |
| INVENTOR(S) | : Johnston et al. |

It is certified that error appears in the above-identified patent and that said Letters Patent is hereby corrected as shown below:

28. The pharmaceutical formulation according to claim 27, wherein said heterologous RNA encodes an immunogenic peptide or protein, and further wherein said infectious TR339 virus particles are included in the pharmaceutical formulation in an immunogenic amount.

29. Infectious TR339 virus particles containing a TR339 replicon RNA encoding a promoter, an inserted heterologous RNA, and wherein RNA encoding at least one TR339 structural protein is deleted therefrom so that said virus particle is propagation defective.

30. A pharmaceutical formulation comprising infectious TR339 virus particles according to claim 29 in a pharmaceutically acceptable carrier.

31. A recombinant DNA comprising a cDNA coding for a Sindbis strain TR339 RNA transcript and a heterologous promoter positioned upstream from said cDNA and operatively associated therewith.

32. An infectious RNA transcript encoded by a cDNA according to claim 31.

33. An infectious RNA according to claim 32, said infectious TR339 RNA transcript containing a heterologous RNA operably associated with a promoter.

34. Infectious viral particles containing an RNA transcript according to claim 32.

35. The recombinant DNA of claim 31 further comprising a heterologous DNA sequence.

UNITED STATES PATENT AND TRADEMARK OFFICE
CERTIFICATE OF CORRECTION

| | |
|---|---|
| PATENT NO. | : 6,008,035 |
| APPLICATION NO. | : 09/102248 |
| DATED | : December 28, 1999 |
| INVENTOR(S) | : Johnston et al. |

It is certified that error appears in the above-identified patent and that said Letters Patent is hereby corrected as shown below:

36.    A helper cell for expressing an infectious, propagation defective, alphavirus particle, comprising, in an alphavirus-permissive cell:
    (a)    a first helper RNA encoding *(i)* at least one alphavirus structural protein, and *(ii)* not encoding at least one other alphavirus structural protein;
    (b)    a second helper RNA separate from said first helper RNA, said second helper RNA *(i)* not encoding said at least one alphavirus structural protein not encoded by said first helper RNA; and
    (c)    a TR339 replicon RNA, said TR339 replicon RNA encoding an alphavirus packaging segment and a heterologous RNA;
    wherein an alphavirus packaging segment is absent from at least said first helper RNA;
    and further wherein all of said alphavirus structural proteins encoded by the helper RNAs assemble together into alphavirus particles in said cell containing said TR339 replicon RNA.

37.    The helper cell according to claim 36, wherein said TR339 replicon RNA, said first helper RNA, and said second helper RNA are all separate molecules from one another.

38.    The helper cell according to claim 36, wherein said TR339 replicon RNA and said first helper RNA are separate molecules, and further wherein the molecule comprising said TR339 replicon RNA further comprises RNA encoding said at least one alphavirus structural protein not encoded by said first helper RNA.

39.    A helper cell for expressing an infectious, propagation defective, alphavirus particle, comprising, in an alphavirus-permissive cell:
    (a)    a first helper RNA encoding *(i)* at least one TR339 structural protein, and *(ii)* not encoding at least one other TR339 structural protein;
    (b)    a second helper RNA separate from said first helper RNA, said second helper RNA *(i)* not encoding said at least one TR339 structural protein encoded by said first helper RNA, and *(ii)* encoding said at least one other TR339 structural protein not encoded by said first helper RNA; and
    (c)    an alphavirus replicon RNA, said alphavirus replicon RNA encoding an alphavirus packaging segment and a heterologous RNA;
    wherein an alphavirus packaging segment is absent from at least said first helper RNA;
    and further wherein all of said TR339 structural proteins encoded by the helper RNAs assemble together into alphavirus particles in said cell containing said alphavirus replicon RNA.

UNITED STATES PATENT AND TRADEMARK OFFICE
CERTIFICATE OF CORRECTION

| | |
|---|---|
| PATENT NO. | : 6,008,035 |
| APPLICATION NO. | : 09/102248 |
| DATED | : December 28, 1999 |
| INVENTOR(S) | : Johnston et al. |

It is certified that error appears in the above-identified patent and that said Letters Patent is hereby corrected as shown below:

40. The helper cell according to claim 39, wherein said alphavirus replicon RNA, said first helper RNA, and said second helper RNA are all separate molecules from one another.

41. The helper cell according to claim 39, wherein said alphavirus replicon RNA and said first helper RNA are separate molecules, and further wherein the molecule comprising said alphavirus replicon RNA further comprises RNA encoding said at least one TR339 structural protein not encoded by said first helper RNA.

42. A composition comprising infectious, propagation defective, virus particles, wherein each particle comprises a TR339 nucleocapsid and an alphavirus replicon RNA, wherein the replicon RNA comprises an alphavirus packaging signal, one or more heterologous RNA sequences, and a sequence encoding at least one TR339 structural protein, and further wherein the replicon RNA lacks a sequence encoding at least one TR339 structural protein.

43. A pharmaceutical formulation comprising the composition according to claim 42 in a pharmaceutically-acceptable carrier.

44. The pharmaceutical formulation according to claim 43, wherein said one or more heterologous RNA sequences encode an immunogenic protein or peptide, and further wherein said composition is included in the pharmaceutical formulation in an immunogenic amount.

45. A composition comprising infectious, propagation defective, virus particles, wherein each particle comprises a TR339 nucleocapsid and an alphavirus replicon RNA, wherein the replicon RNA comprises an alphavirus packaging signal, one or more heterologous RNA sequences, and further wherein the replicon RNA lacks sequences encoding TR339 structural proteins.

46. The composition according to claim 45, wherein said alphavirus replicon RNA is from TR339.

47. A pharmaceutical formulation comprising the composition according to claim 45 in a pharmaceutically-acceptable carrier.

48. The pharmaceutical formulation according to claim 47, wherein said one or more heterologous RNA sequences encode an immunogenic protein or peptide, and further wherein said composition is included in the pharmaceutical formulation in an immunogenic amount.

UNITED STATES PATENT AND TRADEMARK OFFICE
CERTIFICATE OF CORRECTION

| | | |
|---|---|---|
| PATENT NO. | : 6,008,035 | |
| APPLICATION NO. | : 09/102248 | |
| DATED | : December 28, 1999 | |
| INVENTOR(S) | : Johnston et al. | |

It is certified that error appears in the above-identified patent and that said Letters Patent is hereby corrected as shown below:

49.  A composition comprising infectious, propagation defective, virus particles, wherein each particle comprises an alphavirus nucleocapsid and a TR339 replicon RNA, wherein the TR339 replicon RNA comprises an alphavirus packaging signal, one or more heterologous RNA sequences, and further wherein the TR339 replicon RNA lacks sequences encoding alphavirus structural proteins.

50.  A pharmaceutical formulation comprising the composition according to claim 49 in a pharmaceutically-acceptable carrier.

51.  The pharmaceutical formulation according to claim 50, wherein said one or more heterologous RNA sequences encode an immunogenic protein or peptide, and further wherein said composition is included in the pharmaceutical formulation in an immunogenic amount.

52.  A cDNA encoding a TR339 virus genome.

53.  The cDNA of claim 52, wherein said cDNA has the sequence given as SEQ ID NO:8.

54.  An RNA comprising a TR339 virus genome.

55.  The RNA of claim 54, wherein said RNA has a sequence encoded by the cDNA of SEQ ID NO:8.

56.  Infectious TR339 virus particles containing a TR339 replicon RNA encoding a promoter, an inserted heterologous RNA, and wherein said replicon RNA lacks sequences encoding TR339 structural proteins so that said virus particle is propagation defective.

57.  A pharmaceutical formulation comprising infectious TR339 virus particles according to claim 56 in a pharmaceutically acceptable carrier.

58.  A composition comprising infectious, propagation defective, virus particles, wherein each particle comprises an alphavirus nucleocapsid and a TR339 replicon RNA, wherein the replicon RNA comprises an alphavirus packaging signal, one or more heterologous RNA sequences, and a sequence encoding at least one alphavirus structural protein, and further wherein the replicon RNA lacks a sequence encoding at least one alphavirus structural protein.

UNITED STATES PATENT AND TRADEMARK OFFICE
CERTIFICATE OF CORRECTION

| | |
|---|---|
| PATENT NO. | : 6,008,035 |
| APPLICATION NO. | : 09/102248 |
| DATED | : December 28, 1999 |
| INVENTOR(S) | : Johnston et al. |

It is certified that error appears in the above-identified patent and that said Letters Patent is hereby corrected as shown below:

59.   A pharmaceutical formulation comprising the composition according to claim 58 in a pharmaceutically-acceptable carrier.

60.   The pharmaceutical formulation according to claim 59, wherein said one or more heterologous RNA sequences encode an immunogenic peptide or protein, and further wherein said composition is included in the pharmaceutical formulation in an immunogenic amount. --

Signed and Sealed this

Fourteenth Day of November, 2006

JON W. DUDAS
*Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 11663 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 60..7559

(ix) FEATURE:
      (A) NAME/KEY: CDS
      (B) LOCATION: 7608..11342

(xi) SEQUENCE DESCRIPTION: SEQ ID NO:1:

```
ATTGGCGGCG TAGTACACAC TATTGAATCA AACAGCCGAC CAATTGCACT ACCATCACA        59

ATG GAG AAG CCA GTA GTT AAC GTA GAC GTA GAC CCT CAG AGT CCG TTT       107
Met Glu Lys Pro Val Val Asn Val Asp Val Asp Pro Gln Ser Pro Phe
  1               5                  10                  15

GTC GTG CAA CTG CAA AAG AGC TTC CCG CAA TTT GAG GTA GTA GCA CAG       155
Val Val Gln Leu Gln Lys Ser Phe Pro Gln Phe Glu Val Val Ala Gln
             20                  25                  30

CAG GTC ACT CCA AAT GAC CAT GCT AAT GCC AGA GCA TTT TCG CAT CTG       203
Gln Val Thr Pro Asn Asp His Ala Asn Ala Arg Ala Phe Ser His Leu
         35                  40                  45

GCC AGT AAA CTA ATC GAG CTG GAG GTT CCT ACC ACA GCG ACG ATT TTG       251
Ala Ser Lys Leu Ile Glu Leu Glu Val Pro Thr Thr Ala Thr Ile Leu
     50                  55                  60

GAC ATA GGC AGC GCA CCG GCT CGT AGA ATG TTT TCC GAG CAC CAG TAC       299
Asp Ile Gly Ser Ala Pro Ala Arg Arg Met Phe Ser Glu His Gln Tyr
 65                  70                  75                  80

CAT TGC GTT TGC CCC ATG CGT AGT CCA GAA GAC CCG GAC CGC ATG ATG       347
His Cys Val Cys Pro Met Arg Ser Pro Glu Asp Pro Asp Arg Met Met
                     85                  90                  95
```

-continued

```
AAA TAT GCC AGC AAA CTG GCG GAA AAA GCA TGT AAG ATT ACA AAC AAG         395
Lys Tyr Ala Ser Lys Leu Ala Glu Lys Ala Cys Lys Ile Thr Asn Lys
            100                 105                 110

AAC TTG CAT GAG AAG ATC AAG GAC CTC CGG ACC GTA CTT GAT ACA CCG         443
Asn Leu His Glu Lys Ile Lys Asp Leu Arg Thr Val Leu Asp Thr Pro
            115                 120                 125

GAT GCT GAA ACG CCA TCA CTC TGC TTC CAC AAC GAT GTT ACC TGC AAC         491
Asp Ala Glu Thr Pro Ser Leu Cys Phe His Asn Asp Val Thr Cys Asn
130                 135                 140

ACG CGT GCC GAG TAC TCC GTC ATG CAG GAC GTG TAC ATC AAC GCT CCC         539
Thr Arg Ala Glu Tyr Ser Val Met Gln Asp Val Tyr Ile Asn Ala Pro
145                 150                 155                 160

GGA ACT ATT TAC CAC CAG GCT ATG AAA GGC GTG CGG ACC CTG TAC TGG         587
Gly Thr Ile Tyr His Gln Ala Met Lys Gly Val Arg Thr Leu Tyr Trp
                165                 170                 175

ATT GGC TTC GAC ACC ACC CAG TTC ATG TTC TCG GCT ATG GCA GGT TCG         635
Ile Gly Phe Asp Thr Thr Gln Phe Met Phe Ser Ala Met Ala Gly Ser
                180                 185                 190

TAC CCT GCA TAC AAC ACC AAC TGG GCC GAC GAA AAA GTC CTT GAA GCG         683
Tyr Pro Ala Tyr Asn Thr Asn Trp Ala Asp Glu Lys Val Leu Glu Ala
                195                 200                 205

CGT AAC ATC GGA CTC TGC AGC ACA AAG CTG AGT GAA GGC AGG ACA GGA         731
Arg Asn Ile Gly Leu Cys Ser Thr Lys Leu Ser Glu Gly Arg Thr Gly
210                 215                 220

AAG TTG TCG ATA ATG AGG AAG AAG GAG TTG AAG CCC GGG TCA CGG GTT         779
Lys Leu Ser Ile Met Arg Lys Lys Glu Leu Lys Pro Gly Ser Arg Val
225                 230                 235                 240

TAT TTC TCC GTT GGA TCG ACA CTT TAC CCA GAA CAC AGA GCC AGC TTG         827
Tyr Phe Ser Val Gly Ser Thr Leu Tyr Pro Glu His Arg Ala Ser Leu
                245                 250                 255

CAG AGC TGG CAT CTT CCA TCG GTG TTC CAC TTG AAA GGA AAG CAG TCG         875
Gln Ser Trp His Leu Pro Ser Val Phe His Leu Lys Gly Lys Gln Ser
                260                 265                 270

TAC ACT TGC CGC TGT GAT ACA GTG GTG AGC TGC GAA GGC TAC GTA GTG         923
Tyr Thr Cys Arg Cys Asp Thr Val Val Ser Cys Glu Gly Tyr Val Val
                275                 280                 285

AAG AAA ATC ACC ATC AGT CCC GGG ATC ACG GGA GAA ACC GTG GGA TAC         971
Lys Lys Ile Thr Ile Ser Pro Gly Ile Thr Gly Glu Thr Val Gly Tyr
290                 295                 300

GCG GTT ACA AAC AAT AGC GAG GGC TTC TTG CTA TGC AAA GTT ACC GAT        1019
Ala Val Thr Asn Asn Ser Glu Gly Phe Leu Leu Cys Lys Val Thr Asp
305                 310                 315                 320

ACA GTA AAA GGA GAA CGG GTA TCG TTC CCC GTG TGC ACG TAT ATC CCG        1067
Thr Val Lys Gly Glu Arg Val Ser Phe Pro Val Cys Thr Tyr Ile Pro
                325                 330                 335

GCC ACC ATA TGC GAT CAG ATG ACC GGC ATA ATG GCC ACG GAT ATC TCA        1115
Ala Thr Ile Cys Asp Gln Met Thr Gly Ile Met Ala Thr Asp Ile Ser
                340                 345                 350

CCT GAC GAT GCA CAA AAA CTT CTG GTT GGG CTC AAC CAG CGA ATC GTC        1163
Pro Asp Asp Ala Gln Lys Leu Leu Val Gly Leu Asn Gln Arg Ile Val
                355                 360                 365

ATT AAC GGT AAG ACT AAC AGG AAC ACC AAT ACC ATG CAA AAT TAC CTT        1211
Ile Asn Gly Lys Thr Asn Arg Asn Thr Asn Thr Met Gln Asn Tyr Leu
370                 375                 380

CTG CCA ATC ATT GCA CAA GGG TTC AGC AAA TGG GCC AAG GAG CGC AAA        1259
Leu Pro Ile Ile Ala Gln Gly Phe Ser Lys Trp Ala Lys Glu Arg Lys
385                 390                 395                 400

GAA GAT CTT GAC AAT GAA AAA ATG CTG GGC ACC AGA GAG CGC AAG CTT        1307
Glu Asp Leu Asp Asn Glu Lys Met Leu Gly Thr Arg Glu Arg Lys Leu
                405                 410                 415
```

```
ACA TAT GGC TGC TTG TGG GCG TTT CGC ACT AAG AAA GTG CAC TCG TTC    1355
Thr Tyr Gly Cys Leu Trp Ala Phe Arg Thr Lys Lys Val His Ser Phe
            420                 425                 430

TAT CGC CCA CCT GGA ACG CAG ACC ATC GTA AAA GTC CCA GCC TCT TTT    1403
Tyr Arg Pro Pro Gly Thr Gln Thr Ile Val Lys Val Pro Ala Ser Phe
            435                 440                 445

AGC GCT TTC CCC ATG TCA TCC GTA TGG ACT ACC TCT TTG CCC ATG TCG    1451
Ser Ala Phe Pro Met Ser Ser Val Trp Thr Thr Ser Leu Pro Met Ser
        450                 455                 460

CTG AGG CAG AAG ATG AAA TTG GCA TTA CAA CCA AAG AAG GAG GAA AAA    1499
Leu Arg Gln Lys Met Lys Leu Ala Leu Gln Pro Lys Lys Glu Glu Lys
465                 470                 475                 480

CTG CTG CAA GTC CCG GAG GAA TTA GTT ATG GAG GCC AAG GCT GCT TTC    1547
Leu Leu Gln Val Pro Glu Glu Leu Val Met Glu Ala Lys Ala Ala Phe
                485                 490                 495

GAG GAT GCT CAG GAG GAA TCC AGA GCG GAG AAG CTC CGA GAA GCA CTC    1595
Glu Asp Ala Gln Glu Glu Ser Arg Ala Glu Lys Leu Arg Glu Ala Leu
                500                 505                 510

CCA CCA TTA GTG GCA GAC AAA GGT ATC GAG GCA GCT GCG GAA GTT GTC    1643
Pro Pro Leu Val Ala Asp Lys Gly Ile Glu Ala Ala Ala Glu Val Val
            515                 520                 525

TGC GAA GTG GAG GGG CTC CAG GCG GAC ACC GGA GCA GCA CTC GTC GAA    1691
Cys Glu Val Glu Gly Leu Gln Ala Asp Thr Gly Ala Ala Leu Val Glu
        530                 535                 540

ACC CCG CGC GGT CAT GTA AGG ATA ATA CCT CAA GCA AAT GAC CGT ATG    1739
Thr Pro Arg Gly His Val Arg Ile Ile Pro Gln Ala Asn Asp Arg Met
545                 550                 555                 560

ATC GGA CAG TAT ATC GTT GTC TCG CCG ATC TCT GTG CTG AAG AAC GCT    1787
Ile Gly Gln Tyr Ile Val Val Ser Pro Ile Ser Val Leu Lys Asn Ala
                565                 570                 575

AAA CTC GCA CCA GCA CAC CCG CTA GCA GAC CAG GTT AAG ATC ATA ACG    1835
Lys Leu Ala Pro Ala His Pro Leu Ala Asp Gln Val Lys Ile Ile Thr
                580                 585                 590

CAC TCC GGA AGA TCA GGA AGG TAT GCA GTC GAA CCA TAC GAC GCT AAA    1883
His Ser Gly Arg Ser Gly Arg Tyr Ala Val Glu Pro Tyr Asp Ala Lys
            595                 600                 605

GTA CTG ATG CCA GCA GGA AGT GCC GTA CCA TGG CCA GAA TTC TTA GCA    1931
Val Leu Met Pro Ala Gly Ser Ala Val Pro Trp Pro Glu Phe Leu Ala
610                 615                 620

CTG AGT GAG AGC GCC ACG CTT GTG TAC AAC GAA AGA GAG TTT GTG AAC    1979
Leu Ser Glu Ser Ala Thr Leu Val Tyr Asn Glu Arg Glu Phe Val Asn
625                 630                 635                 640

CGC AAG CTG TAC CAT ATT GCC ATG CAC GGT CCC GCT AAG AAT ACA GAA    2027
Arg Lys Leu Tyr His Ile Ala Met His Gly Pro Ala Lys Asn Thr Glu
                645                 650                 655

GAG GAG CAG TAC AAG GTT ACA AAG GCA GAG CTC GCA GAA ACA GAG TAC    2075
Glu Glu Gln Tyr Lys Val Thr Lys Ala Glu Leu Ala Glu Thr Glu Tyr
                660                 665                 670

GTG TTT GAC GTG GAC AAG AAG CGA TGC GTT AAG AAG GAA GAA GCC TCA    2123
Val Phe Asp Val Asp Lys Lys Arg Cys Val Lys Lys Glu Glu Ala Ser
            675                 680                 685

GGA CTT GTC CTT TCG GGA GAA CTG ACC AAC CCG CCC TAT CAC GAA CTA    2171
Gly Leu Val Leu Ser Gly Glu Leu Thr Asn Pro Pro Tyr His Glu Leu
        690                 695                 700

GCT CTT GAG GGA CTG AAG ACT CGA CCC GCG GTC CCG TAC AAG GTT GAA    2219
Ala Leu Glu Gly Leu Lys Thr Arg Pro Ala Val Pro Tyr Lys Val Glu
705                 710                 715                 720

ACA ATA GGA GTG ATA GGC ACA CCA GGA TCG GGC AAG TCA GCT ATC ATC    2267
Thr Ile Gly Val Ile Gly Thr Pro Gly Ser Gly Lys Ser Ala Ile Ile
                725                 730                 735
```

-continued

```
AAG TCA ACT GTC ACG GCA CGT GAT CTT GTT ACC AGC GGA AAG AAA GAA      2315
Lys Ser Thr Val Thr Ala Arg Asp Leu Val Thr Ser Gly Lys Lys Glu
            740                 745                 750

AAC TGC CGC GAA ATT GAG GCC GAC GTG CTA CGG CTG AGG GGC ATG CAG      2363
Asn Cys Arg Glu Ile Glu Ala Asp Val Leu Arg Leu Arg Gly Met Gln
            755                 760                 765

ATC ACG TCG AAG ACA GTG GAT TCG GTT ATG CTC AAC GGA TGC CAC AAA      2411
Ile Thr Ser Lys Thr Val Asp Ser Val Met Leu Asn Gly Cys His Lys
770                 775                 780

GCC GTA GAA GTG CTG TAT GTT GAC GAA GCG TTC CGG TGC CAC GCA GGA      2459
Ala Val Glu Val Leu Tyr Val Asp Glu Ala Phe Arg Cys His Ala Gly
785                 790                 795                 800

GCA CTA CTT GCC TTG ATT GCA ATC GTC AGA CCC CGT AAG AAG GTA GTA      2507
Ala Leu Leu Ala Leu Ile Ala Ile Val Arg Pro Arg Lys Lys Val Val
                    805                 810                 815

CTA TGC GGA GAC CCT AAG CAA TGC GGA TTC TTC AAC ATG ATG CAA CTA      2555
Leu Cys Gly Asp Pro Lys Gln Cys Gly Phe Phe Asn Met Met Gln Leu
                820                 825                 830

AAG GTA CAT TTC AAC CAC CCT GAA AAA GAC ATA TGT ACC AAG ACA TTC      2603
Lys Val His Phe Asn His Pro Glu Lys Asp Ile Cys Thr Lys Thr Phe
            835                 840                 845

TAC AAG TTT ATC TCC CGA CGT TGC ACA CAG CCA GTC ACG GCT ATT GTA      2651
Tyr Lys Phe Ile Ser Arg Arg Cys Thr Gln Pro Val Thr Ala Ile Val
            850                 855                 860

TCG ACA CTG CAT TAC GAT GGA AAA ATG AAA ACC ACA AAC CCG TGC AAG      2699
Ser Thr Leu His Tyr Asp Gly Lys Met Lys Thr Thr Asn Pro Cys Lys
865                 870                 875                 880

AAG AAC ATC GAA ATC GAC ATT ACA GGG GCC ACG AAG CCG AAG CCA GGG      2747
Lys Asn Ile Glu Ile Asp Ile Thr Gly Ala Thr Lys Pro Lys Pro Gly
                    885                 890                 895

GAC ATC ATC CTG ACA TGT TTC CGC GGG TGG GTT AAG CAA CTG CAA ATC      2795
Asp Ile Ile Leu Thr Cys Phe Arg Gly Trp Val Lys Gln Leu Gln Ile
                900                 905                 910

GAC TAT CCC GGA CAT GAG GTA ATG ACA GCC GCG GCC TCA CAA GGG CTA      2843
Asp Tyr Pro Gly His Glu Val Met Thr Ala Ala Ala Ser Gln Gly Leu
            915                 920                 925

ACC AGA AAA GGA GTA TAT GCC GTC CGG CAA AAA GTC AAT GAA AAC CCG      2891
Thr Arg Lys Gly Val Tyr Ala Val Arg Gln Lys Val Asn Glu Asn Pro
            930                 935                 940

CTG TAC GCG ATC ACA TCA GAG CAT GTG AAC GTG TTG CTC ACC CGC ACT      2939
Leu Tyr Ala Ile Thr Ser Glu His Val Asn Val Leu Leu Thr Arg Thr
945                 950                 955                 960

GAG GAC AGG CTA GTA TGG AAA ACT TTA CAG GGC GAC CCA TGG ATT AAG      2987
Glu Asp Arg Leu Val Trp Lys Thr Leu Gln Gly Asp Pro Trp Ile Lys
                    965                 970                 975

CAG CTC ACT AAC GTA CCT AAA GGA AAT TTT CAG GCC ACC ATC GAG GAC      3035
Gln Leu Thr Asn Val Pro Lys Gly Asn Phe Gln Ala Thr Ile Glu Asp
                980                 985                 990

TGG GAA GCT GAA CAC AAG GGA ATA ATT GCT GCG ATA AAC AGT CCC GCT      3083
Trp Glu Ala Glu His Lys Gly Ile Ile Ala Ala Ile Asn Ser Pro Ala
            995                 1000                1005

CCC CGT ACC AAT CCG TTC AGC TGC AAG ACT AAC GTT TGC TGG GCG AAA      3131
Pro Arg Thr Asn Pro Phe Ser Cys Lys Thr Asn Val Cys Trp Ala Lys
            1010                1015                1020

GCA CTG GAA CCG ATA CTG GCC ACG GCC GGT ATC GTA CTT ACC GGT TGC      3179
Ala Leu Glu Pro Ile Leu Ala Thr Ala Gly Ile Val Leu Thr Gly Cys
1025                1030                1035                1040

CAG TGG AGC GAG CTG TTC CCA CAG TTT GCG GAT GAC AAA CCA CAC TCG      3227
Gln Trp Ser Glu Leu Phe Pro Gln Phe Ala Asp Asp Lys Pro His Ser
                    1045                1050                1055
```

```
GCC ATC TAC GCC TTA GAC GTA ATT TGC ATT AAG TTT TTC GGC ATG GAC      3275
Ala Ile Tyr Ala Leu Asp Val Ile Cys Ile Lys Phe Phe Gly Met Asp
             1060                1065                1070

TTG ACA AGC GGG CTG TTT TCC AAA CAG AGC ATC CCG TTA ACG TAC CAT      3323
Leu Thr Ser Gly Leu Phe Ser Lys Gln Ser Ile Pro Leu Thr Tyr His
             1075                1080                1085

CCT GCC GAC TCA GCG AGG CCA GTA GCT CAT TGG GAC AAC AGC CCA GGA      3371
Pro Ala Asp Ser Ala Arg Pro Val Ala His Trp Asp Asn Ser Pro Gly
             1090                1095                1100

ACA CGC AAG TAT GGG TAC GAT CAC GCC GTT GCC GCC GAA CTC TCC CGT      3419
Thr Arg Lys Tyr Gly Tyr Asp His Ala Val Ala Ala Glu Leu Ser Arg
1105                1110                1115                1120

AGA TTT CCG GTG TTC CAG CTA GCT GGG AAA GGC ACA CAG CTT GAT TTG      3467
Arg Phe Pro Val Phe Gln Leu Ala Gly Lys Gly Thr Gln Leu Asp Leu
             1125                1130                1135

CAG ACG GGC AGA ACT AGA GTT ATC TCT GCA CAG CAT AAC TTG GTC CCA      3515
Gln Thr Gly Arg Thr Arg Val Ile Ser Ala Gln His Asn Leu Val Pro
             1140                1145                1150

GTG AAC CGC AAT CTC CCT CAC GCC TTA GTC CCC GAG CAC AAG GAG AAA      3563
Val Asn Arg Asn Leu Pro His Ala Leu Val Pro Glu His Lys Glu Lys
             1155                1160                1165

CAA CCC GGC CCG GTC GAA AAA TTC TTG AGC CAG TTC AAA CAC CAC TCC      3611
Gln Pro Gly Pro Val Glu Lys Phe Leu Ser Gln Phe Lys His His Ser
    1170                1175                1180

GTA CTT GTG ATC TCA GAG AAA AAA ATT GAA GCT CCC CAC AAG AGA ATC      3659
Val Leu Val Ile Ser Glu Lys Lys Ile Glu Ala Pro His Lys Arg Ile
1185                1190                1195                1200

GAA TGG ATC GCC CCG ATT GGC ATA GCC GGC GCA GAT AAG AAC TAC AAC      3707
Glu Trp Ile Ala Pro Ile Gly Ile Ala Gly Ala Asp Lys Asn Tyr Asn
             1205                1210                1215

CTG GCT TTC GGG TTT CCG CCG CAG GCA CGG TAC GAC CTG GTG TTC ATC      3755
Leu Ala Phe Gly Phe Pro Pro Gln Ala Arg Tyr Asp Leu Val Phe Ile
             1220                1225                1230

AAT ATT GGA ACT AAA TAC AGA AAC CAT CAC TTT CAA CAG TGC GAA GAC      3803
Asn Ile Gly Thr Lys Tyr Arg Asn His His Phe Gln Gln Cys Glu Asp
             1235                1240                1245

CAC GCG GCG ACC TTG AAA ACC CTT TCG CGT TCG GCC CTG AAC TGC CTT      3851
His Ala Ala Thr Leu Lys Thr Leu Ser Arg Ser Ala Leu Asn Cys Leu
             1250                1255                1260

AAC CCC GGA GGC ACC CTC GTG GTG AAG TCC TAC GGT TAC GCC GAC CGC      3899
Asn Pro Gly Gly Thr Leu Val Val Lys Ser Tyr Gly Tyr Ala Asp Arg
1265                1270                1275                1280

AAT AGT GAG GAC GTA GTC ACC GCT CTT GCC AGA AAA TTT GTC AGA GTG      3947
Asn Ser Glu Asp Val Val Thr Ala Leu Ala Arg Lys Phe Val Arg Val
             1285                1290                1295

TCT GCA GCG AGG CCA GAG TGC GTC TCA AGC AAT ACA GAA ATG TAC CTG      3995
Ser Ala Ala Arg Pro Glu Cys Val Ser Ser Asn Thr Glu Met Tyr Leu
             1300                1305                1310

ATT TTC CGA CAA CTA GAC AAC AGC CGC ACA CGA CAA TTC ACC CCG CAT      4043
Ile Phe Arg Gln Leu Asp Asn Ser Arg Thr Arg Gln Phe Thr Pro His
             1315                1320                1325

CAT TTG AAT TGT GTG ATT TCG TCC GTG TAC GAG GGT ACA AGA GAC GGA      4091
His Leu Asn Cys Val Ile Ser Ser Val Tyr Glu Gly Thr Arg Asp Gly
             1330                1335                1340

GTT GGA GCC GCA CCG TCG TAC CGT ACT AAA AGG GAG AAC ATT GCT GAT      4139
Val Gly Ala Ala Pro Ser Tyr Arg Thr Lys Arg Glu Asn Ile Ala Asp
1345                1350                1355                1360

TGT CAA GAG GAA GCA GTT GTC AAT GCA GCC AAT CCA CTG GGC AGA CCA      4187
Cys Gln Glu Glu Ala Val Val Asn Ala Ala Asn Pro Leu Gly Arg Pro
             1365                1370                1375
```

```
GGA GAA GGA GTC TGC CGT GCC ATC TAT AAA CGT TGG CCG AAC AGT TTC      4235
Gly Glu Gly Val Cys Arg Ala Ile Tyr Lys Arg Trp Pro Asn Ser Phe
            1380                1385                1390

ACC GAT TCA GCC ACA GAG ACA GGT ACC GCA AAA CTG ACT GTG TGC CAA      4283
Thr Asp Ser Ala Thr Glu Thr Gly Thr Ala Lys Leu Thr Val Cys Gln
            1395                1400                1405

GGA AAG AAA GTG ATC CAC GCG GTT GGC CCT GAT TTC CGG AAA CAC CCA      4331
Gly Lys Lys Val Ile His Ala Val Gly Pro Asp Phe Arg Lys His Pro
    1410                1415                1420

GAG GCA GAA GCC CTG AAA TTG CTG CAA AAC GCC TAC CAT GCA GTG GCA      4379
Glu Ala Glu Ala Leu Lys Leu Leu Gln Asn Ala Tyr His Ala Val Ala
1425                1430                1435                1440

GAC TTA GTA AAT GAA CAT AAT ATC AAG TCT GTC GCC ATC CCA CTG CTA      4427
Asp Leu Val Asn Glu His Asn Ile Lys Ser Val Ala Ile Pro Leu Leu
                1445                1450                1455

TCT ACA GGC ATT TAC GCA GCC GGA AAA GAC CGC CTT GAG GTA TCA CTT      4475
Ser Thr Gly Ile Tyr Ala Ala Gly Lys Asp Arg Leu Glu Val Ser Leu
            1460                1465                1470

AAC TGC TTG ACA ACC GCG CTA GAC AGA ACT GAT GCG GAC GTA ACC ATC      4523
Asn Cys Leu Thr Thr Ala Leu Asp Arg Thr Asp Ala Asp Val Thr Ile
        1475                1480                1485

TAC TGC CTG GAT AAG AAG TGG AAG GAA AGA ATC GAC GCG GTG CTC CAA      4571
Tyr Cys Leu Asp Lys Lys Trp Lys Glu Arg Ile Asp Ala Val Leu Gln
    1490                1495                1500

CTT AAG GAG TCT GTA ACT GAG CTG AAG GAT GAG GAT ATG GAG ATC GAC      4619
Leu Lys Glu Ser Val Thr Glu Leu Lys Asp Glu Asp Met Glu Ile Asp
1505                1510                1515                1520

GAC GAG TTA GTA TGG ATC CAT CCG GAC AGT TGC CTG AAG GGA AGA AAG      4667
Asp Glu Leu Val Trp Ile His Pro Asp Ser Cys Leu Lys Gly Arg Lys
                1525                1530                1535

GGA TTC AGT ACT ACA AAA GGA AAG TTG TAT TCG TAC TTT GAA GGC ACC      4715
Gly Phe Ser Thr Thr Lys Gly Lys Leu Tyr Ser Tyr Phe Glu Gly Thr
            1540                1545                1550

AAA TTC CAT CAA GCA GCA AAA GAT ATG GCG GAG ATA AAG GTC CTG TTC      4763
Lys Phe His Gln Ala Ala Lys Asp Met Ala Glu Ile Lys Val Leu Phe
        1555                1560                1565

CCA AAT GAC CAG GAA AGC AAC GAA CAA CTG TGT GCC TAC ATA TTG GGG      4811
Pro Asn Asp Gln Glu Ser Asn Glu Gln Leu Cys Ala Tyr Ile Leu Gly
    1570                1575                1580

GAG ACC ATG GAA GCA ATC CGC GAA AAA TGC CCG GTC GAC CAC AAC CCG      4859
Glu Thr Met Glu Ala Ile Arg Glu Lys Cys Pro Val Asp His Asn Pro
1585                1590                1595                1600

TCG TCT AGC CCG CCA AAA ACG CTG CCG TGC CTC TGT ATG TAT GCC ATG      4907
Ser Ser Ser Pro Pro Lys Thr Leu Pro Cys Leu Cys Met Tyr Ala Met
                1605                1610                1615

ACG CCA GAA AGG GTC CAC AGA CTC AGA AGC AAT AAC GTC AAA GAA GTT      4955
Thr Pro Glu Arg Val His Arg Leu Arg Ser Asn Asn Val Lys Glu Val
            1620                1625                1630

ACA GTA TGC TCC TCC ACC CCC CTT CCA AAG TAC AAA ATC AAG AAT GTT      5003
Thr Val Cys Ser Ser Thr Pro Leu Pro Lys Tyr Lys Ile Lys Asn Val
        1635                1640                1645

CAG AAG GTT CAG TGC ACA AAA GTA GTC CTG TTT AAC CCG CAT ACC CCC      5051
Gln Lys Val Gln Cys Thr Lys Val Val Leu Phe Asn Pro His Thr Pro
    1650                1655                1660

GCA TTC GTT CCC GCC CGT AAG TAC ATA GAA GCA CCA GAA CAG CCT GCA      5099
Ala Phe Val Pro Ala Arg Lys Tyr Ile Glu Ala Pro Glu Gln Pro Ala
1665                1670                1675                1680

GCT CCG CCT GCA CAG GCC GAG GAG GCC CCC GGA GTT GTA GCG ACA CCA      5147
Ala Pro Pro Ala Gln Ala Glu Glu Ala Pro Gly Val Val Ala Thr Pro
                1685                1690                1695
```

```
ACA CCA CCT GCA GCT GAT AAC ACC TCG CTT GAT GTC ACG GAC ATC TCA    5195
Thr Pro Pro Ala Ala Asp Asn Thr Ser Leu Asp Val Thr Asp Ile Ser
            1700                1705                1710

CTG GAC ATG GAA GAC AGT AGC GAA GGC TCA CTC TTT TCG AGC TTT AGC    5243
Leu Asp Met Glu Asp Ser Ser Glu Gly Ser Leu Phe Ser Ser Phe Ser
        1715                1720                1725

GGA TCG GAC AAC TAC CGA AGG CAG GTG GTG GTG GCT GAC GTC CAT GCC    5291
Gly Ser Asp Asn Tyr Arg Arg Gln Val Val Val Ala Asp Val His Ala
        1730                1735                1740

GTC CAA GAG CCT GCC CCT GTT CCA CCG CCA AGG CTA AAG AAG ATG GCC    5339
Val Gln Glu Pro Ala Pro Val Pro Pro Pro Arg Leu Lys Lys Met Ala
1745                1750                1755                1760

CGC CTG GCA GCG GCA AGA ATG CAG GAA GAG CCA ACT CCA CCG GCA AGC    5387
Arg Leu Ala Ala Ala Arg Met Gln Glu Glu Pro Thr Pro Pro Ala Ser
            1765                1770                1775

ACC AGC TCT GCG GAC GAG TCC CTT CAC CTT TCT TTT GAT GGG GTA TCT    5435
Thr Ser Ser Ala Asp Glu Ser Leu His Leu Ser Phe Asp Gly Val Ser
        1780                1785                1790

ATA TCC TTC GGA TCC CTT TTC GAC GGA GAG ATG GCC CGC TTG GCA GCG    5483
Ile Ser Phe Gly Ser Leu Phe Asp Gly Glu Met Ala Arg Leu Ala Ala
        1795                1800                1805

GCA CAA CCC CCG GCA AGT ACA TGC CCT ACG GAT GTG CCT ATG TCT TTC    5531
Ala Gln Pro Pro Ala Ser Thr Cys Pro Thr Asp Val Pro Met Ser Phe
        1810                1815                1820

GGA TCG TTT TCC GAC GGA GAG ATT GAG GAG TTG AGC CGC AGA GTA ACC    5579
Gly Ser Phe Ser Asp Gly Glu Ile Glu Glu Leu Ser Arg Arg Val Thr
1825                1830                1835                1840

GAG TCG GAG CCC GTC CTG TTT GGG TCA TTT GAA CCG GGC GAA GTG AAC    5627
Glu Ser Glu Pro Val Leu Phe Gly Ser Phe Glu Pro Gly Glu Val Asn
            1845                1850                1855

TCA ATT ATA TCG TCC CGA TCA GCC GTA TCT TTT CCA CCA CGC AAG CAG    5675
Ser Ile Ile Ser Ser Arg Ser Ala Val Ser Phe Pro Pro Arg Lys Gln
        1860                1865                1870

AGA CGT AGA CGC AGG AGC AGG AGG ACC GAA TAC TGT CTA ACC GGG GTA    5723
Arg Arg Arg Arg Arg Ser Arg Arg Thr Glu Tyr Cys Leu Thr Gly Val
        1875                1880                1885

GGT GGG TAC ATA TTT TCG ACG GAC ACA GGC CCT GGG CAC TTG CAA AAG    5771
Gly Gly Tyr Ile Phe Ser Thr Asp Thr Gly Pro Gly His Leu Gln Lys
        1890                1895                1900

AAG TCC GTT CTG CAG AAC CAG CTT ACA GAA CCG ACC TTG GAG CGC AAT    5819
Lys Ser Val Leu Gln Asn Gln Leu Thr Glu Pro Thr Leu Glu Arg Asn
1905                1910                1915                1920

GTT CTG GAA AGA ATC TAC GCC CCG GTG CTC GAC ACG TCG AAA GAG GAA    5867
Val Leu Glu Arg Ile Tyr Ala Pro Val Leu Asp Thr Ser Lys Glu Glu
            1925                1930                1935

CAG CTC AAA CTC AGG TAC CAG ATG ATG CCC ACC GAA GCC AAC AAA AGC    5915
Gln Leu Lys Leu Arg Tyr Gln Met Met Pro Thr Glu Ala Asn Lys Ser
        1940                1945                1950

AGG TAC CAG TCT CGA AAA GTA GAA AAC CAG AAA GCC ATA ACC ACT GAG    5963
Arg Tyr Gln Ser Arg Lys Val Glu Asn Gln Lys Ala Ile Thr Thr Glu
        1955                1960                1965

CGA CTG CTT TCA GGG CTA CGA CTG TAT AAC TCT GCC ACA GAT CAG CCA    6011
Arg Leu Leu Ser Gly Leu Arg Leu Tyr Asn Ser Ala Thr Asp Gln Pro
        1970                1975                1980

GAA TGC TAT AAG ATC ACC TAC CCG AAA CCA TCG TAT TCC AGC AGT GTA    6059
Glu Cys Tyr Lys Ile Thr Tyr Pro Lys Pro Ser Tyr Ser Ser Ser Val
1985                1990                1995                2000

CCA GCG AAC TAC TCT GAC CCA AAG TTT GCT GTA GCT GTT TGT AAC AAC    6107
Pro Ala Asn Tyr Ser Asp Pro Lys Phe Ala Val Ala Val Cys Asn Asn
            2005                2010                2015
```

-continued

```
TAT CTG CAT GAG AAT TAC CCG ACG GTA GCA TCT TAT CAG ATC ACC GAC    6155
Tyr Leu His Glu Asn Tyr Pro Thr Val Ala Ser Tyr Gln Ile Thr Asp
                2020                2025                2030

GAG TAC GAT GCT TAC TTG GAT ATG GTA GAC GGG ACA GTC GCT TGC CTA    6203
Glu Tyr Asp Ala Tyr Leu Asp Met Val Asp Gly Thr Val Ala Cys Leu
                2035                2040                2045

GAT ACT GCA ACT TTT TGC CCC GCC AAG CTT AGA AGT TAC CCG AAA AGA    6251
Asp Thr Ala Thr Phe Cys Pro Ala Lys Leu Arg Ser Tyr Pro Lys Arg
                2050                2055                2060

CAC GAG TAT AGA GCC CCA AAC ATC CGC AGT GCG GTT CCA TCA GCG ATG    6299
His Glu Tyr Arg Ala Pro Asn Ile Arg Ser Ala Val Pro Ser Ala Met
2065                2070                2075                2080

CAG AAC ACG TTG CAA AAC GTG CTC ATT GCC GCG ACT AAA AGA AAC TGC    6347
Gln Asn Thr Leu Gln Asn Val Leu Ile Ala Ala Thr Lys Arg Asn Cys
                2085                2090                2095

AAC GTC ACA CAA ATG CGT GAA CTG CCA ACA CTG GAC TCA GCG ACA TTC    6395
Asn Val Thr Gln Met Arg Glu Leu Pro Thr Leu Asp Ser Ala Thr Phe
                2100                2105                2110

AAC GTT GAA TGC TTT CGA AAA TAT GCA TGC AAT GAC GAG TAT TGG GAG    6443
Asn Val Glu Cys Phe Arg Lys Tyr Ala Cys Asn Asp Glu Tyr Trp Glu
                2115                2120                2125

GAG TTT GCC CGA AAG CCA ATT AGG ATC ACT ACT GAG TTC GTT ACC GCA    6491
Glu Phe Ala Arg Lys Pro Ile Arg Ile Thr Thr Glu Phe Val Thr Ala
                2130                2135                2140

TAC GTG GCC AGA CTG AAA GGC CCT AAG GCC GCC GCA CTG TTC GCA AAG    6539
Tyr Val Ala Arg Leu Lys Gly Pro Lys Ala Ala Ala Leu Phe Ala Lys
2145                2150                2155                2160

ACG CAT AAT TTG GTC CCA TTG CAA GAA GTG CCT ATG GAT AGA TTC GTC    6587
Thr His Asn Leu Val Pro Leu Gln Glu Val Pro Met Asp Arg Phe Val
                2165                2170                2175

ATG GAC ATG AAA AGA GAC GTG AAA GTT ACA CCT GGC ACG AAA CAC ACA    6635
Met Asp Met Lys Arg Asp Val Lys Val Thr Pro Gly Thr Lys His Thr
                2180                2185                2190

GAA GAA AGA CCG AAA GTA CAA GTG ATA CAA GCC GCA GAA CCC CTG GCG    6683
Glu Glu Arg Pro Lys Val Gln Val Ile Gln Ala Ala Glu Pro Leu Ala
                2195                2200                2205

ACC GCT TAC CTA TGC GGG ATC CAC CGG GAG TTA GTG CGC AGG CTT ACA    6731
Thr Ala Tyr Leu Cys Gly Ile His Arg Glu Leu Val Arg Arg Leu Thr
                2210                2215                2220

GCC GTT TTG CTA CCC AAC ATT CAC ACG CTC TTT GAC ATG TCG GCG GAG    6779
Ala Val Leu Leu Pro Asn Ile His Thr Leu Phe Asp Met Ser Ala Glu
2225                2230                2235                2240

GAC TTT GAT GCA ATC ATA GCA GAA CAC TTC AAG CAA GGT GAC CCG GTA    6827
Asp Phe Asp Ala Ile Ile Ala Glu His Phe Lys Gln Gly Asp Pro Val
                2245                2250                2255

CTG GAG ACG GAT ATC GCC TCG TTC GAC AAA AGC CAA GAC GAC GCT ATG    6875
Leu Glu Thr Asp Ile Ala Ser Phe Asp Lys Ser Gln Asp Asp Ala Met
                2260                2265                2270

GCG TTA ACC GGC CTG ATG ATC TTG GAA GAC CTG GGT GTG GAC CAA CCA    6923
Ala Leu Thr Gly Leu Met Ile Leu Glu Asp Leu Gly Val Asp Gln Pro
                2275                2280                2285

CTA CTC GAC TTG ATC GAG TGC GCC TTT GGA GAA ATA TCA TCC ACC CAT    6971
Leu Leu Asp Leu Ile Glu Cys Ala Phe Gly Glu Ile Ser Ser Thr His
                2290                2295                2300

CTG CCC ACG GGT ACC CGT TTC AAA TTC GGG GCG ATG ATG AAA TCC GGA    7019
Leu Pro Thr Gly Thr Arg Phe Lys Phe Gly Ala Met Met Lys Ser Gly
2305                2310                2315                2320

ATG TTC CTC ACG CTC TTT GTC AAC ACA GTT CTG AAT GTC GTT ATC GCC    7067
Met Phe Leu Thr Leu Phe Val Asn Thr Val Leu Asn Val Val Ile Ala
                2325                2330                2335
```

```
AGC AGA GTA TTG GAG GAG CGG CTT AAA ACG TCC AAA TGT GCA GCA TTT       7115
Ser Arg Val Leu Glu Glu Arg Leu Lys Thr Ser Lys Cys Ala Ala Phe
            2340                2345                2350

ATC GGC GAC GAC AAC ATT ATA CAC GGA GTA GTA TCT GAC AAA GAA ATG       7163
Ile Gly Asp Asp Asn Ile Ile His Gly Val Val Ser Asp Lys Glu Met
            2355                2360                2365

GCT GAG AGG TGT GCC ACC TGG CTC AAC ATG GAG GTT AAG ATC ATT GAC       7211
Ala Glu Arg Cys Ala Thr Trp Leu Asn Met Glu Val Lys Ile Ile Asp
    2370                2375                2380

GCA GTC ATC GGC GAG AGA CCA CCT TAC TTC TGC GGT GGA TTC ATC TTG       7259
Ala Val Ile Gly Glu Arg Pro Pro Tyr Phe Cys Gly Gly Phe Ile Leu
2385                2390                2395                2400

CAA GAT TCG GTT ACC TCC ACA GCG TGT CGC GTG GCG GAC CCC TTG AAA       7307
Gln Asp Ser Val Thr Ser Thr Ala Cys Arg Val Ala Asp Pro Leu Lys
            2405                2410                2415

AGG CTG TTT AAG TTG GGT AAA CCG CTC CCA GCC GAC GAT GAG CAA GAC       7355
Arg Leu Phe Lys Leu Gly Lys Pro Leu Pro Ala Asp Asp Glu Gln Asp
            2420                2425                2430

GAA GAC AGA AGA CGC GCT CTG CTA GAT GAA ACA AAG GCG TGG TTT AGA       7403
Glu Asp Arg Arg Arg Ala Leu Leu Asp Glu Thr Lys Ala Trp Phe Arg
            2435                2440                2445

GTA GGT ATA ACA GAC ACC TTA GCA GTG GCC GTG GCA ACT CGG TAT GAG       7451
Val Gly Ile Thr Asp Thr Leu Ala Val Ala Val Ala Thr Arg Tyr Glu
            2450                2455                2460

GTA GAC AAC ATC ACA CCT GTC CTG CTG GCA TTG AGA ACT TTT GCC CAG       7499
Val Asp Asn Ile Thr Pro Val Leu Leu Ala Leu Arg Thr Phe Ala Gln
2465                2470                2475                2480

AGC AAA AGA GCA TTT CAA GCC ATC AGA GGG GAA ATA AAG CAT CTC TAC       7547
Ser Lys Arg Ala Phe Gln Ala Ile Arg Gly Glu Ile Lys His Leu Tyr
            2485                2490                2495

GGT GGT CCT AAA TAGTCAGCAT AGTACATTTC ATCTGACTAA TACCACAACA           7599
Gly Gly Pro Lys
        2500

CCACCACC ATG AAT AGA GGA TTC TTT AAC ATG CTC GGC CGC CGC CCC TTC      7649
         Met Asn Arg Gly Phe Phe Asn Met Leu Gly Arg Arg Pro Phe
          1               5                  10

CCA GCC CCC ACT GCC ATG TGG AGG CCG CGG AGA AGG AGG CAG GCG GCC       7697
Pro Ala Pro Thr Ala Met Trp Arg Pro Arg Arg Arg Arg Gln Ala Ala
 15              20                  25                  30

CCG ATG CCT GCC CGC AAT GGG CTG GCT TCC CAA ATC CAG CAA CTG ACC       7745
Pro Met Pro Ala Arg Asn Gly Leu Ala Ser Gln Ile Gln Gln Leu Thr
             35                  40                  45

ACA GCC GTC AGT GCC CTA GTC ATT GGA CAG GCA ACT AGA CCT CAA ACC       7793
Thr Ala Val Ser Ala Leu Val Ile Gly Gln Ala Thr Arg Pro Gln Thr
             50                  55                  60

CCA CGC CCA CGC CCG CCG CCG CGC CAG AAG AAG CAG GCG CCA AAG CAA       7841
Pro Arg Pro Arg Pro Pro Pro Arg Gln Lys Lys Gln Ala Pro Lys Gln
 65                  70                  75

CCA CCG AAG CCG AAG AAA CCA AAA ACA CAG GAG AAG AAG AAG AAG CAA       7889
Pro Pro Lys Pro Lys Lys Pro Lys Thr Gln Glu Lys Lys Lys Lys Gln
 80                  85                  90

CCT GCA AAA CCC AAA CCC GGA AAG AGA CAG CGT ATG GCA CTT AAG TTG       7937
Pro Ala Lys Pro Lys Pro Gly Lys Arg Gln Arg Met Ala Leu Lys Leu
 95                  100                 105                 110

GAG GCC GAC AGA CTG TTC GAC GTC AAA AAT GAG GAC GGA GAT GTC ATC       7985
Glu Ala Asp Arg Leu Phe Asp Val Lys Asn Glu Asp Gly Asp Val Ile
             115                 120                 125

GGG CAC GCA CTG GCC ATG GAA GGA AAG GTA ATG AAA CCA CTC CAC GTG       8033
Gly His Ala Leu Ala Met Glu Gly Lys Val Met Lys Pro Leu His Val
```

|  |  |  |  |  |  |  |  |  |  |  |  |  |  |  |  |
|---|---|---|---|---|---|---|---|---|---|---|---|---|---|---|---|
|  | 130 |  |  |  | 135 |  |  |  |  | 140 |  |  |  |  |  |
| AAA | GGA | ACT | ATT | GAC | CAC | CCT | GTG | CTA | TCA | AAG | CTC | AAA | TTC | ACC | AAG | 8081 |
| Lys | Gly | Thr | Ile | Asp | His | Pro | Val | Leu | Ser | Lys | Leu | Lys | Phe | Thr | Lys |  |
|  |  | 145 |  |  |  | 150 |  |  |  | 155 |  |  |  |  |  |  |
| TCG | TCA | GCA | TAC | GAC | ATG | GAG | TTC | GCA | CAG | TTG | CCG | GTC | AAC | ATG | AGA | 8129 |
| Ser | Ser | Ala | Tyr | Asp | Met | Glu | Phe | Ala | Gln | Leu | Pro | Val | Asn | Met | Arg |  |
| 160 |  |  |  |  | 165 |  |  |  |  | 170 |  |  |  |  |  |  |
| AGT | GAG | GCG | TTC | ACC | TAC | ACC | AGT | GAA | CAC | CCT | GAA | GGG | TTC | TAC | AAC | 8177 |
| Ser | Glu | Ala | Phe | Thr | Tyr | Thr | Ser | Glu | His | Pro | Glu | Gly | Phe | Tyr | Asn |  |
| 175 |  |  |  |  | 180 |  |  |  |  | 185 |  |  |  |  | 190 |  |
| TGG | CAC | CAC | GGA | GCG | GTG | CAG | TAT | AGT | GGA | GGC | AGA | TTT | ACC | ATC | CCC | 8225 |
| Trp | His | His | Gly | Ala | Val | Gln | Tyr | Ser | Gly | Gly | Arg | Phe | Thr | Ile | Pro |  |
|  |  |  |  | 195 |  |  |  | 200 |  |  |  | 205 |  |  |  |  |
| CGC | GGA | GTA | GGA | GGC | AGA | GGA | GAC | AGT | GGT | CGT | CCG | ATT | ATG | GAT | AAC | 8273 |
| Arg | Gly | Val | Gly | Gly | Arg | Gly | Asp | Ser | Gly | Arg | Pro | Ile | Met | Asp | Asn |  |
|  |  | 210 |  |  |  | 215 |  |  |  | 220 |  |  |  |  |  |  |
| TCA | GGC | CGG | GTT | GTC | GCG | ATA | GTC | CTC | GGA | GGG | GCT | GAT | GAG | GGA | ACA | 8321 |
| Ser | Gly | Arg | Val | Val | Ala | Ile | Val | Leu | Gly | Gly | Ala | Asp | Glu | Gly | Thr |  |
|  |  | 225 |  |  |  | 230 |  |  |  | 235 |  |  |  |  |  |  |
| AGA | ACC | GCC | CTT | TCG | GTC | GTC | ACC | TGG | AAT | AGC | AAA | GGG | AAG | ACA | ATC | 8369 |
| Arg | Thr | Ala | Leu | Ser | Val | Val | Thr | Trp | Asn | Ser | Lys | Gly | Lys | Thr | Ile |  |
| 240 |  |  |  |  | 245 |  |  |  |  | 250 |  |  |  |  |  |  |
| AAG | ACA | ACC | CCG | GAA | GGG | ACA | GAA | GAG | TGG | TCT | GCT | GCA | CCA | CTG | GTC | 8417 |
| Lys | Thr | Thr | Pro | Glu | Gly | Thr | Glu | Glu | Trp | Ser | Ala | Ala | Pro | Leu | Val |  |
| 255 |  |  |  |  | 260 |  |  |  |  | 265 |  |  |  |  | 270 |  |
| ACG | GCC | ATG | TGC | TTG | CTT | GGA | AAC | GTG | AGC | TTC | CCA | TGC | AAT | CGC | CCG | 8465 |
| Thr | Ala | Met | Cys | Leu | Leu | Gly | Asn | Val | Ser | Phe | Pro | Cys | Asn | Arg | Pro |  |
|  |  |  |  | 275 |  |  |  | 280 |  |  |  | 285 |  |  |  |  |
| CCC | ACA | TGC | TAC | ACC | CGC | GAA | CCA | TCC | AGA | GCT | CTC | GAC | ATC | CTC | GAA | 8513 |
| Pro | Thr | Cys | Tyr | Thr | Arg | Glu | Pro | Ser | Arg | Ala | Leu | Asp | Ile | Leu | Glu |  |
|  |  | 290 |  |  |  | 295 |  |  |  | 300 |  |  |  |  |  |  |
| GAG | AAC | GTG | AAC | CAC | GAG | GCC | TAC | GAC | ACC | CTG | CTC | AAC | GCC | ATA | TTG | 8561 |
| Glu | Asn | Val | Asn | His | Glu | Ala | Tyr | Asp | Thr | Leu | Leu | Asn | Ala | Ile | Leu |  |
|  |  | 305 |  |  |  | 310 |  |  |  | 315 |  |  |  |  |  |  |
| CGG | TGC | GGA | TCG | TCC | GGC | AGA | AGT | AAA | AGA | AGC | GTC | ACT | GAC | GAC | TTT | 8609 |
| Arg | Cys | Gly | Ser | Ser | Gly | Arg | Ser | Lys | Arg | Ser | Val | Thr | Asp | Asp | Phe |  |
|  | 320 |  |  |  |  | 325 |  |  |  | 330 |  |  |  |  |  |  |
| ACC | TTG | ACC | AGC | CCG | TAC | TTG | GGC | ACA | TGC | TCG | TAC | TGT | CAC | CAT | ACT | 8657 |
| Thr | Leu | Thr | Ser | Pro | Tyr | Leu | Gly | Thr | Cys | Ser | Tyr | Cys | His | His | Thr |  |
| 335 |  |  |  |  | 340 |  |  |  |  | 345 |  |  |  |  | 350 |  |
| GAA | CCG | TGC | TTT | AGC | CCG | ATT | AAG | ATC | GAG | CAG | GTC | TGG | GAT | GAA | GCG | 8705 |
| Glu | Pro | Cys | Phe | Ser | Pro | Ile | Lys | Ile | Glu | Gln | Val | Trp | Asp | Glu | Ala |  |
|  |  |  |  | 355 |  |  |  | 360 |  |  |  | 365 |  |  |  |  |
| GAC | GAC | AAC | ACC | ATA | CGC | ATA | CAG | ACT | TCC | GCC | CAG | TTT | GGA | TAC | GAC | 8753 |
| Asp | Asp | Asn | Thr | Ile | Arg | Ile | Gln | Thr | Ser | Ala | Gln | Phe | Gly | Tyr | Asp |  |
|  |  | 370 |  |  |  | 375 |  |  |  | 380 |  |  |  |  |  |  |
| CAA | AGC | GGA | GCA | GCA | AGC | TCA | AAT | AAG | TAC | CGC | TAC | ATG | TCG | CTC | GAG | 8801 |
| Gln | Ser | Gly | Ala | Ala | Ser | Ser | Asn | Lys | Tyr | Arg | Tyr | Met | Ser | Leu | Glu |  |
|  |  | 385 |  |  |  | 390 |  |  |  | 395 |  |  |  |  |  |  |
| CAG | GAT | CAT | ACT | GTC | AAA | GAA | GGC | ACC | ATG | GAT | GAC | ATC | AAG | ATC | AGC | 8849 |
| Gln | Asp | His | Thr | Val | Lys | Glu | Gly | Thr | Met | Asp | Asp | Ile | Lys | Ile | Ser |  |
| 400 |  |  |  |  | 405 |  |  |  |  | 410 |  |  |  |  |  |  |
| ACC | TCA | GGA | CCG | TGT | AGA | AGG | CTT | AGC | TAC | AAA | GGA | TAC | TTT | CTC | CTC | 8897 |
| Thr | Ser | Gly | Pro | Cys | Arg | Arg | Leu | Ser | Tyr | Lys | Gly | Tyr | Phe | Leu | Leu |  |
| 415 |  |  |  |  | 420 |  |  |  |  | 425 |  |  |  |  | 430 |  |
| GCG | AAG | TGT | CCT | CCA | GGG | GAC | AGC | GTA | ACG | GTT | AGC | ATA | GCA | AGT | AGC | 8945 |
| Ala | Lys | Cys | Pro | Pro | Gly | Asp | Ser | Val | Thr | Val | Ser | Ile | Ala | Ser | Ser |  |
|  |  |  |  | 435 |  |  |  | 440 |  |  |  | 445 |  |  |  |  |
| AAC | TCA | GCA | ACG | TCA | TGC | ACA | ATG | GCC | CGC | AAG | ATA | AAA | CCA | AAA | TTC | 8993 |
| Asn | Ser | Ala | Thr | Ser | Cys | Thr | Met | Ala | Arg | Lys | Ile | Lys | Pro | Lys | Phe |  |

-continued

|   |   |   |   |   | 450 |   |   |   | 455 |   |   |   | 460 |   |   |      |
|---|---|---|---|---|---|---|---|---|---|---|---|---|---|---|---|------|
| GTG | GGA | CGG | GAA | AAA | TAT | GAC | CTA | CCT | CCC | GTT | CAC | GGT | AAG | AAG | ATT | 9041 |
| Val | Gly | Arg | Glu | Lys | Tyr | Asp | Leu | Pro | Pro | Val | His | Gly | Lys | Lys | Ile |      |
|     |     | 465 |     |     |     | 470 |     |     |     | 475 |     |     |     |     |     |      |
| CCT | TGC | ACA | GTG | TAC | GAC | CGT | CTG | AAA | GAA | ACA | ACC | GCC | GGC | TAC | ATC | 9089 |
| Pro | Cys | Thr | Val | Tyr | Asp | Arg | Leu | Lys | Glu | Thr | Thr | Ala | Gly | Tyr | Ile |      |
|     | 480 |     |     |     |     | 485 |     |     |     | 490 |     |     |     |     |     |      |
| ACT | ATG | CAC | AGG | CCG | GGA | CCG | CAT | GCC | TAT | ACA | TCC | TAT | CTG | GAG | GAA | 9137 |
| Thr | Met | His | Arg | Pro | Gly | Pro | His | Ala | Tyr | Thr | Ser | Tyr | Leu | Glu | Glu |      |
| 495 |     |     |     | 500 |     |     |     | 505 |     |     |     |     |     |     | 510 |      |
| TCA | TCA | GGG | AAA | GTT | TAC | GCG | AAG | CCA | CCA | TCC | GGG | AAG | AAC | ATT | ACG | 9185 |
| Ser | Ser | Gly | Lys | Val | Tyr | Ala | Lys | Pro | Pro | Ser | Gly | Lys | Asn | Ile | Thr |      |
|     |     |     |     | 515 |     |     |     |     | 520 |     |     |     |     | 525 |     |      |
| TAC | GAG | TGC | AAG | TGC | GGC | GAT | TAC | AAG | ACC | GGA | ACC | GTT | ACG | ACC | CGT | 9233 |
| Tyr | Glu | Cys | Lys | Cys | Gly | Asp | Tyr | Lys | Thr | Gly | Thr | Val | Thr | Thr | Arg |      |
|     |     | 530 |     |     |     |     | 535 |     |     |     |     | 540 |     |     |     |      |
| ACC | GAA | ATC | ACG | GGC | TGC | ACC | GCC | ATC | AAG | CAG | TGC | GTC | GCC | TAT | AAG | 9281 |
| Thr | Glu | Ile | Thr | Gly | Cys | Thr | Ala | Ile | Lys | Gln | Cys | Val | Ala | Tyr | Lys |      |
|     | 545 |     |     |     |     | 550 |     |     |     |     | 555 |     |     |     |     |      |
| AGC | GAC | CAA | ACG | AAG | TGG | GTC | TTC | AAC | TCG | CCG | GAC | TCG | ATC | AGA | CAC | 9329 |
| Ser | Asp | Gln | Thr | Lys | Trp | Val | Phe | Asn | Ser | Pro | Asp | Ser | Ile | Arg | His |      |
| 560 |     |     |     |     | 565 |     |     |     |     | 570 |     |     |     |     |     |      |
| GCC | GAC | CAC | ACG | GCC | CAA | GGG | AAA | TTG | CAT | TTG | CCT | TTC | AAG | CTG | ATC | 9377 |
| Ala | Asp | His | Thr | Ala | Gln | Gly | Lys | Leu | His | Leu | Pro | Phe | Lys | Leu | Ile |      |
| 575 |     |     |     | 580 |     |     |     |     | 585 |     |     |     |     | 590 |     |      |
| CCG | AGT | ACC | TGC | ATG | GTC | CCT | GTT | GCC | CAC | GCG | CCG | AAC | GTA | GTA | CAC | 9425 |
| Pro | Ser | Thr | Cys | Met | Val | Pro | Val | Ala | His | Ala | Pro | Asn | Val | Val | His |      |
|     |     |     | 595 |     |     |     | 600 |     |     |     |     | 605 |     |     |     |      |
| GGC | TTT | AAA | CAC | ATC | AGC | CTC | CAA | TTA | GAC | ACA | GAC | CAT | CTG | ACA | TTG | 9473 |
| Gly | Phe | Lys | His | Ile | Ser | Leu | Gln | Leu | Asp | Thr | Asp | His | Leu | Thr | Leu |      |
|     |     |     | 610 |     |     |     | 615 |     |     |     | 620 |     |     |     |     |      |
| CTC | ACC | ACC | AGG | AGA | CTA | GGG | GCA | AAC | CCG | GAA | CCA | ACC | ACT | GAA | TGG | 9521 |
| Leu | Thr | Thr | Arg | Arg | Leu | Gly | Ala | Asn | Pro | Glu | Pro | Thr | Thr | Glu | Trp |      |
|     |     | 625 |     |     |     | 630 |     |     |     |     | 635 |     |     |     |     |      |
| ATC | ATC | GGA | AAC | ACG | GTT | AGA | AAC | TTC | ACC | GTC | GAC | CGA | GAT | GGC | CTG | 9569 |
| Ile | Ile | Gly | Asn | Thr | Val | Arg | Asn | Phe | Thr | Val | Asp | Arg | Asp | Gly | Leu |      |
|     | 640 |     |     |     | 645 |     |     |     | 650 |     |     |     |     |     |     |      |
| GAA | TAC | ATA | TGG | GGC | AAT | CAC | GAA | CCA | GTA | AGG | GTC | TAT | GCC | CAA | GAG | 9617 |
| Glu | Tyr | Ile | Trp | Gly | Asn | His | Glu | Pro | Val | Arg | Val | Tyr | Ala | Gln | Glu |      |
| 655 |     |     |     | 660 |     |     |     | 665 |     |     |     |     |     | 670 |     |      |
| TCT | GCA | CCA | GGA | GAC | CCT | CAC | GGA | TGG | CCA | CAC | GAA | ATA | GTA | CAG | CAT | 9665 |
| Ser | Ala | Pro | Gly | Asp | Pro | His | Gly | Trp | Pro | His | Glu | Ile | Val | Gln | His |      |
|     |     |     | 675 |     |     |     | 680 |     |     |     |     | 685 |     |     |     |      |
| TAC | TAT | CAT | CGC | CAT | CCT | GTG | TAC | ACC | ATC | TTA | GCC | GTC | GCA | TCA | GCT | 9713 |
| Tyr | Tyr | His | Arg | His | Pro | Val | Tyr | Thr | Ile | Leu | Ala | Val | Ala | Ser | Ala |      |
|     |     | 690 |     |     |     |     | 695 |     |     |     | 700 |     |     |     |     |      |
| GCT | GTG | GCG | ATG | ATG | ATT | GGC | GTA | ACT | GTT | GCA | GCA | TTA | TGT | GCC | TGT | 9761 |
| Ala | Val | Ala | Met | Met | Ile | Gly | Val | Thr | Val | Ala | Ala | Leu | Cys | Ala | Cys |      |
|     | 705 |     |     |     |     | 710 |     |     |     |     | 715 |     |     |     |     |      |
| AAA | GCG | CGC | CGT | GAG | TGC | CTG | ACG | CCA | TAT | GCC | CTG | GCC | CCA | AAT | GCC | 9809 |
| Lys | Ala | Arg | Arg | Glu | Cys | Leu | Thr | Pro | Tyr | Ala | Leu | Ala | Pro | Asn | Ala |      |
|     | 720 |     |     |     |     | 725 |     |     |     | 730 |     |     |     |     |     |      |
| GTG | ATT | CCA | ACT | TCG | CTG | GCA | CTT | TTG | TGC | TGT | GTT | AGG | TCG | GCT | AAT | 9857 |
| Val | Ile | Pro | Thr | Ser | Leu | Ala | Leu | Leu | Cys | Cys | Val | Arg | Ser | Ala | Asn |      |
| 735 |     |     |     | 740 |     |     |     |     | 745 |     |     |     |     | 750 |     |      |
| GCT | GAA | ACA | TTC | ACC | GAG | ACC | ATG | AGT | TAC | TTA | TGG | TCG | AAC | AGC | CAG | 9905 |
| Ala | Glu | Thr | Phe | Thr | Glu | Thr | Met | Ser | Tyr | Leu | Trp | Ser | Asn | Ser | Gln |      |
|     |     |     |     | 755 |     |     |     | 760 |     |     |     |     | 765 |     |     |      |
| CCG | TTC | TTC | TGG | GTC | CAG | CTG | TGT | ATA | CCT | CTG | GCC | GCT | GTC | GTC | GTT | 9953 |
| Pro | Phe | Phe | Trp | Val | Gln | Leu | Cys | Ile | Pro | Leu | Ala | Ala | Val | Val | Val |      |

-continued

```
                 770                 775                 780
CTA ATG CGC TGT TGC TCA TGC TGC CTG CCT TTT TTA GTG GTT GCC GGC           10001
Leu Met Arg Cys Cys Ser Cys Cys Leu Pro Phe Leu Val Val Ala Gly
        785                 790                 795

GCC TAC CTG GCG AAG GTA GAC GCC TAC GAA CAT GCG ACC ACT GTT CCA           10049
Ala Tyr Leu Ala Lys Val Asp Ala Tyr Glu His Ala Thr Thr Val Pro
        800                 805                 810

AAT GTG CCA CAG ATA CCG TAT AAG GCA CTT GTT GAA AGG GCA GGG TAC           10097
Asn Val Pro Gln Ile Pro Tyr Lys Ala Leu Val Glu Arg Ala Gly Tyr
815                 820                 825                 830

GCC CCG CTC AAT TTG GAG ATT ACT GTC ATG TCC TCG GAG GTT TTG CCT           10145
Ala Pro Leu Asn Leu Glu Ile Thr Val Met Ser Ser Glu Val Leu Pro
        835                 840                 845

TCC ACC AAC CAA GAG TAC ATT ACC TGC AAA TTC ACC ACT GTG GTC CCC           10193
Ser Thr Asn Gln Glu Tyr Ile Thr Cys Lys Phe Thr Thr Val Val Pro
        850                 855                 860

TCC CCT AAA GTC AGA TGC TGC GGC TCC TTG GAA TGT CAG CCC GCC GCT           10241
Ser Pro Lys Val Arg Cys Cys Gly Ser Leu Glu Cys Gln Pro Ala Ala
        865                 870                 875

CAC GCA GAC TAT ACC TGC AAG GTC TTT GGA GGG GTG TAC CCC TTC ATG           10289
His Ala Asp Tyr Thr Cys Lys Val Phe Gly Gly Val Tyr Pro Phe Met
880                 885                 890

TGG GGA GGA GCA CAA TGT TTT TGC GAC AGT GAG AAC AGC CAG ATG AGT           10337
Trp Gly Gly Ala Gln Cys Phe Cys Asp Ser Glu Asn Ser Gln Met Ser
895                 900                 905                 910

GAG GCG TAC GTC GAA TTG TCA GTA GAT TGC GCG ACT GAC CAC GCG CAG           10385
Glu Ala Tyr Val Glu Leu Ser Val Asp Cys Ala Thr Asp His Ala Gln
        915                 920                 925

GCG ATT AAG GTG CAT ACT GCC GCG ATG AAA GTA GGA CTG CGT ATA GTG           10433
Ala Ile Lys Val His Thr Ala Ala Met Lys Val Gly Leu Arg Ile Val
        930                 935                 940

TAC GGG AAC ACT ACC AGT TTC CTA GAT GTG TAC GTG AAC GGA GTC ACA           10481
Tyr Gly Asn Thr Thr Ser Phe Leu Asp Val Tyr Val Asn Gly Val Thr
        945                 950                 955

CCA GGA ACG TCT AAA GAC CTG AAA GTC ATA GCT GGA CCA ATT TCA GCA           10529
Pro Gly Thr Ser Lys Asp Leu Lys Val Ile Ala Gly Pro Ile Ser Ala
        960                 965                 970

TTG TTT ACA CCA TTC GAT CAC AAG GTC GTT ATC AAT CGC GGC CTG GTG           10577
Leu Phe Thr Pro Phe Asp His Lys Val Val Ile Asn Arg Gly Leu Val
975                 980                 985                 990

TAC AAC TAT GAC TTT CCG GAA TAC GGA GCG ATG AAA CCA GGA GCG TTT           10625
Tyr Asn Tyr Asp Phe Pro Glu Tyr Gly Ala Met Lys Pro Gly Ala Phe
            995                 1000                1005

GGA GAC ATT CAA GCT ACC TCC TTG ACT AGC AAA GAC CTC ATC GCC AGC           10673
Gly Asp Ile Gln Ala Thr Ser Leu Thr Ser Lys Asp Leu Ile Ala Ser
            1010                1015                1020

ACA GAC ATT AGG CTA CTC AAG CCT TCC GCC AAG AAC GTG CAT GTC CCG           10721
Thr Asp Ile Arg Leu Leu Lys Pro Ser Ala Lys Asn Val His Val Pro
            1025                1030                1035

TAC ACG CAG GCC GCA TCT GGA TTC GAG ATG TGG AAA AAC AAC TCA GGC           10769
Tyr Thr Gln Ala Ala Ser Gly Phe Glu Met Trp Lys Asn Asn Ser Gly
            1040                1045                1050

CGC CCA CTG CAG GAA ACC GCC CCT TTT GGG TGC AAG ATT GCA GTC AAT           10817
Arg Pro Leu Gln Glu Thr Ala Pro Phe Gly Cys Lys Ile Ala Val Asn
1055                1060                1065                1070

CCG CTT CGA GCG GTG GAC TGC TCA TAC GGG AAC ATT CCC ATT TCT ATT           10865
Pro Leu Arg Ala Val Asp Cys Ser Tyr Gly Asn Ile Pro Ile Ser Ile
            1075                1080                1085

GAC ATC CCG AAC GCT GCC TTT ATC AGG ACA TCA GAT GCA CCA CTG GTC           10913
Asp Ile Pro Asn Ala Ala Phe Ile Arg Thr Ser Asp Ala Pro Leu Val
```

```
                    1090              1095              1100
TCA ACA GTC AAA TGT GAT GTC AGT GAG TGC ACT TAT TCA GCG GAC TTC     10961
Ser Thr Val Lys Cys Asp Val Ser Glu Cys Thr Tyr Ser Ala Asp Phe
        1105              1110              1115

GGA GGG ATG GCT ACC CTG CAG TAT GTA TCC GAC CGC GAA GGA CAA TGC     11009
Gly Gly Met Ala Thr Leu Gln Tyr Val Ser Asp Arg Glu Gly Gln Cys
        1120              1125              1130

CCT GTA CAT TCG CAT TCG AGC ACA GCA ACC CTC CAA GAG TCG ACA GTT     11057
Pro Val His Ser His Ser Ser Thr Ala Thr Leu Gln Glu Ser Thr Val
1135              1140              1145              1150

CAT GTC CTG GAG AAA GGA GCG GTG ACA GTA CAC TTC AGC ACC GCG AGC     11105
His Val Leu Glu Lys Gly Ala Val Thr Val His Phe Ser Thr Ala Ser
            1155              1160              1165

CCA CAG GCG AAC TTC ATT GTA TCG CTG TGT GGT AAG AAG ACA ACA TGC     11153
Pro Gln Ala Asn Phe Ile Val Ser Leu Cys Gly Lys Lys Thr Thr Cys
        1170              1175              1180

AAT GCA GAA TGC AAA CCA CCA GCT GAT CAT ATC GTG AGC ACC CCG CAC     11201
Asn Ala Glu Cys Lys Pro Pro Ala Asp His Ile Val Ser Thr Pro His
        1185              1190              1195

AAA AAT GAC CAA GAA TTC CAA GCC GCC ATC TCA AAA ACT TCA TGG AGT     11249
Lys Asn Asp Gln Glu Phe Gln Ala Ala Ile Ser Lys Thr Ser Trp Ser
1200              1205              1210

TGG CTG TTT GCC CTT TTC GGC GGC GCC TCG TCG CTA TTA ATT ATA GGA     11297
Trp Leu Phe Ala Leu Phe Gly Gly Ala Ser Ser Leu Leu Ile Ile Gly
1215              1220              1225              1230

CTT ATG ATT TTT GCT TGC AGC ATG ATG CTG ACT AGC ACA CGA AGA          11342
Leu Met Ile Phe Ala Cys Ser Met Met Leu Thr Ser Thr Arg Arg
                1235              1240              1245

TGACCGCTAC GCCCCAATGA CCCGACCAGC AAAACTCGAT GTACTTCCGA GGAACTGATG   11402

TGCATAATGC ATCAGGCTGG TATATTAGAT CCCCGCTTAC CGCGGGCAAT ATAGCAACAC   11462

CAAAACTCGA CGTATTTCCG AGGAAGCGCA GTGCATAATG CTGCGCAGTG TTGCCAAATA   11522

ATCACTATAT TAACCATTTA TTCAGCGGAC GCCAAAACTC AATGTATTTC TGAGGAAGCA   11582

TGGTGCATAA TGCCATGCAG CGTCTGCATA ACTTTTTATT ATTTCTTTTA TTAATCAACA   11642

AAATTTTGTT TTTAACATTT C                                              11663

(2) INFORMATION FOR SEQ ID NO:2:

(i) SEQUENCE CHARACTERISTICS:
        (A) LENGTH: 2500 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Lys Pro Val Val Asn Val Asp Val Asp Pro Gln Ser Pro Phe
 1               5                  10                  15

Val Val Gln Leu Gln Lys Ser Phe Pro Gln Phe Glu Val Val Ala Gln
            20                  25                  30

Gln Val Thr Pro Asn Asp His Ala Asn Ala Arg Ala Phe Ser His Leu
        35                  40                  45

Ala Ser Lys Leu Ile Glu Leu Glu Val Pro Thr Thr Ala Thr Ile Leu
    50                  55                  60

Asp Ile Gly Ser Ala Pro Ala Arg Arg Met Phe Ser Glu His Gln Tyr
65                  70                  75                  80

His Cys Val Cys Pro Met Arg Ser Pro Glu Asp Pro Asp Arg Met Met
                85                  90                  95
```

-continued

```
Lys Tyr Ala Ser Lys Leu Ala Glu Lys Ala Cys Lys Ile Thr Asn Lys
            100                 105                 110

Asn Leu His Glu Lys Ile Lys Asp Leu Arg Thr Val Leu Asp Thr Pro
            115                 120                 125

Asp Ala Glu Thr Pro Ser Leu Cys Phe His Asn Asp Val Thr Cys Asn
            130                 135                 140

Thr Arg Ala Glu Tyr Ser Val Met Gln Asp Val Tyr Ile Asn Ala Pro
145                 150                 155                 160

Gly Thr Ile Tyr His Gln Ala Met Lys Gly Val Arg Thr Leu Tyr Trp
                    165                 170                 175

Ile Gly Phe Asp Thr Thr Gln Phe Met Phe Ser Ala Met Ala Gly Ser
                    180                 185                 190

Tyr Pro Ala Tyr Asn Thr Asn Trp Ala Asp Glu Lys Val Leu Glu Ala
            195                 200                 205

Arg Asn Ile Gly Leu Cys Ser Thr Lys Leu Ser Glu Gly Arg Thr Gly
            210                 215                 220

Lys Leu Ser Ile Met Arg Lys Glu Leu Lys Pro Gly Ser Arg Val
225                 230                 235                 240

Tyr Phe Ser Val Gly Ser Thr Leu Tyr Pro Glu His Arg Ala Ser Leu
                    245                 250                 255

Gln Ser Trp His Leu Pro Ser Val Phe His Leu Lys Gly Lys Gln Ser
            260                 265                 270

Tyr Thr Cys Arg Cys Asp Thr Val Val Ser Cys Glu Gly Tyr Val Val
            275                 280                 285

Lys Lys Ile Thr Ile Ser Pro Gly Ile Thr Gly Glu Thr Val Gly Tyr
290                 295                 300

Ala Val Thr Asn Asn Ser Glu Gly Phe Leu Leu Cys Lys Val Thr Asp
305                 310                 315                 320

Thr Val Lys Gly Glu Arg Val Ser Phe Pro Val Cys Thr Tyr Ile Pro
                    325                 330                 335

Ala Thr Ile Cys Asp Gln Met Thr Gly Ile Met Ala Thr Asp Ile Ser
                    340                 345                 350

Pro Asp Asp Ala Gln Lys Leu Leu Val Gly Leu Asn Gln Arg Ile Val
            355                 360                 365

Ile Asn Gly Lys Thr Asn Arg Asn Thr Asn Thr Met Gln Asn Tyr Leu
370                 375                 380

Leu Pro Ile Ile Ala Gln Gly Phe Ser Lys Trp Ala Lys Glu Arg Lys
385                 390                 395                 400

Glu Asp Leu Asp Asn Glu Lys Met Leu Gly Thr Arg Glu Arg Lys Leu
                    405                 410                 415

Thr Tyr Gly Cys Leu Trp Ala Phe Arg Thr Lys Lys Val His Ser Phe
                    420                 425                 430

Tyr Arg Pro Pro Gly Thr Gln Thr Ile Val Lys Val Pro Ala Ser Phe
            435                 440                 445

Ser Ala Phe Pro Met Ser Ser Val Trp Thr Thr Ser Leu Pro Met Ser
450                 455                 460

Leu Arg Gln Lys Met Lys Leu Ala Leu Gln Pro Lys Lys Glu Glu Lys
465                 470                 475                 480

Leu Leu Gln Val Pro Glu Glu Leu Val Met Glu Ala Lys Ala Ala Phe
                    485                 490                 495

Glu Asp Ala Gln Glu Glu Ser Arg Ala Glu Lys Leu Arg Glu Ala Leu
            500                 505                 510

Pro Pro Leu Val Ala Asp Lys Gly Ile Glu Ala Ala Glu Val Val
            515                 520                 525
```

```
Cys Glu Val Glu Gly Leu Gln Ala Asp Thr Gly Ala Ala Leu Val Glu
            530                 535                 540
Thr Pro Arg Gly His Val Arg Ile Ile Pro Gln Ala Asn Asp Arg Met
545                 550                 555                 560
Ile Gly Gln Tyr Ile Val Val Ser Pro Ile Ser Val Leu Lys Asn Ala
                565                 570                 575
Lys Leu Ala Pro Ala His Pro Leu Ala Asp Gln Val Lys Ile Ile Thr
            580                 585                 590
His Ser Gly Arg Ser Gly Arg Tyr Ala Val Glu Pro Tyr Asp Ala Lys
        595                 600                 605
Val Leu Met Pro Ala Gly Ser Ala Val Pro Trp Pro Glu Phe Leu Ala
610                 615                 620
Leu Ser Glu Ser Ala Thr Leu Val Tyr Asn Glu Arg Glu Phe Val Asn
625                 630                 635                 640
Arg Lys Leu Tyr His Ile Ala Met His Gly Pro Ala Lys Asn Thr Glu
                645                 650                 655
Glu Glu Gln Tyr Lys Val Thr Lys Ala Glu Leu Ala Glu Thr Glu Tyr
            660                 665                 670
Val Phe Asp Val Asp Lys Lys Arg Cys Val Lys Lys Glu Glu Ala Ser
        675                 680                 685
Gly Leu Val Leu Ser Gly Glu Leu Thr Asn Pro Pro Tyr His Glu Leu
690                 695                 700
Ala Leu Glu Gly Leu Lys Thr Arg Pro Ala Val Pro Tyr Lys Val Glu
705                 710                 715                 720
Thr Ile Gly Val Ile Gly Thr Pro Gly Ser Gly Lys Ser Ala Ile Ile
                725                 730                 735
Lys Ser Thr Val Thr Ala Arg Asp Leu Val Thr Ser Gly Lys Lys Glu
            740                 745                 750
Asn Cys Arg Glu Ile Glu Ala Asp Val Leu Arg Leu Arg Gly Met Gln
        755                 760                 765
Ile Thr Ser Lys Thr Val Asp Ser Val Met Leu Asn Gly Cys His Lys
770                 775                 780
Ala Val Glu Val Leu Tyr Val Asp Glu Ala Phe Arg Cys His Ala Gly
785                 790                 795                 800
Ala Leu Leu Ala Leu Ile Ala Ile Val Arg Pro Arg Lys Lys Val Val
                805                 810                 815
Leu Cys Gly Asp Pro Lys Gln Cys Gly Phe Phe Asn Met Met Gln Leu
            820                 825                 830
Lys Val His Phe Asn His Pro Glu Lys Asp Ile Cys Thr Lys Thr Phe
        835                 840                 845
Tyr Lys Phe Ile Ser Arg Arg Cys Thr Gln Pro Val Thr Ala Ile Val
850                 855                 860
Ser Thr Leu His Tyr Asp Gly Lys Met Lys Thr Thr Asn Pro Cys Lys
865                 870                 875                 880
Lys Asn Ile Glu Ile Asp Ile Thr Gly Ala Thr Lys Pro Lys Pro Gly
                885                 890                 895
Asp Ile Ile Leu Thr Cys Phe Arg Gly Trp Val Lys Gln Leu Gln Ile
            900                 905                 910
Asp Tyr Pro Gly His Glu Val Met Thr Ala Ala Ala Ser Gln Gly Leu
        915                 920                 925
Thr Arg Lys Gly Val Tyr Ala Val Arg Gln Lys Val Asn Glu Asn Pro
930                 935                 940
Leu Tyr Ala Ile Thr Ser Glu His Val Asn Val Leu Leu Thr Arg Thr
```

```
945             950             955             960
Glu Asp Arg Leu Val Trp Lys Thr Leu Gln Gly Asp Pro Trp Ile Lys
                965             970             975

Gln Leu Thr Asn Val Pro Lys Gly Asn Phe Gln Ala Thr Ile Glu Asp
            980             985             990

Trp Glu Ala Glu His Lys Gly Ile Ile Ala Ala Ile Asn Ser Pro Ala
        995            1000            1005

Pro Arg Thr Asn Pro Phe Ser Cys Lys Thr Asn Val Cys Trp Ala Lys
       1010            1015            1020

Ala Leu Glu Pro Ile Leu Ala Thr Ala Gly Ile Val Leu Thr Gly Cys
   1025            1030            1035            1040

Gln Trp Ser Glu Leu Phe Pro Gln Phe Ala Asp Asp Lys Pro His Ser
                1045            1050            1055

Ala Ile Tyr Ala Leu Asp Val Ile Cys Ile Lys Phe Phe Gly Met Asp
                1060            1065            1070

Leu Thr Ser Gly Leu Phe Ser Lys Gln Ser Ile Pro Leu Thr Tyr His
                1075            1080            1085

Pro Ala Asp Ser Ala Arg Pro Val Ala His Trp Asp Asn Ser Pro Gly
       1090            1095            1100

Thr Arg Lys Tyr Gly Tyr Asp His Ala Val Ala Glu Leu Ser Arg
1105            1110            1115            1120

Arg Phe Pro Val Phe Gln Leu Ala Gly Lys Gly Thr Gln Leu Asp Leu
                1125            1130            1135

Gln Thr Gly Arg Thr Arg Val Ile Ser Ala Gln His Asn Leu Val Pro
            1140            1145            1150

Val Asn Arg Asn Leu Pro His Ala Leu Val Pro Glu His Lys Glu Lys
                1155            1160            1165

Gln Pro Gly Pro Val Glu Lys Phe Leu Ser Gln Phe Lys His His Ser
        1170            1175            1180

Val Leu Val Ile Ser Glu Lys Lys Ile Glu Ala Pro His Lys Arg Ile
1185            1190            1195            1200

Glu Trp Ile Ala Pro Ile Gly Ile Ala Gly Ala Asp Lys Asn Tyr Asn
                1205            1210            1215

Leu Ala Phe Gly Phe Pro Pro Gln Ala Arg Tyr Asp Leu Val Phe Ile
                1220            1225            1230

Asn Ile Gly Thr Lys Tyr Arg Asn His His Phe Gln Gln Cys Glu Asp
                1235            1240            1245

His Ala Ala Thr Leu Lys Thr Leu Ser Arg Ser Ala Leu Asn Cys Leu
        1250            1255            1260

Asn Pro Gly Gly Thr Leu Val Val Lys Ser Tyr Gly Tyr Ala Asp Arg
1265            1270            1275            1280

Asn Ser Glu Asp Val Val Thr Ala Leu Ala Arg Lys Phe Val Arg Val
                1285            1290            1295

Ser Ala Ala Arg Pro Glu Cys Val Ser Ser Asn Thr Glu Met Tyr Leu
            1300            1305            1310

Ile Phe Arg Gln Leu Asp Asn Ser Arg Thr Arg Gln Phe Thr Pro His
        1315            1320            1325

His Leu Asn Cys Val Ile Ser Ser Val Tyr Glu Gly Thr Arg Asp Gly
        1330            1335            1340

Val Gly Ala Ala Pro Ser Tyr Arg Thr Lys Arg Glu Asn Ile Ala Asp
1345            1350            1355            1360

Cys Gln Glu Glu Ala Val Val Asn Ala Ala Asn Pro Leu Gly Arg Pro
                1365            1370            1375
```

-continued

```
Gly Glu Gly Val Cys Arg Ala Ile Tyr Lys Arg Trp Pro Asn Ser Phe
            1380                1385                1390

Thr Asp Ser Ala Thr Glu Thr Gly Thr Ala Lys Leu Thr Val Cys Gln
        1395                1400                1405

Gly Lys Lys Val Ile His Ala Val Gly Pro Asp Phe Arg Lys His Pro
        1410                1415                1420

Glu Ala Glu Ala Leu Lys Leu Leu Gln Asn Ala Tyr His Ala Val Ala
1425                1430                1435                1440

Asp Leu Val Asn Glu His Asn Ile Lys Ser Val Ala Ile Pro Leu Leu
            1445                1450                1455

Ser Thr Gly Ile Tyr Ala Ala Gly Lys Asp Arg Leu Glu Val Ser Leu
            1460                1465                1470

Asn Cys Leu Thr Thr Ala Leu Asp Arg Thr Asp Ala Asp Val Thr Ile
            1475                1480                1485

Tyr Cys Leu Asp Lys Lys Trp Lys Glu Arg Ile Asp Ala Val Leu Gln
            1490                1495                1500

Leu Lys Glu Ser Val Thr Glu Leu Lys Asp Glu Asp Met Glu Ile Asp
1505                1510                1515                1520

Asp Glu Leu Val Trp Ile His Pro Asp Ser Cys Leu Lys Gly Arg Lys
            1525                1530                1535

Gly Phe Ser Thr Thr Lys Gly Lys Leu Tyr Ser Tyr Phe Glu Gly Thr
            1540                1545                1550

Lys Phe His Gln Ala Ala Lys Asp Met Ala Glu Ile Lys Val Leu Phe
            1555                1560                1565

Pro Asn Asp Gln Glu Ser Asn Glu Gln Leu Cys Ala Tyr Ile Leu Gly
            1570                1575                1580

Glu Thr Met Glu Ala Ile Arg Glu Lys Cys Pro Val Asp His Asn Pro
1585                1590                1595                1600

Ser Ser Ser Pro Pro Lys Thr Leu Pro Cys Leu Cys Met Tyr Ala Met
            1605                1610                1615

Thr Pro Glu Arg Val His Arg Leu Arg Ser Asn Asn Val Lys Glu Val
            1620                1625                1630

Thr Val Cys Ser Ser Thr Pro Leu Pro Lys Tyr Lys Ile Lys Asn Val
            1635                1640                1645

Gln Lys Val Gln Cys Thr Lys Val Val Leu Phe Asn Pro His Thr Pro
            1650                1655                1660

Ala Phe Val Pro Ala Arg Lys Tyr Ile Glu Ala Pro Glu Gln Pro Ala
1665                1670                1675                1680

Ala Pro Pro Ala Gln Ala Glu Glu Ala Pro Gly Val Val Ala Thr Pro
            1685                1690                1695

Thr Pro Pro Ala Ala Asp Asn Thr Ser Leu Asp Val Thr Asp Ile Ser
            1700                1705                1710

Leu Asp Met Glu Asp Ser Ser Glu Gly Ser Leu Phe Ser Ser Phe Ser
            1715                1720                1725

Gly Ser Asp Asn Tyr Arg Arg Gln Val Val Ala Asp Val His Ala
            1730                1735                1740

Val Gln Glu Pro Ala Pro Val Pro Pro Arg Leu Lys Lys Met Ala
1745                1750                1755                1760

Arg Leu Ala Ala Ala Arg Met Gln Glu Glu Pro Thr Pro Pro Ala Ser
            1765                1770                1775

Thr Ser Ser Ala Asp Glu Ser Leu His Leu Ser Phe Asp Gly Val Ser
            1780                1785                1790

Ile Ser Phe Gly Ser Leu Phe Asp Gly Glu Met Ala Arg Leu Ala Ala
            1795                1800                1805
```

-continued

Ala Gln Pro Pro Ala Ser Thr Cys Pro Thr Asp Val Pro Met Ser Phe
    1810                1815                1820

Gly Ser Phe Ser Asp Gly Glu Ile Glu Glu Leu Ser Arg Arg Val Thr
1825                1830                1835                1840

Glu Ser Glu Pro Val Leu Phe Gly Ser Phe Glu Pro Gly Glu Val Asn
            1845                1850                1855

Ser Ile Ile Ser Ser Arg Ser Ala Val Ser Phe Pro Pro Arg Lys Gln
        1860                1865                1870

Arg Arg Arg Arg Arg Ser Arg Arg Thr Glu Tyr Cys Leu Thr Gly Val
    1875                1880                1885

Gly Gly Tyr Ile Phe Ser Thr Asp Thr Gly Pro Gly His Leu Gln Lys
    1890                1895                1900

Lys Ser Val Leu Gln Asn Gln Leu Thr Glu Pro Thr Leu Glu Arg Asn
1905                1910                1915                1920

Val Leu Glu Arg Ile Tyr Ala Pro Val Leu Asp Thr Ser Lys Glu Glu
            1925                1930                1935

Gln Leu Lys Leu Arg Tyr Gln Met Met Pro Thr Glu Ala Asn Lys Ser
        1940                1945                1950

Arg Tyr Gln Ser Arg Lys Val Glu Asn Gln Lys Ala Ile Thr Thr Glu
    1955                1960                1965

Arg Leu Leu Ser Gly Leu Arg Leu Tyr Asn Ser Ala Thr Asp Gln Pro
1970                1975                1980

Glu Cys Tyr Lys Ile Thr Tyr Pro Lys Pro Ser Tyr Ser Ser Ser Val
1985                1990                1995                2000

Pro Ala Asn Tyr Ser Asp Pro Lys Phe Ala Val Ala Val Cys Asn Asn
            2005                2010                2015

Tyr Leu His Glu Asn Tyr Pro Thr Val Ala Ser Tyr Gln Ile Thr Asp
        2020                2025                2030

Glu Tyr Asp Ala Tyr Leu Asp Met Val Asp Gly Thr Val Ala Cys Leu
    2035                2040                2045

Asp Thr Ala Thr Phe Cys Pro Ala Lys Leu Arg Ser Tyr Pro Lys Arg
    2050                2055                2060

His Glu Tyr Arg Ala Pro Asn Ile Arg Ser Ala Val Pro Ser Ala Met
2065                2070                2075                2080

Gln Asn Thr Leu Gln Asn Val Leu Ile Ala Ala Thr Lys Arg Asn Cys
            2085                2090                2095

Asn Val Thr Gln Met Arg Glu Leu Pro Thr Leu Asp Ser Ala Thr Phe
        2100                2105                2110

Asn Val Glu Cys Phe Arg Lys Tyr Ala Cys Asn Asp Glu Tyr Trp Glu
    2115                2120                2125

Glu Phe Ala Arg Lys Pro Ile Arg Ile Thr Thr Glu Phe Val Thr Ala
    2130                2135                2140

Tyr Val Ala Arg Leu Lys Gly Pro Lys Ala Ala Ala Leu Phe Ala Lys
2145                2150                2155                2160

Thr His Asn Leu Val Pro Leu Gln Glu Val Pro Met Asp Arg Phe Val
            2165                2170                2175

Met Asp Met Lys Arg Asp Val Lys Val Thr Pro Gly Thr Lys His Thr
        2180                2185                2190

Glu Glu Arg Pro Lys Val Gln Val Ile Gln Ala Ala Glu Pro Leu Ala
    2195                2200                2205

Thr Ala Tyr Leu Cys Gly Ile His Arg Glu Leu Val Arg Arg Leu Thr
    2210                2215                2220

Ala Val Leu Leu Pro Asn Ile His Thr Leu Phe Asp Met Ser Ala Glu

```
                      2225                2230                2235                2240

Asp Phe Asp Ala Ile Ala Glu His Phe Lys Gln Gly Asp Pro Val
                    2245                2250                2255

Leu Glu Thr Asp Ile Ala Ser Phe Asp Lys Ser Gln Asp Ala Met
                2260                2265                2270

Ala Leu Thr Gly Leu Met Ile Leu Glu Asp Leu Gly Val Asp Gln Pro
            2275                2280                2285

Leu Leu Asp Leu Ile Glu Cys Ala Phe Gly Glu Ile Ser Ser Thr His
        2290                2295                2300

Leu Pro Thr Gly Thr Arg Phe Lys Phe Gly Ala Met Met Lys Ser Gly
2305                2310                2315                2320

Met Phe Leu Thr Leu Phe Val Asn Thr Val Leu Asn Val Val Ile Ala
                2325                2330                2335

Ser Arg Val Leu Glu Glu Arg Leu Lys Thr Ser Lys Cys Ala Ala Phe
                2340                2345                2350

Ile Gly Asp Asp Asn Ile Ile His Gly Val Val Ser Asp Lys Glu Met
                2355                2360                2365

Ala Glu Arg Cys Ala Thr Trp Leu Asn Met Glu Val Lys Ile Ile Asp
                2370                2375                2380

Ala Val Ile Gly Glu Arg Pro Pro Tyr Phe Cys Gly Gly Phe Ile Leu
2385                2390                2395                2400

Gln Asp Ser Val Thr Ser Thr Ala Cys Arg Val Ala Asp Pro Leu Lys
                2405                2410                2415

Arg Leu Phe Lys Leu Gly Lys Pro Leu Pro Ala Asp Asp Glu Gln Asp
                2420                2425                2430

Glu Asp Arg Arg Arg Ala Leu Leu Asp Glu Thr Lys Ala Trp Phe Arg
                2435                2440                2445

Val Gly Ile Thr Asp Thr Leu Ala Val Ala Val Ala Thr Arg Tyr Glu
                2450                2455                2460

Val Asp Asn Ile Thr Pro Val Leu Leu Ala Leu Arg Thr Phe Ala Gln
2465                2470                2475                2480

Ser Lys Arg Ala Phe Gln Ala Ile Arg Gly Glu Ile Lys His Leu Tyr
                2485                2490                2495

Gly Gly Pro Lys
            2500

(2) INFORMATION FOR SEQ ID NO:3:

(i) SEQUENCE CHARACTERISTICS:
        (A) LENGTH: 1245 amino acids
        (B) TYPE: amino acid
        (D) TOPOLOGY: linear (ii) MOLECULE TYPE: protein (xi) SEQUENCE DESCRIPTION: SEQ ID NO:3:

Met Asn Arg Gly Phe Phe Asn Met Leu Gly Arg Arg Pro Phe Pro Ala
1               5                   10                  15

Pro Thr Ala Met Trp Arg Pro Arg Arg Arg Gln Ala Ala Pro Met
            20                  25                  30

Pro Ala Arg Asn Gly Leu Ala Ser Gln Ile Gln Gln Leu Thr Thr Ala
        35                  40                  45

Val Ser Ala Leu Val Ile Gly Gln Ala Thr Arg Pro Gln Thr Pro Arg
    50                  55                  60

Pro Arg Pro Pro Pro Arg Gln Lys Lys Gln Ala Pro Lys Gln Pro Pro
65                  70                  75                  80
```

-continued

```
Lys Pro Lys Pro Lys Thr Gln Glu Lys Lys Lys Gln Pro Ala
                85                  90                  95

Lys Pro Lys Pro Gly Lys Arg Gln Arg Met Ala Leu Lys Leu Glu Ala
            100                 105                 110

Asp Arg Leu Phe Asp Val Lys Asn Glu Asp Gly Asp Val Ile Gly His
            115                 120                 125

Ala Leu Ala Met Glu Gly Lys Val Met Lys Pro Leu His Val Lys Gly
130                 135                 140

Thr Ile Asp His Pro Val Leu Ser Lys Leu Lys Phe Thr Lys Ser Ser
145                 150                 155                 160

Ala Tyr Asp Met Glu Phe Ala Gln Leu Pro Val Asn Met Arg Ser Glu
                165                 170                 175

Ala Phe Thr Tyr Thr Ser Glu His Pro Glu Gly Phe Tyr Asn Trp His
                180                 185                 190

His Gly Ala Val Gln Tyr Ser Gly Arg Phe Thr Ile Pro Arg Gly
                195                 200                 205

Val Gly Gly Arg Gly Asp Ser Gly Arg Pro Ile Met Asp Asn Ser Gly
210                 215                 220

Arg Val Val Ala Ile Val Leu Gly Gly Ala Asp Glu Gly Thr Arg Thr
225                 230                 235                 240

Ala Leu Ser Val Val Thr Trp Asn Ser Lys Gly Lys Thr Ile Lys Thr
                245                 250                 255

Thr Pro Glu Gly Thr Glu Glu Trp Ser Ala Ala Pro Leu Val Thr Ala
                260                 265                 270

Met Cys Leu Leu Gly Asn Val Ser Phe Pro Cys Asn Arg Pro Pro Thr
                275                 280                 285

Cys Tyr Thr Arg Glu Pro Ser Arg Ala Leu Asp Ile Leu Glu Glu Asn
                290                 295                 300

Val Asn His Glu Ala Tyr Asp Thr Leu Leu Asn Ala Ile Leu Arg Cys
305                 310                 315                 320

Gly Ser Ser Gly Arg Ser Lys Arg Ser Val Thr Asp Asp Phe Thr Leu
                325                 330                 335

Thr Ser Pro Tyr Leu Gly Thr Cys Ser Tyr Cys His His Thr Glu Pro
                340                 345                 350

Cys Phe Ser Pro Ile Lys Ile Glu Gln Val Trp Asp Glu Ala Asp Asp
            355                 360                 365

Asn Thr Ile Arg Ile Gln Thr Ser Ala Gln Phe Gly Tyr Asp Gln Ser
370                 375                 380

Gly Ala Ala Ser Ser Asn Lys Tyr Arg Tyr Met Ser Leu Glu Gln Asp
385                 390                 395                 400

His Thr Val Lys Glu Gly Thr Met Asp Asp Ile Lys Ile Ser Thr Ser
                405                 410                 415

Gly Pro Cys Arg Arg Leu Ser Tyr Lys Gly Tyr Phe Leu Leu Ala Lys
                420                 425                 430

Cys Pro Pro Gly Asp Ser Val Thr Val Ser Ile Ala Ser Ser Asn Ser
            435                 440                 445

Ala Thr Ser Cys Thr Met Ala Arg Lys Ile Lys Pro Lys Phe Val Gly
            450                 455                 460

Arg Glu Lys Tyr Asp Leu Pro Pro Val His Gly Lys Lys Ile Pro Cys
465                 470                 475                 480

Thr Val Tyr Asp Arg Leu Lys Glu Thr Thr Ala Gly Tyr Ile Thr Met
                485                 490                 495

His Arg Pro Gly Pro His Ala Tyr Thr Ser Tyr Leu Glu Glu Ser Ser
                500                 505                 510
```

-continued

Gly Lys Val Tyr Ala Lys Pro Pro Ser Gly Lys Asn Ile Thr Tyr Glu
        515                 520                 525

Cys Lys Cys Gly Asp Tyr Lys Thr Gly Thr Val Thr Thr Arg Thr Glu
        530                 535                 540

Ile Thr Gly Cys Thr Ala Ile Lys Gln Cys Val Ala Tyr Lys Ser Asp
545                 550                 555                 560

Gln Thr Lys Trp Val Phe Asn Ser Pro Asp Ser Ile Arg His Ala Asp
        565                 570                 575

His Thr Ala Gln Gly Lys Leu His Leu Pro Phe Lys Leu Ile Pro Ser
        580                 585                 590

Thr Cys Met Val Pro Val Ala His Ala Pro Asn Val Val His Gly Phe
        595                 600                 605

Lys His Ile Ser Leu Gln Leu Asp Thr Asp His Leu Thr Leu Leu Thr
        610                 615                 620

Thr Arg Arg Leu Gly Ala Asn Pro Glu Pro Thr Thr Glu Trp Ile Ile
625                 630                 635                 640

Gly Asn Thr Val Arg Asn Phe Thr Val Asp Arg Asp Gly Leu Glu Tyr
                    645                 650                 655

Ile Trp Gly Asn His Glu Pro Val Arg Val Tyr Ala Gln Glu Ser Ala
                    660                 665                 670

Pro Gly Asp Pro His Gly Trp Pro His Glu Ile Val Gln His Tyr Tyr
        675                 680                 685

His Arg His Pro Val Tyr Thr Ile Leu Ala Val Ala Ser Ala Ala Val
        690                 695                 700

Ala Met Met Ile Gly Val Thr Val Ala Ala Leu Cys Ala Cys Lys Ala
705                 710                 715                 720

Arg Arg Glu Cys Leu Thr Pro Tyr Ala Leu Ala Pro Asn Ala Val Ile
                    725                 730                 735

Pro Thr Ser Leu Ala Leu Leu Cys Cys Val Arg Ser Ala Asn Ala Glu
                    740                 745                 750

Thr Phe Thr Glu Thr Met Ser Tyr Leu Trp Ser Asn Ser Gln Pro Phe
        755                 760                 765

Phe Trp Val Gln Leu Cys Ile Pro Leu Ala Ala Val Val Val Leu Met
770                 775                 780

Arg Cys Cys Ser Cys Cys Leu Pro Phe Leu Val Val Ala Gly Ala Tyr
785                 790                 795                 800

Leu Ala Lys Val Asp Ala Tyr Glu His Ala Thr Thr Val Pro Asn Val
                    805                 810                 815

Pro Gln Ile Pro Tyr Lys Ala Leu Val Glu Arg Ala Gly Tyr Ala Pro
        820                 825                 830

Leu Asn Leu Glu Ile Thr Val Met Ser Ser Glu Val Leu Pro Ser Thr
        835                 840                 845

Asn Gln Glu Tyr Ile Thr Cys Lys Phe Thr Thr Val Val Pro Ser Pro
        850                 855                 860

Lys Val Arg Cys Cys Gly Ser Leu Glu Cys Gln Pro Ala Ala His Ala
865                 870                 875                 880

Asp Tyr Thr Cys Lys Val Phe Gly Gly Val Tyr Pro Phe Met Trp Gly
                    885                 890                 895

Gly Ala Gln Cys Phe Cys Asp Ser Glu Asn Ser Gln Met Ser Glu Ala
                    900                 905                 910

Tyr Val Glu Leu Ser Val Asp Cys Ala Thr Asp His Ala Gln Ala Ile
        915                 920                 925

Lys Val His Thr Ala Ala Met Lys Val Gly Leu Arg Ile Val Tyr Gly

-continued

```
          930             935             940
Asn Thr Thr Ser Phe Leu Asp Val Tyr Val Asn Gly Val Thr Pro Gly
945                 950                 955                 960

Thr Ser Lys Asp Leu Lys Val Ile Ala Gly Pro Ile Ser Ala Leu Phe
                965                 970                 975

Thr Pro Phe Asp His Lys Val Val Ile Asn Arg Gly Leu Val Tyr Asn
                980                 985                 990

Tyr Asp Phe Pro Glu Tyr Gly Ala Met Lys Pro Gly Ala Phe Gly Asp
            995                1000                1005

Ile Gln Ala Thr Ser Leu Thr Ser Lys Asp Leu Ile Ala Ser Thr Asp
           1010                1015                1020

Ile Arg Leu Leu Lys Pro Ser Ala Lys Asn Val His Val Pro Tyr Thr
1025               1030                1035                1040

Gln Ala Ala Ser Gly Phe Glu Met Trp Lys Asn Asn Ser Gly Arg Pro
                1045                1050                1055

Leu Gln Glu Thr Ala Pro Phe Gly Cys Lys Ile Ala Val Asn Pro Leu
               1060                 1065                1070

Arg Ala Val Asp Cys Ser Tyr Gly Asn Ile Pro Ile Ser Ile Asp Ile
           1075                1080                1085

Pro Asn Ala Ala Phe Ile Arg Thr Ser Asp Ala Pro Leu Val Ser Thr
1090               1095                1100

Val Lys Cys Asp Val Ser Glu Cys Thr Tyr Ser Ala Asp Phe Gly Gly
1105               1110                1115                1120

Met Ala Thr Leu Gln Tyr Val Ser Asp Arg Glu Gly Gln Cys Pro Val
                1125                1130                1135

His Ser His Ser Ser Thr Ala Ser Leu Gln Glu Ser Thr Val His Val
                1140                1145                1150

Leu Glu Lys Gly Ala Val Thr Val His Phe Ser Thr Ala Ser Pro Gln
                1155                1160                1165

Ala Asn Phe Ile Val Ser Leu Cys Gly Lys Lys Thr Thr Cys Asn Ala
           1170                1175                1180

Glu Cys Lys Pro Pro Ala Asp His Ile Val Ser Thr Pro His Lys Asn
1185               1190                1195                1200

Asp Gln Glu Phe Gln Ala Ala Ile Ser Lys Thr Ser Trp Ser Trp Leu
                1205                1210                1215

Phe Ala Leu Phe Gly Gly Ala Ser Ser Leu Leu Ile Ile Gly Leu Met
                1220                1225                1230

Ile Phe Ala Cys Ser Met Met Leu Thr Ser Thr Arg Arg
           1235                1240                1245

(2) INFORMATION FOR SEQ ID NO:4:

(i) SEQUENCE CHARACTERISTICS:
        (A) LENGTH: 11717 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

NTTGNCGGCG TAGTATACAC TATTGAATCA AACAGCCGAC CAATTGCACT ACCATCACA        59

ATG GAG AAG CCA GTA GTT AAC GTA GAC GTA GAC CCG CAG AGT CCG TTT       107

GTC GTG CAA CTG CAA AAG AGC TTC CCG CAA TTT GAG GTA GTA GCA CAG       155

CAG GTC ACT CCA AAT GAC CAT GCT AAT GCC AGA GCA TTT TCG CAT CTG       203
```

| | |
|---|---|
| GCC AGT AAA CTA ATC GAG CTG GAG GTT CCT ACC ACA GCG ACG ATT TTG | 251 |
| GAC ATA GGC AGC GCA CCG GCT CGT AGA ATG TTT TCC GAG CAC CAG TAC | 299 |
| CAT TGC GTT TGC CCC ATG CGT AGT CCA GAA GAC CCG GAC CGC ATG ATG | 347 |
| AAA TAT GCC AGC AAA CTG GCG GAA AAA GCA TGC AAG ATT ACG AAT AAG | 395 |
| AAC TTG CAT GAG AAG ATC AAG GAC CTC CGG ACC GTA CTT GAT ACA CCG | 443 |
| GAT GCT GAA ACG CCA TCA CTC TGC TTC CAC AAC GAT GTT ACC TGC AAC | 491 |
| ACG CGT GCC GAG TAC TCC GTC ATG CAG GAC GTG TAC ATC AAC GCT CCC | 539 |
| GGA ACT ATT TAC CAT CAG GCT ATG AAA GGC GTG CGG ACC CTG TAC TGG | 587 |
| ATT GGC TTC GAT ACC ACC CAG TTC ATG TTC TCG GCT ATG GCA GGT TCG | 635 |
| TAC CCT GCG TAC AAC ACC AAC TGG GCC GAC GAA AAA GTC CTC GAA GCG | 683 |
| CGT AAC ATC GGA CTC TGC AGC ACA AAG CTG AGT GAA GGC AGG ACA GGA | 731 |
| AAG TTG TCG ATA ATG AGG AAG AAG GAG TTG AAG CCC GGG TCA CGG GTT | 779 |
| TAT TTC TCC GTT GGA TCG ACA CTT TAC CCA GAA CAC AGA GCC AGC TTG | 827 |
| CAG AGC TGG CAT CTT CCA TCG GTG TTC CAC CTG AAA GGA AAG CAG TCG | 875 |
| TAC ACT TGC CGC TGT GAT ACA GTG GTG AGC TGC GAA GGC TAC GTA GTG | 923 |
| AAG AAA ATC ACC ATC AGT CCC GGG ATC ACG GGA GAA ACC GTG GGA TAC | 971 |
| GCG GTT ACA AAC AAT AGC GAG GGC TTC TTG CTA TGC AAA GTT ACC GAT | 1019 |
| ACA GTA AAA GGA GAA CGG GTA TCG TTC CCC GTG TGC ACG TAT ATC CCG | 1067 |
| GCC ACC ATA TGC GAT CAG ATG ACC GGC ATA ATG GCC ACG GAT ATC TCA | 1115 |
| CCT GAC GAT GCA CAA AAA CTT CTG GTT GGG CTC AAC CAG CGA ATC GTC | 1163 |
| ATT AAC GGT AAG ACT AAC AGG AAC ACC AAT ACC ATG CAA AAT TAC CTT | 1211 |
| CTG CCA ATC ATT GCA CAA GGG TTC AGC AAA TGG GCC AAG GAG CGC AAA | 1259 |
| GAA GAC CTT GAC AAT GAA AAA ATG CTG GGT ACC AGA GAG CGC AAG CTT | 1307 |
| ACA TAT GGC TGC TTG TGG GCG TTT CGC ACT AAG AAA GTG CAC TCG TTC | 1355 |
| TAT CGC CCA CCT GGA ACG CAG ACC ATC GTA AAA GTC CCA GCC TCT TTT | 1403 |
| AGC GCT TTC CCC ATG TCA TCC GTA TGG ACT ACC TCT TTG CCC ATG TCG | 1451 |
| CTG AGG CAG AAG ATA AAA TTG GCA TTA CAA CCA AAG AAG GAG GAA AAA | 1499 |
| CTG CTG CAA GTC CCG GAG GAA TTA GTC ATG GAG GCC AAG GCT GCT TTC | 1547 |
| GAG GAT GCT CAG GAG GAA TCC AGA GCG GAG AAG CTC CGA GAA GCA CTC | 1595 |
| CCA CCA TTA GTG GCA GAC AAA GGT ATC GAG GCA GCC GCG GAA GTT GTC | 1643 |
| TGC GAA GTG GAG GGG CTC CAG GCG GAC ATC GGA GCA GCA CTC GTC GAA | 1691 |
| ACC CCG CGC GGT CAT GTA AGG ATA ATA CCA CAA GCA AAT GAC CGT ATG | 1739 |
| ATC GGA CAG TAC ATC GTT GTC TCG CCA ACC TCT GTG CTG AAG AAC GCT | 1787 |
| AAA CTC GCA CCA GCA CAC CCG CTA GCA GAC CAG GTT AAG ATC ATA ACG | 1835 |
| CAC TCC GGA AGA TCA GGA AGG TAT GCA GTC GAA CCA TAC GAC GCT AAA | 1883 |
| GTA CTG ATG CCA GCA GGA AGT GCC GTA CCA TGG CCA GAA TTC TTA GCA | 1931 |
| CTG AGT GAG AGC GCC ACG CTA GTG TAC AAC GAA AGA GAG TTT GTG AAC | 1979 |
| CGC AAG CTG TAC CAT ATT GCC ATG CAC GGT CCC GCT AAG AAT ACA GAA | 2027 |
| GAG GAG CAG TAC AAG GTT ACA AAG GCA GAG CTC GCA GAA ACA GAG TAC | 2075 |
| GTG TTT GAC GTG GAC AAG AAG CGA TGC GTC AAG AAG GAA GAA GCC TCA | 2123 |

```
GGA CTT GTC CTC TCG GGA GAA CTG ACC AAC CCG CCC TAT CAC GAA CTA     2171

GCT CTT GAG GGA CTG AAG ACT CGA CCC GTG GTC CCG TAC AAG GTT GAA     2219

ACA ATA GGA GTG ATA GGC GCA CCA GGA TCG GGC AAG TCG GCT ATC ATC     2267

AAG TCA ACT GTC ACG GCA CGT GAT CTT GTT ACC AGC GGA AAG AAA GAA     2315

AAC TGC CGC GAA ATT CAG GCC GAT GTG CTA CGG CTG AGG GGC ATG CAG     2363

ATC ACG TCG AAG ACA GTG GAT TCG GTT ATG CTC AAC GGA TGC CGC AAA     2411

GCC GTA GAA GTG CTG TAT GTT GAC GAA GCG TTC GCG TGC CAC GCA GGA     2459

GCA CTA CTT GCC TTG ATT GCA ATC GTC AGA CCC CGT CAT AAG GTA GTG     2507

CTA TGC GGA GAC CCT AAG CAA TGC GGA TTC TTC AAC ATG ATG CAA CTA     2555

AAG GTA TAT TTC AAC CAC CCG GAA AAA GAC ATA TGT ACC AAG ACA TTC     2603

TAC AAG TTT ATC TCC CGA CGT TGC ACA CAG CCA GTC ACG GCT ATT GTA     2651

TCG ACA CTG CAT TAC GAT GGA AAA ATG AAA ACC ACA AAC CCG TGC AAG     2699

AAG AAC ATC GAA ATC GAC ATT ACA GGG GCC ACG AAG CCG AAG CCA GGG     2747

GAC ATC ATC CTG ACA TGC TTC CGC GGG TGG GTT AAG CAA CTG CAA ATC     2795

GAC TAT CCC GGA CAT GAG GTA ATG ACA GCC GCG GCC TCA CAA GGG CTA     2843

ACC AGA AAA GGA GTA TAT GCC GTC CGG CAA AAA GTC AAT GAA AAC CCG     2891

CTG TAC GCG ATC ACA TCA GAG CAT GTG AAC GTG CTG CTC ACC CGC ACT     2939

GAG GAC AGG CTA GTA TGG AAA ACT TTA CAG GGC GAC CCA TGG ATT AAG     2987

CAG CTC ACT AAC GTA CCA AAA GGA AAT TTT CAA GCC ACC ATC GAG GAC     3035

TGG GAA GCT GAA CAC AAG GGA ATA ATT GCT GCG ATA AAC AGT CCC GCT     3083

CCC CGT ACC AAT CCG TTC AGC TGC AAG ACT AAC GTT TGC TGG GCG AAA     3131

CGA CTG GAA CCG ATA CTG GCC ACG GCC GGT ATC GTA CTT ACC GGT TGC     3179

CAG TGG AGC GAG CTG TTC CCA CAG TTT GCA GAT GAC AAA CCA CAC TCG     3227

GCC ATC TAC GCC CTG GAC GTA ATC TGC ATT AAG TTT TTC GGC ATG GAC     3275

TTG ACA AGC GGA CTG TTT TCC AAA CAG AGC ATC CCG TTA ACG TAC CAT     3323

CCT GCC GAT TCA GCG AGG CCA GTA GCT CAT GGG ACA AAC AGC CCA GGA     3371

ACC CGC AAG TAT GGG TAC GAT CAC GCC GTT GCC GCC GAA CTC TCC CGT     3419

AGA TTT CCG GTG TTC AGC TAG CTG GGA AAA GGC ACA CAG CTT GAT TTG     3467

CAG ACG GGC AGA ACT AGA GTT ATC TCC GCA CAG CAT AAC TTG GTC CCA     3515

GTG AAC CGC AAT CTC CCG CAC GCC TTA GTC CCC GAG CAC AAG GAG AAA     3563

CAA CCC GGC CCG GTC AAA AAA TTC TTG AGC CAG TTC AAA CAC CAC TCC     3611

GTA CTT GTG GTC TCA GAG GAA AAA ATT GAA GCT CCC CAC AAG AGA ATC     3659

GAA TGG ATC GCC CCG ATT GGC ATA GCC GGC GCT GAT AAG AAC TAC AAC     3707

CTG GCT TTC GGG TTT CCG CCG CAG GCA CGG TAC GAC CTG GTG TTT ATC     3755

AAT ATT GGA ACT AAA TAC AGA AAC CAT CAC TTT CAG CAG TGC GAA GAC     3803

CAT GCG GCG ACC TTG AAA ACC CTC TCG CGT TCG GCC CTG AAC TGC CTT     3851

AAC CCC GGA GGC ACC CTC GTG GTG AAG TCC TAC GGT TAC GCC GAC CGC     3899

AAT AGT GAG GAC GTA GTC ACC GCT CTT GCC AGA AAA TTT GTC AGA GTG     3947

TCT GCA GCG AGG CCA GAG TGC GTC TCA AGC AAT ACA GAA ATG TAC CTG     3995

ATC TTC CGA CAA CTA GAC AAC AGC CGC ACA CGA CAA TTC ACC CCG CAT     4043
```

```
CAT CTG AAT TGT GTG ATT TCG TCC GTG TAC GAG GGT ACA AGA GAC GGA      4091

GTT GGA GCC GCA CCG TCA TAC CGC ACT AAA AGG GAG AAC ATT GCT GAT      4139

TGT CAA GAG GAA GCA GTT GTC AAT GCA GCC AAT CCG CTG GGC AGA CCA      4187

GGC GAA GGA GTC TGC CGT GCC ATC TAT AAA CGT TGG CCG AAC AGT TTC      4235

ACC GAT TCA GCC ACA GAG ACC GGC ACC GCA AAA CTG ACT GTG TGC CAA      4283

GGA AAG AAA GTG ATC CAC GCG GTT GGC CCT GAT TTC CGG AAA CAC CCA      4331

GAG GCA GAA GCC CTG AAA TTG CTG CAA AAC GCC TAC CAT GCA GTG GCA      4379

GAC TTA GTA AAT GAA CAT AAT ATC AAG TCT GTC GCC ATC CCA CTG CTA      4427

TCT ACA GGC ATT TAC GCA GCC GGA AAA GAC CGC CTT GAA GTA TCA CTT      4475

AAC TGC TTG ACA ACC GCG CTA GAT AGA ACT GAT GCG GAC GTA ACC ATC      4523

TAC TGC CTG GAT AAG AAG TGG AAG GAA AGA ATC GAC GCG GTG CTC CAA      4571

CTT AAG GAG TCT GTA ATA GAG CTG AAG GAT GAG GAT ATG GAG ATC GAC      4619

GAC GAG TTA GTA TGG ATC CAT CCG GAC AGT TGC CTG AAG GGA AGA AAG      4667

GGA TTC AGT ACT ACA AAA GGA AAG TTG TAT TCG TAC TTT GAA GGC ACC      4715

AAA TTC CAT CAA GCA GCA AAA GAT ATG GCG GAG ATA AAG GTC CTG TTC      4763

CCA AAT GAC CAG GAA AGC AAC GAG CAA CTG TGT GCC TAC ATA TTG GGG      4811

GAG ACC ATG GAA GCA ATC CGC GAA AAA TGC CCG GTC GAC CAC AAC CCG      4859

TCG TCT AGC CCG CCA AAA ACG CTG CCG TGC CTC TGC ATG TAT GCC ATG      4907

ACG CCA GAA AGG GTC CAC AGA CTC AGA AGC AAC AAC GTC AAA GAA GTT      4955

ACA GTA TGC TCC TCC ACC CCC CTT CCA AAG TAC AAA ATC AAG AAC GTT      5003

CAG AAG GTT CAG TGC ACA AAA GTA GTC CTG TTT AAC CCG CAT ACC CCT      5051

GCA TTC GTT CCC GCC CGT AAG TAC ATA GAA GCG CCA GAA CAG CCT GCA      5099

GCT CCG CCT GCA CAG GCC GAG GAG GCC CCC GAA GTT GCA GCA ACA CCA      5147

ACA CCA CCT GCA GCT GAT AAC ACC TCG CTT GAT GTC ACG GAC ATC TCA      5195

CTG GAC ATG GAA GAC AGT AGC GAA GGC TCA CTC TTT TCG AGC TTT AGC      5243

GGA TCG GAC AAC TCT ATT ACT AGT ATG GAC AGT TGG TCG TCA GGA CCT      5291

AGT TCA CTA GAG ATA GTA GAC CGA AGG CAG GTG GTG GTG GCT GAC GTC      5339

CAT GCC GTC CAA GAG CCT GCC CCT GTT CCA CCG CCA AGG CTA AAG AAG      5387

ATG GCC CGC CTG GCA GCG GCA AGA ATG CAG GAA GAG CCA ACT CCA CCG      5435

GCA AGC ACC AGC TCT GCG GAC GAG TCC CTT CAC CTT TCT TTT GGT GGG      5483

GTA TCC ATG TCC TTC GGA TCC CTT TTC GAC GGA GAG ATG GGC GCC TTG      5531

GCA GCG GCA CAA CCC CCG GCA AGT ACA TGC CCT ACG GAT GTG CCT ATG      5579

TCT TTC GGA TCG TTT TCC GAC GGA GAG ATT GAG GAG CTG AGC CGC AGA      5627

GTA ACC GAG TCT GAG CCC GTC CTG TTT GGG TCA TTT GAA CCG GGC GAA      5675

GTG AAC TCA ATT ATA TCG TCC CGA TCA GTT GTA TCT TTT CCA CCA CGC      5723

AAG CAG AGA CGT AGA CGC AGG AGC AGG AGG ACC GAA TAC TGA CTA ACC      5771

GGG GTA GGT GGG TAC ATA TTT TCG ACG GAC ACA GGC CCT GGG CAC TTG      5819

CAA ATG GAG TCC GTT CTG CAG AAT CAG CTT ACA GAA CCG ACC TTG GAG      5867

CGC AAT GTT CTG GAA AGA ATC TAC GCC CCG GTG CTC GAC ACG TCG AAA      5915

GAG GAA CAG CTC AAA CTC AGG TAC CAG ATG ATG CCC ACC GAA GCC AAC      5963
```

```
AAA AGC AGG TAC CAG TCT AGA AAA GTA GAA AAT CAG AAA GCC ATA ACC      6011

ACT GAG CGA CTG CTT TCA GGG CTA CGA CTG TAT AAC TCT GCC ACA GAT      6059

CAG CCA GAA TGC TAT AAG ATC ACC TAC CCG AAA CCA TCG TAT TCC AGC      6107

AGT GTA CCG GCG AAC TAC TCT GAC CCA AAG TTT GCT GTA GCT GTT TGC      6155

AAC AAC TAT CTG CAT GAG AAT TAC CCG ACG GTA GCA TCT TAT CAG ATC      6203

ACC GAC GAG TAC GAT GCT TAC TTG GAT ATG GTA GAC GGG ACA GTC GCT      6251

TGC CTA GAT ACT GCA ACT TTT TGC CCC GCC AAG CTT AGA AGT TAC CCG      6299

AAA AGA CAC GAG TAT AGA GCC CCA AAC ACT CGC AGT GCG GTT CCA TCA      6347

GCG ATG CAG AAC ACG TTG CAA AAC GTG CTC ATT GCC GCG ACT AAA AGA      6395

AAC TGC AAC GTC ACA CAA ATG CGT GAA TTG CCA ACA CTG GAC TCA GCG      6443

ACA TTC AAC GTT GAA TGC TTT CGA AAA TAT GCA TGT AAT GAC GAG TAT      6491

TGG GAG GAG TTT GCC CGA AAG CCA ATT AGG ATC ACT ACT GAG TTC GTT      6539

ACC GCA TAC GTG GCC AGA CTG AAA GGC CCT AAG GCC GCC GCA CTG TTC      6587

GCA AAG ACG CAT AAT TTG GTC CCA TTG CAA GAA GTG CCT ATG GAT AGG      6635

TTC GTC ATG GAC ATG AAA AGA GAC GTG AAA GTT ACA CCT GGC ACG AAA      6683

CAC ACA GAA GAA AGA CCG AAA GTA CAA GTG CTA CAA GCC GCA GAA CCC      6731

CTG GCG ACC GCT TAC CTG TGC GGG ATC CAC CGG GAG TTA GTG CGC AGG      6779

CTT ACA GCC GTC TTG CTA CCC AAC ATT CAC ACG CTT TTT GAC ATG TCG      6827

GCG GAG GAC TTT GAT GCA ATC ATA GCA GAA CAC TTC AAG CAA GGT GAC      6875

CCG GTA CTG GAG ACG GAT ATC GCC TCG TTC GAC AAA AGC CAA GAC GAC      6923

GCT ATG GCG TTA ACT GGC CTG ATG ATC TTG GAA GAC CTG GGT GTG GAC      6971

CAA CCA CTA CTC GAC TTG ATC GAG TGC GCC TTT GGA GAA ATA TCA TCC      7019

ACC CAT CTG CCC ACG GGT ACC CGT TTC AAA TTC GGG GCG ATG ATG AAA      7067

TCC GGA ATG TTC CTC ACG CTC TTT GTC AAC ACA GTT CTG AAT GTC GTT      7115

ATC GCC AGC AGA GTA TTG GAG GAG CGG CTT AAA ACG TCC AAA TGT GCA      7163

GCA TTT ATC GGC GAC GAC AAC ATC ATA CAC GGA GTA GTA TCT GAC AAA      7211

GAA ATG GCT GAG AGG TGT GCC ACC TGG CTC AAC ATG GAG GTT AAG ATC      7259

ATT GAC GCA GTC ATC GGC GAG AGA CCG CCT TAC TTC TGC GGT GGA TTC      7307

ATC TTG CAA GAT TCG GTT ACC TCC ACA GCG TGT CGC GTG GCG GAC CCC      7355

TTG AAA AGG CTG TTT AAG TTG GGT AAA CCG CTC CCA GCC GAC GAC GAG      7403

CAA GAC GAA GAC AGA AGA CGC GCT CTG CTA GAT GAA ACA AAG GCG TGG      7451

TTT AGA GTA GGT ATA ACA GAC ACC TTA GCA GTG GCC GTG GCA ACT CGG      7499

TAT GAG GTA GAC AAC ATC ACA CCT GTC CTG CTG GCA TTG AGA ACT TTT      7547

GCC CAG AGC AAA AGA GCA TTT CAA GCC ATC AGA GGG GAA ATA AAG CAT      7595

CTC TAC GGT GGT CCT AAA TAGTCAGCAT AGCACATTTC ATCTGACTAA            7643

TACCACAACA CCACCACC ATG AAT AGA GGA TTC TTT AAC ATG CTC GGC CGC      7694

CGC CCC TTC CCG GCC CCC ACT GCC ATG TGG AGG CCG CGG AGA AGG AGG      7742

CAG GCG GCC CCG ATG CCT GCC CGC AAT GGG CTG GCT TCC CAA ATC CAG      7790

CAA CTG ACC ACA GCC GTC AGT GCC CTA GTC ATT GGA CAG GCA ACT AGA      7838

CCT CAA ACC CCA CGC CCA CGC CCG CCG CCG CGC CAG AAG AAG CAG GCG      7886
```

| | |
|---|---:|
| CCA AAG CAA CCA CCG AAG CCG AAG AAA CCA AAA ACA CAG GAG AAG AAG | 7934 |
| AAG AAG CAA CCT GCA AAA CCC AAA CCC GGA AAG AGA CAA CGT ATG GCA | 7982 |
| CTC AAG TTG GAG GCC GAC AGA CTG TTC GAC GTC AAA AAT GAG GAC GGA | 8030 |
| GAT GTC ATC GGG CAC GCA CTG GCC ATG GAA GGA AAG GTA ATG AAA CCA | 8078 |
| CTC CAC GTG AAA GGA ACT ATT GAC CAC CCT GTG CTA TCA AAG CTC AAA | 8126 |
| TTC ACC AAG TCG TCA GCA TAC GAC ATG GAG TTC GCA CAG TTG CCG GTC | 8174 |
| AAC ATG AGA AGT GAG GCG TTC ACC TAC ACC AGC GAA CAC CCT GAA GGG | 8222 |
| TTT TAC AAC TGG CAC CAC GGA GCG GTG CAG TAT AGT GGA GGT AGA TTT | 8270 |
| ACC ATC CCC CGC GGA GTA GGA GGC AGA GGA GAC AGT GGT CGT CCG ATT | 8318 |
| ATG GAT AAC TCA GGC CGG GTT GTC GCG ATA GTC CTC GGA GGG GCT GAT | 8366 |
| GAG GGA ACA AGA ACT GCC CTT TCG GTC GTC ACC TGG AAT AGC AAA GGG | 8414 |
| AAG ACA ATC AAG ACA ACC CCG GAA GGG ACA GAA GAG TGG TCT GCA GCA | 8462 |
| CCA CTG GTC ACG GCC ATG TGC TTG CTT GGA AAC GTG AGC TTC CCA TGC | 8510 |
| AAT CGC CCG CCC ACA TGC TAC ACC CGC GAA CCA TCC AGA GCT CTT GAC | 8558 |
| ATC CTT GAA GAG AAC GTG AAC CAC GAG GCC TAC GAC ACC CTG CTC AAC | 8606 |
| GCC ATA TTG CGG TGC GGA TCG TCC GGC AGA AGC AAA AGA AGC GTC ACT | 8654 |
| GAC GAC TTT ACC TTG ACC AGC CCG TAC TTG GGC ACA TGC TCG TAC TGT | 8702 |
| CAC CAT ACT GAA CCG TGC TTT AGC CCG ATT AAG ATC GAG CAG GTC TGG | 8750 |
| GAT GAA GCG GAC GAC AAC ACC ATA CGC ATA CAG ACT TCC GCC CAG TTT | 8798 |
| GGA TAC GAC CAA AGC GGA GCA GCA AGC TCA AAT AAG TAC CGC TAC ATG | 8846 |
| TCG CTC GAG CAG GAT CAT ACC GTC AAA GAA GGC ACT ATG GAT GAC ATC | 8894 |
| AAG ATC AGC ACC TCA GGA CCG TGT AGA AGG CTT AGC TAC AAA GGA TAC | 8942 |
| TTT CTC CTC GCG AAG TGT CCT CCA GGG GAC AGC GTA ACG GTT AGT ATA | 8990 |
| GCG AGT AGC AAC TCA GCA ACG TCA TGC ACA ATG GCC CGC AAG ATA AAA | 9038 |
| CCA AAA TTC GTG GGA CGG GAA AAA TAT GAC CTA CCT CCC GTT CAC GGT | 9086 |
| AAG AAG ATT CCT TGC ACA GTG TAC GAC CGT CTG AAA GAA ACA ACC GCC | 9134 |
| GGC TAC ATC ACT ATG CAC AGG CCG GGA CCG CAC GCC TAT ACG TCC TAT | 9182 |
| CTG GAG GAA TCA TCA GGG AAA GTC TAC GCG AAG CCA CCA TCC GGA AAG | 9230 |
| AAC ATT ACG TAC GAG TGC AAG TGC GGC GAT TAC AAG ACC GGT ACC GTT | 9278 |
| ACG ACC CGT ACC GAA ATC ACG GGC TGC ACC GCC ATC AAG CAG TGC GTC | 9326 |
| GCC TAT AAG AGC GAC CAA ACG AAG TGG GTC TTC AAT TCG CCG GAC TTG | 9374 |
| ATC AGA CAT GCC GAC CAC ACG GCC CAA GGG AAA TTG CAT TTA CCT TTC | 9422 |
| AAG CTG ATC CCG AGT ACC TGC ATG GTC CCT GTT GCC CAC GCG CCG AAC | 9470 |
| GTA GTA CAC GGC TTT AAA CAC ATC AGC CTC CAA TTA GAC ACA GAC CAC | 9518 |
| CTG ACA TTG CTC ACC ACC AGG AGA CTA GGG GCA AAT CCG GAA CCA ACT | 9566 |
| ACT GAA TGG ATC ATC GGA AAG ACG GTT AGA AAC TTC ACC GTC GAC CGA | 9614 |
| GAT GGC CTG GAA TAC ATA TGG GGC AAT CAC GAA CCG GTA AGG GTC TAT | 9662 |
| GCC CAA GAG TCT GCA CCA GGA GAC CCT CAC GGA TGG CCA CAC GAA ATA | 9710 |
| GTA CAG CAT TAC TAC CAT CGC CAT CCT GTG TAC ACC ATC TTA GCC GTC | 9758 |
| GCA TCA GCT GCT GTG GCG ATG ATG ATT GGC GTA ACT GTT GCA GCA TTA | 9806 |

| | |
|---|---|
| TGT GCC TGT AAA GCG CGC CGT GAG TGC CTG ACG CCA TAT GCC CTG GCC | 9854 |
| CCA AAT GCC GTG ATT CCA ACT TCG CTG GCA CTT TTG TGC TGT GTT AGG | 9902 |
| TCG GCT AAT GCT GAA ACA TTC ACC GAG ACC ATG AGT TAC CTA TGG TCG | 9950 |
| AAC AGC CAG CCA TTC TTC TGG GTC CAG CTG TGT ATA CCC CTG GCC GCT | 9998 |
| GTC ATC GTT CTA ATG CGC TGT TGC TCA TGC TGC CTG CCT TTT TTA GTG | 10046 |
| GTT GCC GGC GCC TAC CTG GCG AAG GTA GAC GCC TAC GAA CAT GCG ACC | 10094 |
| ACT GTT CCA AAT GTG CCA CAG ATA CCG TAT AAG GCA CTT GTT GAA AGG | 10142 |
| GCA GGG TAC GCC CCG CTC AAT TTG GAG ATT ACT GTC ATG TCC TCG GAG | 10190 |
| GTT TTG CCT TCC ACC AAC CAA GAG TAC ATC ACC TGC AAA TTC ACC ACT | 10238 |
| GTG GTC CCC TCC CCT AAA GTC AAA TGC TGC GGC TCC TTG GAA TGT CAG | 10286 |
| CCC GCC GCT CAC GCA GAC TAT ACC TGC AAG GTC TTT GGA GGG GTG TAC | 10334 |
| CCC TTC ATG TGG GGA GGA GCA CAA TGT TTT TGC GAC AGT GAG AAC AGC | 10382 |
| CAG ATG AGT GAG GCG TAC GTC GAA TTG TCA GCA GAT TGC GCG ACT GAC | 10430 |
| CAC GCG CAG GCG ATT AAG GTG CAT ACT GCC GCG ATG AAA GTA GGA CTA | 10478 |
| CGT ATA GTG TAC GGG AAC ACT ACC AGT TTC CTA GAT GTG TAC GTG AAC | 10526 |
| GGA GTC ACA CCA GGA ACG TCT AAA GAC CTG AAA GTC ATA GCT GGA CCA | 10574 |
| ATT TCA GCA TCG TTT ACA CCA TTC GAT CAC AAG GTC GTT ATC CAT CGC | 10622 |
| GGC CTG GTG TAC AAC TAT GAC TTC CCG GAA TAC GGA GCG ATG AAA CCA | 10670 |
| GGA GCG TTT GGA GAC ATT CAA GCT ACC TCC TTG ACT AGC AAA GAT CTC | 10718 |
| ATC GCC AGC ACA GAC ATT AGA CTA CTC AAG CCT TCC GCC AAG AAC GTG | 10766 |
| CAT GTC CCG TAC ACG CAG GCC GCA TCT GGA TTC GAG ATG TGG AAA AAC | 10814 |
| AAC TCA GGC CGC CCA CTG CAG GAA ACC GCC CCT TTC GGG TGC AAG ATT | 10862 |
| GCA GTC AAT CCG CTT CGA GCG GTG GAC TGC TCA TAC GGG AAC ATT CCC | 10910 |
| ATC TCT ATC GAC ATC CCG AAC GCT GCC TTT ATC AGG ACA TCA GAT GCA | 10958 |
| CCA CTG GTC TCA ACA GTC AAA TGT GAT GTC AGT GAG TGC ACT TAC TCA | 11006 |
| GCG GAC TTC GGC GGG ATG GCT ACC CTG CAG TAT GTA TCC GAC CGC GAA | 11054 |
| GGA CAA TGC CCT GTA CAT TCG CAT TCG AGC ACA GCA ACC CTC CAA GAG | 11102 |
| TCG ACA GTT CAT GTC CTG GAG AAA GGA GCG GTG ACA GTA CAC TTC AGC | 11150 |
| ACC GCG AGC CCA CAG GCG AAC TTT ATT GTA TCG CTG TGT GGT AAG AAG | 11198 |
| ACA ACA TGC AAT GCA GAA TGC AAA CCA CCA GCT GAC CAT ATC GTG AGC | 11246 |
| ACC CCG CAC AAA AAT GAC CAA GAA TTC CAA GCC GCC ATC TCA AAA ACT | 11294 |
| TCA TGG AGT TGG CTG TTT GCC CTT TTC GGC GGC GCC TCG TCG CTA TTA | 11342 |
| ATT ATA GGA CTT ATG ATT TTT GCT TGC AGC ATG ATG CTG ACT AGC ACA | 11390 |
| CGA AGA TGACCGCTAC GCCCCAATGA CCCGACCAGC AAAACTCGAT GTACTTCCGA | 11446 |
| GGAACTGATG TGCATAATGC ATCAGGCTGG TATATTAGAT CCCCGCTTAC CGCGGGCAAT | 11506 |
| ATAGCAACAC CAAAACTCGA CGTATTTCCG AGGAAGCGCA GTGCATAATG CTGCGCAGTG | 11566 |
| TTGCCAAATA ATCACTATAT TAACCATTTA TTTAGCGGAC GCCAAAACTC AATGTATTTC | 11626 |
| TGAGGAAGCA TGGTGCATAA TGCCATGCAG CGTCTGCATA ACTTTTTATT ATTTCTTTTA | 11686 |
| TTAATCAACA AAATTTTGTT TTTAACATTT N | 11717 |

(2) INFORMATION FOR SEQ ID NO:5:

(i) SEQUENCE CHARACTERISTICS:
    (A) LENGTH: 2517 amino acids
    (B) TYPE: amino acid
    (D) TOPOLOGY: linear (ii) MOLECULE TYPE: protein (xi) SEQUENCE DESCRIPTION: SEQ ID NO:5:

```
Met Glu Lys Pro Val Val Asn Val Asp Val Asp Pro Gln Ser Pro Phe
 1               5                  10                  15

Val Val Gln Leu Gln Lys Ser Phe Pro Gln Phe Glu Val Val Ala Gln
                20                  25                  30

Gln Val Thr Pro Asn Asp His Ala Asn Ala Arg Ala Phe Ser His Leu
            35                  40                  45

Ala Ser Lys Leu Ile Glu Leu Glu Val Pro Thr Thr Ala Thr Ile Leu
        50                  55                  60

Asp Ile Gly Ser Ala Pro Ala Arg Arg Met Phe Ser Glu His Gln Tyr
 65                  70                  75                  80

His Cys Val Cys Pro Met Arg Ser Pro Glu Asp Pro Asp Arg Met Met
                85                  90                  95

Lys Tyr Ala Ser Lys Leu Ala Glu Lys Ala Cys Lys Ile Thr Asn Lys
            100                 105                 110

Asn Leu His Glu Lys Ile Lys Asp Leu Arg Thr Val Leu Asp Thr Pro
        115                 120                 125

Asp Ala Glu Thr Pro Ser Leu Cys Phe His Asn Asp Val Thr Cys Asn
    130                 135                 140

Thr Arg Ala Glu Tyr Ser Val Met Gln Asp Val Tyr Ile Asn Ala Pro
145                 150                 155                 160

Gly Thr Ile Tyr His Gln Ala Met Lys Gly Val Arg Thr Leu Tyr Trp
                165                 170                 175

Ile Gly Phe Asp Thr Thr Gln Phe Met Phe Ser Ala Met Ala Gly Ser
            180                 185                 190

Tyr Pro Ala Tyr Asn Thr Asn Trp Ala Asp Glu Lys Val Leu Glu Ala
        195                 200                 205

Arg Asn Ile Gly Leu Cys Ser Thr Lys Leu Ser Glu Gly Arg Thr Gly
    210                 215                 220

Lys Leu Ser Ile Met Arg Lys Lys Glu Leu Lys Pro Gly Ser Arg Val
225                 230                 235                 240

Tyr Phe Ser Val Gly Ser Thr Leu Tyr Pro Glu His Arg Ala Ser Leu
                245                 250                 255

Gln Ser Trp His Leu Pro Ser Val Phe His Leu Lys Gly Lys Gln Ser
        260                 265                 270

Tyr Thr Cys Arg Cys Asp Thr Val Val Ser Cys Glu Gly Tyr Val Val
    275                 280                 285

Lys Lys Ile Thr Ile Ser Pro Gly Ile Thr Gly Glu Thr Val Gly Tyr
290                 295                 300

Ala Val Thr Asn Asn Ser Glu Gly Phe Leu Leu Cys Lys Val Thr Asp
305                 310                 315                 320

Thr Val Lys Gly Glu Arg Val Ser Phe Pro Val Cys Thr Tyr Ile Pro
                325                 330                 335

Ala Thr Ile Cys Asp Gln Met Thr Gly Ile Met Ala Thr Asp Ile Ser
            340                 345                 350

Pro Asp Asp Ala Gln Lys Leu Leu Val Gly Leu Asn Gln Arg Ile Val
        355                 360                 365

Ile Asn Gly Lys Thr Asn Arg Asn Thr Asn Thr Met Gln Asn Tyr Leu
```

-continued

```
            370                 375                 380
Leu Pro Ile Ile Ala Gln Gly Phe Ser Lys Trp Ala Lys Glu Arg Lys
385                 390                 395                 400

Glu Asp Leu Asp Asn Glu Lys Met Leu Gly Thr Arg Glu Arg Lys Leu
                405                 410                 415

Thr Tyr Gly Cys Leu Trp Ala Phe Arg Thr Lys Lys Val His Ser Phe
            420                 425                 430

Tyr Arg Pro Pro Gly Thr Gln Thr Ile Val Lys Val Pro Ala Ser Phe
            435                 440                 445

Ser Ala Phe Pro Met Ser Ser Val Trp Thr Thr Ser Leu Pro Met Ser
            450                 455                 460

Leu Arg Gln Lys Ile Lys Leu Ala Leu Gln Pro Lys Lys Glu Glu Lys
465                 470                 475                 480

Leu Leu Gln Val Pro Glu Glu Leu Val Met Glu Ala Lys Ala Ala Phe
                485                 490                 495

Glu Asp Ala Gln Glu Glu Ser Arg Ala Glu Lys Leu Arg Glu Ala Leu
                500                 505                 510

Pro Pro Leu Val Ala Asp Lys Gly Ile Glu Ala Ala Glu Val Val
                515                 520                 525

Cys Glu Val Glu Gly Leu Gln Ala Asp Ile Gly Ala Ala Leu Val Glu
530                 535                 540

Thr Pro Arg Gly His Val Arg Ile Ile Pro Gln Ala Asn Asp Arg Met
545                 550                 555                 560

Ile Gly Gln Tyr Ile Val Val Ser Pro Thr Ser Val Leu Lys Asn Ala
                565                 570                 575

Lys Leu Ala Pro Ala His Pro Leu Ala Asp Gln Val Lys Ile Ile Thr
                580                 585                 590

His Ser Gly Arg Ser Gly Arg Tyr Ala Val Glu Pro Tyr Asp Ala Lys
    595                 600                 605

Val Leu Met Pro Ala Gly Ser Ala Val Pro Trp Pro Glu Phe Leu Ala
    610                 615                 620

Leu Ser Glu Ser Ala Thr Leu Val Tyr Asn Glu Arg Glu Phe Val Asn
625                 630                 635                 640

Arg Lys Leu Tyr His Ile Ala Met His Gly Pro Ala Lys Asn Thr Glu
                645                 650                 655

Glu Glu Gln Tyr Lys Val Thr Lys Ala Glu Leu Ala Glu Thr Glu Tyr
                660                 665                 670

Val Phe Asp Val Asp Lys Lys Arg Cys Val Lys Lys Glu Ala Ser
                675                 680                 685

Gly Leu Val Leu Ser Gly Glu Leu Thr Asn Pro Tyr His Glu Leu
    690                 695                 700

Ala Leu Glu Gly Leu Lys Thr Arg Pro Val Val Pro Tyr Lys Val Glu
705                 710                 715                 720

Thr Ile Gly Val Ile Gly Ala Pro Gly Ser Gly Lys Ser Ala Ile Ile
                725                 730                 735

Lys Ser Thr Val Thr Ala Arg Asp Leu Val Thr Ser Gly Lys Lys Glu
            740                 745                 750

Asn Cys Arg Glu Ile Gln Ala Asp Val Leu Arg Leu Arg Gly Met Gln
            755                 760                 765

Ile Thr Ser Lys Thr Val Asp Ser Val Met Leu Asn Gly Cys Arg Lys
            770                 775                 780

Ala Val Glu Val Leu Tyr Val Asp Glu Ala Phe Ala Cys His Ala Gly
785                 790                 795                 800
```

-continued

Ala Leu Leu Ala Leu Ile Ala Ile Val Arg Pro Arg His Lys Val Val
             805                 810                 815

Leu Cys Gly Asp Pro Lys Gln Cys Gly Phe Phe Asn Met Met Gln Leu
             820                 825                 830

Lys Val Tyr Phe Asn His Pro Glu Lys Asp Ile Cys Thr Lys Thr Phe
             835                 840                 845

Tyr Lys Phe Ile Ser Arg Arg Cys Thr Gln Pro Val Thr Ala Ile Val
             850                 855                 860

Ser Thr Leu His Tyr Asp Gly Lys Met Lys Thr Thr Asn Pro Cys Lys
865                 870                 875                 880

Lys Asn Ile Glu Ile Asp Ile Thr Gly Ala Thr Lys Pro Lys Pro Gly
             885                 890                 895

Asp Ile Ile Leu Thr Cys Phe Arg Gly Trp Val Lys Gln Leu Gln Ile
             900                 905                 910

Asp Tyr Pro Gly His Glu Val Met Thr Ala Ala Ser Gln Gly Leu
             915                 920                 925

Thr Arg Lys Gly Val Tyr Ala Val Arg Gln Lys Val Asn Glu Asn Pro
930                 935                 940

Leu Tyr Ala Ile Thr Ser Glu His Val Asn Val Leu Leu Thr Arg Thr
945                 950                 955                 960

Glu Asp Arg Leu Val Trp Lys Thr Leu Gln Gly Asp Pro Trp Ile Lys
             965                 970                 975

Gln Leu Thr Asn Val Pro Lys Gly Asn Phe Gln Ala Thr Ile Glu Asp
             980                 985                 990

Trp Glu Ala Glu His Lys Gly Ile Ile Ala Ala Ile Asn Ser Pro Ala
             995                 1000                1005

Pro Arg Thr Asn Pro Phe Ser Cys Lys Thr Asn Val Cys Trp Ala Lys
             1010                1015                1020

Arg Leu Glu Pro Ile Leu Ala Thr Ala Gly Ile Val Leu Thr Gly Cys
1025                1030                1035                1040

Gln Trp Ser Glu Leu Phe Pro Gln Phe Ala Asp Asp Lys Pro His Ser
             1045                1050                1055

Ala Ile Tyr Ala Leu Asp Val Ile Cys Ile Lys Phe Phe Gly Met Asp
             1060                1065                1070

Leu Thr Ser Gly Leu Phe Ser Lys Gln Ser Ile Pro Leu Thr Tyr His
             1075                1080                1085

Pro Ala Asp Ser Ala Arg Pro Val Ala His Trp Asp Asn Ser Pro Gly
             1090                1095                1100

Thr Arg Lys Tyr Gly Tyr Asp His Ala Val Ala Ala Glu Leu Ser Arg
1105                1110                1115                1120

Arg Phe Pro Val Phe Gln Leu Ala Gly Lys Gly Thr Gln Leu Asp Leu
             1125                1130                1135

Gln Thr Gly Arg Thr Arg Val Ile Ser Ala Gln His Asn Leu Val Pro
             1140                1145                1150

Val Asn Arg Asn Leu Pro His Ala Leu Val Pro Glu His Lys Glu Lys
             1155                1160                1165

Gln Pro Gly Pro Val Lys Lys Phe Leu Ser Gln Phe Lys His His Ser
             1170                1175                1180

Val Leu Val Val Ser Glu Glu Lys Ile Glu Ala Pro His Lys Arg Ile
1185                1190                1195                1200

Glu Trp Ile Ala Pro Ile Gly Ile Ala Gly Ala Asp Lys Asn Tyr Asn
             1205                1210                1215

Leu Ala Phe Gly Phe Pro Pro Gln Ala Arg Tyr Asp Leu Val Phe Ile
             1220                1225                1230

```
Asn Ile Gly Thr Lys Tyr Arg Asn His His Phe Gln Gln Cys Glu Asp
        1235                1240                1245

His Ala Ala Thr Leu Lys Thr Leu Ser Arg Ser Ala Leu Asn Cys Leu
    1250                1255                1260

Asn Pro Gly Gly Thr Leu Val Val Lys Ser Tyr Gly Tyr Ala Asp Arg
1265                1270                1275                1280

Asn Ser Glu Asp Val Val Thr Ala Leu Ala Arg Lys Phe Val Arg Val
            1285                1290                1295

Ser Ala Ala Arg Pro Glu Cys Val Ser Ser Asn Thr Glu Met Tyr Leu
            1300                1305                1310

Ile Phe Arg Gln Leu Asp Asn Ser Arg Thr Gln Phe Thr Pro His
        1315                1320                1325

His Leu Asn Cys Val Ile Ser Ser Val Tyr Glu Gly Thr Arg Asp Gly
        1330                1335                1340

Val Gly Ala Ala Pro Ser Tyr Arg Thr Lys Arg Glu Asn Ile Ala Asp
1345                1350                1355                1360

Cys Gln Glu Glu Ala Val Val Asn Ala Ala Asn Pro Leu Gly Arg Pro
            1365                1370                1375

Gly Glu Gly Val Cys Arg Ala Ile Tyr Lys Arg Trp Pro Asn Ser Phe
        1380                1385                1390

Thr Asp Ser Ala Thr Glu Thr Gly Thr Ala Lys Leu Thr Val Cys Gln
        1395                1400                1405

Gly Lys Lys Val Ile His Ala Val Gly Pro Asp Phe Arg Lys His Pro
    1410                1415                1420

Glu Ala Glu Ala Leu Lys Leu Leu Gln Asn Ala Tyr His Ala Val Ala
1425                1430                1435                1440

Asp Leu Val Asn Glu His Asn Ile Lys Ser Val Ala Ile Pro Leu Leu
            1445                1450                1455

Ser Thr Gly Ile Tyr Ala Ala Gly Lys Asp Arg Leu Glu Val Ser Leu
        1460                1465                1470

Asn Cys Leu Thr Thr Ala Leu Asp Arg Thr Asp Ala Asp Val Thr Ile
        1475                1480                1485

Tyr Cys Leu Asp Lys Lys Trp Lys Glu Arg Ile Asp Ala Val Leu Gln
        1490                1495                1500

Leu Lys Glu Ser Val Ile Glu Leu Lys Asp Glu Asp Met Glu Ile Asp
1505                1510                1515                1520

Asp Glu Leu Val Trp Ile His Pro Asp Ser Cys Leu Lys Gly Arg Lys
            1525                1530                1535

Gly Phe Ser Thr Thr Lys Gly Lys Leu Tyr Ser Tyr Phe Glu Gly Thr
        1540                1545                1550

Lys Phe His Gln Ala Ala Lys Asp Met Ala Glu Ile Lys Val Leu Phe
        1555                1560                1565

Pro Asn Asp Gln Glu Ser Asn Glu Gln Leu Cys Ala Tyr Ile Leu Gly
    1570                1575                1580

Glu Thr Met Glu Ala Ile Arg Glu Lys Cys Pro Val Asp His Asn Pro
1585                1590                1595                1600

Ser Ser Ser Pro Pro Lys Thr Leu Pro Cys Leu Cys Met Tyr Ala Met
            1605                1610                1615

Thr Pro Glu Arg Val His Arg Leu Arg Ser Asn Asn Val Lys Glu Val
        1620                1625                1630

Thr Val Cys Ser Ser Thr Pro Leu Pro Lys Tyr Lys Ile Lys Asn Val
        1635                1640                1645

Gln Lys Val Gln Cys Thr Lys Val Val Leu Phe Asn Pro His Thr Pro
```

```
                1650                1655                1660
Ala Phe Val Pro Ala Arg Lys Tyr Ile Glu Ala Pro Glu Gln Pro Ala
1665                1670                1675                1680

Ala Pro Pro Ala Gln Ala Glu Glu Ala Pro Glu Val Ala Ala Thr Pro
                1685                1690                1695

Thr Pro Pro Ala Ala Asp Asn Thr Ser Leu Asp Val Thr Asp Ile Ser
            1700                1705                1710

Leu Asp Met Glu Asp Ser Ser Glu Gly Ser Leu Phe Ser Ser Phe Ser
            1715                1720                1725

Gly Ser Asp Asn Ser Ile Thr Ser Met Asp Ser Trp Ser Ser Gly Pro
            1730                1735                1740

Ser Ser Leu Glu Ile Val Asp Arg Arg Gln Val Val Val Ala Asp Val
1745                1750                1755                1760

His Ala Val Gln Glu Pro Ala Pro Val Pro Pro Arg Leu Lys Lys
                1765                1770                1775

Met Ala Arg Leu Ala Ala Ala Arg Met Gln Glu Pro Thr Pro Pro
            1780                1785                1790

Ala Ser Thr Ser Ser Ala Asp Glu Ser Leu His Leu Ser Phe Gly Gly
            1795                1800                1805

Val Ser Met Ser Phe Gly Ser Leu Phe Asp Gly Glu Met Gly Ala Leu
            1810                1815                1820

Ala Ala Ala Gln Pro Pro Ala Ser Thr Cys Pro Thr Asp Val Pro Met
1825                1830                1835                1840

Ser Phe Gly Ser Phe Ser Asp Gly Glu Ile Glu Leu Ser Arg Arg
            1845                1850                1855

Val Thr Glu Ser Glu Pro Val Leu Phe Gly Ser Phe Glu Pro Gly Glu
            1860                1865                1870

Val Asn Ser Ile Ile Ser Ser Arg Ser Val Val Ser Phe Pro Pro Arg
            1875                1880                1885

Lys Gln Arg Arg Arg Arg Ser Arg Arg Thr Glu Tyr Leu Thr Gly
            1890                1895                1900

Val Gly Gly Tyr Ile Phe Ser Thr Asp Thr Gly Pro Gly His Leu Gln
1905                1910                1915                1920

Met Glu Ser Val Leu Gln Asn Gln Leu Thr Glu Pro Thr Leu Glu Arg
            1925                1930                1935

Asn Val Leu Glu Arg Ile Tyr Ala Pro Val Leu Asp Thr Ser Lys Glu
            1940                1945                1950

Glu Gln Leu Lys Leu Arg Tyr Gln Met Met Pro Thr Glu Ala Asn Lys
            1955                1960                1965

Ser Arg Tyr Gln Ser Arg Lys Val Glu Asn Gln Lys Ala Ile Thr Thr
            1970                1975                1980

Glu Arg Leu Leu Ser Gly Leu Arg Leu Tyr Asn Ser Ala Thr Asp Gln
1985                1990                1995                2000

Pro Glu Cys Tyr Lys Ile Thr Tyr Pro Lys Pro Ser Tyr Ser Ser Ser
                2005                2010                2015

Val Pro Ala Asn Tyr Ser Asp Pro Lys Phe Ala Val Ala Val Cys Asn
            2020                2025                2030

Asn Tyr Leu His Glu Asn Tyr Pro Thr Val Ala Ser Tyr Gln Ile Thr
            2035                2040                2045

Asp Glu Tyr Asp Ala Tyr Leu Asp Met Val Asp Gly Thr Val Ala Cys
            2050                2055                2060

Leu Asp Thr Ala Thr Phe Cys Pro Ala Lys Leu Arg Ser Tyr Pro Lys
2065                2070                2075                2080
```

-continued

```
Arg His Glu Tyr Arg Ala Pro Asn Thr Arg Ser Ala Val Pro Ser Ala
            2085                2090                2095

Met Gln Asn Thr Leu Gln Asn Val Leu Ile Ala Ala Thr Lys Arg Asn
            2100                2105                2110

Cys Asn Val Thr Gln Met Arg Glu Leu Pro Thr Leu Asp Ser Ala Thr
            2115                2120                2125

Phe Asn Val Glu Cys Phe Arg Lys Tyr Ala Cys Asn Asp Glu Tyr Trp
            2130                2135                2140

Glu Glu Phe Ala Arg Lys Pro Ile Arg Ile Thr Thr Glu Phe Val Thr
2145                2150                2155                2160

Ala Tyr Val Ala Arg Leu Lys Gly Pro Lys Ala Ala Ala Leu Phe Ala
            2165                2170                2175

Lys Thr His Asn Leu Val Pro Leu Gln Glu Val Pro Met Asp Arg Phe
            2180                2185                2190

Val Met Asp Met Lys Arg Asp Val Lys Val Thr Pro Gly Thr Lys His
            2195                2200                2205

Thr Glu Glu Arg Pro Lys Val Gln Val Leu Gln Ala Ala Glu Pro Leu
            2210                2215                2220

Ala Thr Ala Tyr Leu Cys Gly Ile His Arg Glu Leu Val Arg Arg Leu
2225                2230                2235                2240

Thr Ala Val Leu Leu Pro Asn Ile His Thr Leu Phe Asp Met Ser Ala
            2245                2250                2255

Glu Asp Phe Asp Ala Ile Ile Ala Glu His Phe Lys Gln Gly Asp Pro
            2260                2265                2270

Val Leu Glu Thr Asp Ile Ala Ser Phe Asp Lys Ser Gln Asp Asp Ala
            2275                2280                2285

Met Ala Leu Thr Gly Leu Met Ile Leu Glu Asp Leu Gly Val Asp Gln
            2290                2295                2300

Pro Leu Leu Asp Leu Ile Glu Cys Ala Phe Gly Glu Ile Ser Ser Thr
2305                2310                2315                2320

His Leu Pro Thr Gly Thr Arg Phe Lys Phe Gly Ala Met Met Lys Ser
            2325                2330                2335

Gly Met Phe Leu Thr Leu Phe Val Asn Thr Val Leu Asn Val Val Ile
            2340                2345                2350

Ala Ser Arg Val Leu Glu Glu Arg Leu Lys Thr Ser Lys Cys Ala Ala
            2355                2360                2365

Phe Ile Gly Asp Asp Asn Ile Ile His Gly Val Val Ser Asp Lys Glu
            2370                2375                2380

Met Ala Glu Arg Cys Ala Thr Trp Leu Asn Met Glu Val Lys Ile Ile
2385                2390                2395                2400

Asp Ala Val Ile Gly Glu Arg Pro Pro Tyr Phe Cys Gly Gly Phe Ile
            2405                2410                2415

Leu Gln Asp Ser Val Thr Ser Thr Ala Cys Arg Val Ala Asp Pro Leu
            2420                2425                2430

Lys Arg Leu Phe Lys Leu Gly Lys Pro Leu Pro Ala Asp Asp Glu Gln
            2435                2440                2445

Asp Glu Asp Arg Arg Arg Ala Leu Leu Asp Glu Thr Lys Ala Trp Phe
            2450                2455                2460

Arg Val Gly Ile Thr Asp Thr Leu Ala Val Ala Val Ala Thr Arg Tyr
2465                2470                2475                2480

Glu Val Asp Asn Ile Thr Pro Val Leu Leu Ala Leu Arg Thr Phe Ala
            2485                2490                2495

Gln Ser Lys Arg Ala Phe Gln Ala Ile Arg Gly Glu Ile Lys His Leu
            2500                2505                2510
```

```
Tyr Gly Gly Pro Lys
        2515

(2) INFORMATION FOR SEQ ID NO:6:

(i) SEQUENCE CHARACTERISTICS:
        (A) LENGTH: 1245 amino acids
        (B) TYPE: amino acid
        (D) TOPOLOGY: linear (ii) MOLECULE TYPE: protein (xi) SEQUENCE DESCRIPTION: SEQ ID NO:6:

Met Asn Arg Gly Phe Phe Asn Met Leu Gly Arg Arg Pro Phe Pro Ala
 1               5                  10                  15

Pro Thr Ala Met Trp Arg Pro Arg Arg Arg Gln Ala Ala Pro Met
            20                  25                  30

Pro Ala Arg Asn Gly Leu Ala Ser Gln Ile Gln Gln Leu Thr Thr Ala
            35                  40                  45

Val Ser Ala Leu Val Ile Gly Gln Ala Thr Arg Pro Gln Thr Pro Arg
        50                  55                  60

Pro Arg Pro Pro Arg Gln Lys Lys Gln Ala Pro Lys Gln Pro Pro
65                  70                  75                  80

Lys Pro Lys Lys Pro Lys Thr Gln Glu Lys Lys Lys Gln Pro Ala
                    85                  90                  95

Lys Pro Lys Pro Gly Lys Arg Gln Arg Met Ala Leu Lys Leu Glu Ala
                    100                 105                 110

Asp Arg Leu Phe Asp Val Lys Asn Glu Asp Gly Asp Val Ile Gly His
            115                 120                 125

Ala Leu Ala Met Glu Gly Lys Val Met Lys Pro Leu His Val Lys Gly
        130                 135                 140

Thr Ile Asp His Pro Val Leu Ser Lys Leu Lys Phe Thr Lys Ser Ser
145                 150                 155                 160

Ala Tyr Asp Met Glu Phe Ala Gln Leu Pro Val Asn Met Arg Ser Glu
                165                 170                 175

Ala Phe Thr Tyr Thr Ser Glu His Pro Glu Gly Phe Tyr Asn Trp His
            180                 185                 190

His Gly Ala Val Gln Tyr Ser Gly Arg Phe Thr Ile Pro Arg Gly
        195                 200                 205

Val Gly Gly Arg Gly Asp Ser Gly Arg Pro Ile Met Asp Asn Ser Gly
    210                 215                 220

Arg Val Val Ala Ile Val Leu Gly Gly Ala Asp Glu Gly Thr Arg Thr
225                 230                 235                 240

Ala Leu Ser Val Val Thr Trp Asn Ser Lys Gly Lys Thr Ile Lys Thr
                245                 250                 255

Thr Pro Glu Gly Thr Glu Glu Trp Ser Ala Ala Pro Leu Val Thr Ala
            260                 265                 270

Met Cys Leu Leu Gly Asn Val Ser Phe Pro Cys Asn Arg Pro Pro Thr
        275                 280                 285

Cys Tyr Thr Arg Glu Pro Ser Arg Ala Leu Asp Ile Leu Glu Glu Asn
    290                 295                 300

Val Asn His Glu Ala Tyr Asp Thr Leu Leu Asn Ala Ile Leu Arg Cys
305                 310                 315                 320

Gly Ser Ser Gly Arg Ser Lys Arg Ser Val Thr Asp Asp Phe Thr Leu
                325                 330                 335

Thr Ser Pro Tyr Leu Gly Thr Cys Ser Tyr Cys His His Thr Glu Pro
```

-continued

```
             340                 345                 350
Cys Phe Ser Pro Ile Lys Ile Glu Gln Val Trp Asp Glu Ala Asp Asp
            355                 360                 365
Asn Thr Ile Arg Ile Gln Thr Ser Ala Gln Phe Gly Tyr Asp Gln Ser
370                 375                 380
Gly Ala Ala Ser Ser Asn Lys Tyr Arg Tyr Met Ser Leu Glu Gln Asp
385                 390                 395                 400
His Thr Val Lys Glu Gly Thr Met Asp Asp Ile Lys Ile Ser Thr Ser
                405                 410                 415
Gly Pro Cys Arg Arg Leu Ser Tyr Lys Gly Tyr Phe Leu Leu Ala Lys
                420                 425                 430
Cys Pro Pro Gly Asp Ser Val Thr Val Ser Ile Ala Ser Ser Asn Ser
            435                 440                 445
Ala Thr Ser Cys Thr Met Ala Arg Lys Ile Lys Pro Lys Phe Val Gly
        450                 455                 460
Arg Glu Lys Tyr Asp Leu Pro Pro Val His Gly Lys Lys Ile Pro Cys
465                 470                 475                 480
Thr Val Tyr Asp Arg Leu Lys Glu Thr Thr Ala Gly Tyr Ile Thr Met
                485                 490                 495
His Arg Pro Gly Pro His Ala Tyr Thr Ser Tyr Leu Glu Glu Ser Ser
                500                 505                 510
Gly Lys Val Tyr Ala Lys Pro Ser Gly Lys Asn Ile Thr Tyr Glu
            515                 520                 525
Cys Lys Cys Gly Asp Tyr Lys Thr Gly Thr Val Thr Thr Arg Thr Glu
            530                 535                 540
Ile Thr Gly Cys Thr Ala Ile Lys Gln Cys Val Ala Tyr Lys Ser Asp
545                 550                 555                 560
Gln Thr Lys Trp Val Phe Asn Ser Pro Asp Leu Ile Arg His Ala Asp
                565                 570                 575
His Thr Ala Gln Gly Lys Leu His Leu Pro Phe Lys Leu Ile Pro Ser
                580                 585                 590
Thr Cys Met Val Pro Val Ala His Ala Pro Asn Val Val His Gly Phe
        595                 600                 605
Lys His Ile Ser Leu Gln Leu Asp Thr Asp His Leu Thr Leu Leu Thr
    610                 615                 620
Thr Arg Arg Leu Gly Ala Asn Pro Glu Pro Thr Thr Glu Trp Ile Ile
625                 630                 635                 640
Gly Lys Thr Val Arg Asn Phe Thr Val Asp Arg Asp Gly Leu Glu Tyr
                645                 650                 655
Ile Trp Gly Asn His Glu Pro Val Arg Val Tyr Ala Gln Glu Ser Ala
                660                 665                 670
Pro Gly Asp Pro His Gly Trp Pro His Glu Ile Val Gln His Tyr Tyr
            675                 680                 685
His Arg His Pro Val Tyr Thr Ile Leu Ala Val Ala Ser Ala Ala Val
    690                 695                 700
Ala Met Met Ile Gly Val Thr Val Ala Ala Leu Cys Ala Cys Lys Ala
705                 710                 715                 720
Arg Arg Glu Cys Leu Thr Pro Tyr Ala Leu Ala Pro Asn Ala Val Ile
                725                 730                 735
Pro Thr Ser Leu Ala Leu Leu Cys Cys Val Arg Ser Ala Asn Ala Glu
                740                 745                 750
Thr Phe Thr Glu Thr Met Ser Tyr Leu Trp Ser Asn Ser Gln Pro Phe
            755                 760                 765
```

-continued

```
Phe Trp Val Gln Leu Cys Ile Pro Leu Ala Ala Val Ile Val Leu Met
    770             775                 780

Arg Cys Cys Ser Cys Cys Leu Pro Phe Leu Val Val Ala Gly Ala Tyr
785             790                 795                 800

Leu Ala Lys Val Asp Ala Tyr Glu His Ala Thr Thr Val Pro Asn Val
                805                 810                 815

Pro Gln Ile Pro Tyr Lys Ala Leu Val Glu Arg Ala Gly Tyr Ala Pro
            820                 825                 830

Leu Asn Leu Glu Ile Thr Val Met Ser Ser Glu Val Leu Pro Ser Thr
            835                 840                 845

Asn Gln Glu Tyr Ile Thr Cys Lys Phe Thr Thr Val Val Pro Ser Pro
850                 855                 860

Lys Val Lys Cys Cys Gly Ser Leu Glu Cys Gln Pro Ala Ala His Ala
865                 870                 875                 880

Asp Tyr Thr Cys Lys Val Phe Gly Gly Val Tyr Pro Phe Met Trp Gly
                885                 890                 895

Gly Ala Gln Cys Phe Cys Asp Ser Glu Asn Ser Gln Met Ser Glu Ala
                900                 905                 910

Tyr Val Glu Leu Ser Ala Asp Cys Ala Thr Asp His Ala Gln Ala Ile
            915                 920                 925

Lys Val His Thr Ala Ala Met Lys Val Gly Leu Arg Ile Val Tyr Gly
            930                 935                 940

Asn Thr Thr Ser Phe Leu Asp Val Tyr Val Asn Gly Val Thr Pro Gly
945                 950                 955                 960

Thr Ser Lys Asp Leu Lys Val Ile Ala Gly Pro Ile Ser Ala Ser Phe
                965                 970                 975

Thr Pro Phe Asp His Lys Val Val Ile His Arg Gly Leu Val Tyr Asn
                980                 985                 990

Tyr Asp Phe Pro Glu Tyr Gly Ala Met Lys Pro Gly Ala Phe Gly Asp
            995                 1000                1005

Ile Gln Ala Thr Ser Leu Thr Ser Lys Asp Leu Ile Ala Ser Thr Asp
        1010                1015                1020

Ile Arg Leu Leu Lys Pro Ser Ala Lys Asn Val His Val Pro Tyr Thr
1025                1030                1035                1040

Gln Ala Ala Ser Gly Phe Glu Met Trp Lys Asn Asn Ser Gly Arg Pro
                1045                1050                1055

Leu Gln Glu Thr Ala Pro Phe Gly Cys Lys Ile Ala Val Asn Pro Leu
            1060                1065                1070

Arg Ala Val Asp Cys Ser Tyr Gly Asn Ile Pro Ile Ser Ile Asp Ile
        1075                1080                1085

Pro Asn Ala Ala Phe Ile Arg Thr Ser Asp Ala Pro Leu Val Ser Thr
    1090                1095                1100

Val Lys Cys Asp Val Ser Glu Cys Thr Tyr Ser Ala Asp Phe Gly Gly
1105                1110                1115                1120

Met Ala Thr Leu Gln Tyr Val Ser Asp Arg Glu Gly Gln Cys Pro Val
                1125                1130                1135

His Ser His Ser Ser Thr Ala Thr Leu Gln Glu Ser Thr Val His Val
                1140                1145                1150

Leu Glu Lys Gly Ala Val Thr Val His Phe Ser Thr Ala Ser Pro Gln
            1155                1160                1165

Ala Asn Phe Ile Val Ser Leu Cys Gly Lys Lys Thr Thr Cys Asn Ala
            1170                1175                1180

Glu Cys Lys Pro Pro Ala Asp His Ile Val Ser Thr Pro His Lys Asn
1185                1190                1195                1200
```

```
Asp Gln Glu Phe Gln Ala Ala Ile Ser Lys Thr Ser Trp Ser Trp Leu
            1205                1210                1215

Phe Ala Leu Phe Gly Gly Ala Ser Ser Leu Leu Ile Ile Gly Leu Met
            1220                1225                1230

Ile Phe Ala Cys Ser Met Met Leu Thr Ser Thr Arg Arg
            1235                1240            1245

(2) INFORMATION FOR SEQ ID NO:7:

(i) SEQUENCE CHARACTERISTICS:
        (A) LENGTH: 11663 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:
```

| | | | | | |
|---|---|---|---|---|---|
| ATTGGCGGCG | TAGTACACAC | TATTGAATCA | AACAGCCGAC | CAATTGCACT | ACCATCACAA | 60 |
| TGGAGAAGCC | AGTAGTTAAC | GTAGACGTAG | ACCCTCAGAG | TCCGTTTGTC | GTGCAACTGC | 120 |
| AAAAGAGCTT | CCCGCAATTT | GAGGTAGTAG | CACAGCAGGT | CACTCCAAAT | GACCATGCTA | 180 |
| ATGCCAGAGC | ATTTTCGCAT | CTGGCCAGTA | AACTGATCGA | GCTGGAGGTT | CCTACCACAG | 240 |
| CGACGATTTT | GGACATAGGC | AGCGCACCGG | CTCGTAGAAT | GTTTTCCGAG | CACCAGTACC | 300 |
| ATTGCGTTTG | CCCCATGCGT | AGTCCAGAAG | ACCCGGACCG | CATGATGAAA | TATGCCAGCA | 360 |
| AACTGGCGGA | AAAAGCATGT | AAGATTACAA | ACAAGAACTT | GCATGAGAAG | ATCAAGGACC | 420 |
| TCCGGACCGT | ACTTGATACA | CCGGATGCTG | AAACGCCATC | ACTCTGCTTC | ACAACGATG | 480 |
| TTACCTGCAA | CACGCGTGCC | GAGTACTCCG | TCATGCAGGA | CGTGTACATC | AACGCTCCCG | 540 |
| GAACTATTTA | CCACCAGGCT | ATGAAAGGCG | TGCGGACCCT | GTACTGGATT | GGCTTCGACA | 600 |
| CCACCCAGTT | CATGTTCTCG | GCTATGGCAG | GTTCGTACCC | TGCATACAAC | ACCAACTGGG | 660 |
| CCGACGAAAA | AGTCCTTGAA | GCGCGTAACA | TCGGACTCTG | CAGCACAAAG | CTGAGTGAAG | 720 |
| GCAGGACAGG | AAAGTTGTCG | ATAATGAGGA | AGAAGGAGTT | GAAGCCCGGG | TCACGGGTTT | 780 |
| ATTTCTCCGT | TGGATCGACA | CTTTACCCAG | AACACAGAGC | CAGCTTGCAG | AGCTGGCATC | 840 |
| TTCCATCGGT | GTTCCACTTG | AAAGGAAAGC | AGTCGTACAC | TTGCCGCTGT | GATACAGTGG | 900 |
| TGAGCTGCGA | AGGCTACGTA | GTGAAGAAAA | TCACCATCAG | TCCCGGGATC | ACGGGAGAAA | 960 |
| CCGTGGGATA | CGCGGTTACA | AACAATAGCG | AGGGCTTCTT | GCTATGCAAA | GTTACCGATA | 1020 |
| CAGTAAAAGG | AGAACGGGTA | TCGTTCCCCG | TGTGCACGTA | TATCCCGGCC | ACCATATGCG | 1080 |
| ATCAGATGAC | CGGCATAATG | GCCACGGATA | TCTCACCTGA | CGATGCACAA | AAACTTCTGG | 1140 |
| TTGGGCTCAA | CCAGCGAATC | GTCATTAACG | GTAAGACTAA | CAGGAACACC | AATACCATGC | 1200 |
| AAAATTACCT | TCTGCCAATC | ATTGCACAAG | GGTTCAGCAA | ATGGGCCAAG | GAGCGCAAAG | 1260 |
| AAGATCTTGA | CAATGAAAAA | ATGCTGGGCA | CCAGAGAGCG | CAAGCTTACA | TATGGCTGCT | 1320 |
| TGTGGGCGTT | TCGCACTAAG | AAAGTGCACT | CGTTCTATCG | CCCACCTGGA | ACGCAGACCA | 1380 |
| TCGTAAAAGT | CCCAGCCTCT | TTTAGCGCTT | TCCCCATGTC | ATCCGTATGG | ACTACCTCTT | 1440 |
| TGCCCATGTC | GCTGAGGCAG | AAGATGAAAT | TGGCATTACA | ACCAAAGAAG | GAGGAAAAAC | 1500 |
| TGCTGCAAGT | CCCGGAGGAA | TTAGTTATGG | AGGCCAAGGC | TGCTTTCGAG | GATGCTCAGG | 1560 |
| AGGAATCCAG | AGCGGAGAAG | CTCCGAGAAG | CACTCCCACC | ATTAGTGGCA | GACAAAGGTA | 1620 |
| TCGAGGCAGC | TGCGGAAGTT | GTCTGCGAAG | TGGAGGGGCT | CCAGGCGGAC | ACCGGAGCAG | 1680 |
| CACTCGTCGA | AACCCCGCGC | GGTCATGTAA | GGATAATACC | TCAAGCAAAT | GACCGTATGA | 1740 |

-continued

```
TCGGACAGTA TATCGTTGTC TCGCCGATCT CTGTGCTGAA GAACGCTAAA CTCGCACCAG    1800

CACACCCGCT AGCAGACCAG GTTAAGATCA TAACGCACTC CGGAAGATCA GGAAGGTATG    1860

CAGTCGAACC ATACGACGCT AAAGTACTGA TGCCAGCAGG AAGTGCCGTA CCATGGCCAG    1920

AATTCTTAGC ACTGAGTGAG AGCGCCACGC TTGTGTACAA CGAAAGAGAG TTTGTGAACC    1980

GCAAGCTGTA CCATATTGCC ATGCACGGTC CCGCTAAGAA TACAGAAGAG GAGCAGTACA    2040

AGGTTACAAA GGCAGAGCTC GCAGAAACAG AGTACGTGTT TGACGTGGAC AAGAAGCGAT    2100

GCGTTAAGAA GGAAGAAGCC TCAGGACTTG TCCTTTCGGG AGAACTGACC AACCCGCCCT    2160

ATCACGAACT AGCTCTTGAG GGACTGAAGA CTCGACCCGC GGTCCCGTAC AAGGTTGAAA    2220

CAATAGGAGT GATAGGCACA CCAGGATCGG GCAAGTCAGC TATCATCAAG TCAACTGTCA    2280

CGGCACGTGA TCTTGTTACC AGCGGAAAGA AGAAAACTG CCGCGAAATT GAGGCCGACG     2340

TGCTACGGCT GAGGGGCATG CAGATCACGT CGAAGACAGT GGATTCGGTT ATGCTCAACG    2400

GATGCCACAA AGCCGTAGAA GTGCTGTATG TTGACGAAGC GTTCCGGTGC CACGCAGGAG    2460

CACTACTTGC CTTGATTGCA ATCGTCAGAC CCCGTAAGAA GGTAGTACTA TGCGGAGACC    2520

CTAAGCAATG CGGATTCTTC AACATGATGC AACTAAAGGT ACATTTCAAC CACCCTGAAA    2580

AAGACATATG TACCAAGACA TTCTACAAGT TTATCTCCCG ACGTTGCACA CAGCCAGTCA    2640

CGGCTATTGT ATCGACACTG CATTACGATG GAAAAATGAA AACCACAAAC CCGTGCAAGA    2700

AGAACATCGA AATCGACATT ACAGGGGCCA CGAAGCCGAA GCCAGGGGAC ATCATCCTGA    2760

CATGTTTCCG CGGGTGGGTT AAGCAACTGC AAATCGACTA TCCCGGACAT GAGGTAATGA    2820

CAGCCGCGGC CTCACAAGGG CTAACCAGAA AAGGAGTATA TGCCGTCCGG CAAAAAGTCA    2880

ATGAAAACCC GCTGTACGCG ATCACATCAG AGCATGTGAA CGTGTTGCTC ACCCGCACTG    2940

AGGACAGGCT AGTATGGAAA ACTTTACAGG GCGACCCATG GATTAAGCAG CTCACTAACG    3000

TACCTAAAGG AAATTTTCAG GCCACCATCG AGGACTGGGA AGCTGAACAC AAGGGAATAA    3060

TTGCTGCGAT AAACAGTCCC GCTCCCCGTA CCAATCCGTT CAGCTGCAAG ACTAACGTTT    3120

GCTGGGCGAA AGCACTGGAA CCGATACTGG CCACGGCCGG TATCGTACTT ACCGGTTGCC    3180

AGTGGAGCGA GCTGTTCCCA CAGTTTGCGG ATGACAAACC ACACTCGGCC ATCTACGCCT    3240

TAGACGTAAT TTGCATTAAG TTTTTCGGCA TGGACTTGAC AAGCGGGCTG TTTTCCAAAC    3300

AGAGCATCCC GTTAACGTAC CATCCTGCCG ACTCAGCGAG GCCAGTAGCT CATTGGGACA    3360

ACAGCCCAGG AACACGCAAG TATGGGTACG ATCACGCCGT TGCCGCCGAA CTCTCCCGTA    3420

GATTTCCGGT GTTCCAGCTA GCTGGGAAAG GCACACAGCT TGATTTGCAG ACGGGCAGAA    3480

CTAGAGTTAT CTCTGCACAG CATAACTTGG TCCCAGTGAA CCGCAATCTC CCTCACGCCT    3540

TAGTCCCCGA GCACAAGGAG AAACAACCCG GCCCGGTCGA AAAATTCTTG AGCCAGTTCA    3600

AACACCACTC CGTACTTGTG ATCTCAGAGA AAAAAATTGA AGCTCCCCAC AAGAGAATCG    3660

AATGGATCGC CCCGATTGGC ATAGCCGGCG CAGATAAGAA CTACAACCTG GCTTTCGGGT    3720

TTCCGCCGCA GGCACGGTAC GACCTGGTGT TCATCAATAT TGGAACTAAA TACAGAAACC    3780

ATCACTTTCA ACAGTGCGAA GACCACGCGG CGACCTTGAA AACCCTTTCG CGTTCGGCCC    3840

TGAACTGCCT TAACCCCGGA GGGACCCTCG TGGTGAAGTC CTACGGTTAC GCCGACCGCA    3900

ATAGTGAGGA CGTAGTCACC GCTCTTGCCA GAAAATTTGT CAGAGTGTCT GCAGCGAGGC    3960

CAGAGTGCGT CTCAAGCAAT ACAGAAATGT ACCTGATTTT CCGACAACTA GACAACAGCC    4020

GCACACGACA ATTCACCCCG CATCATTTGA ATTGTGTGAT TCGTCCGTG TACGAGGGTA     4080

CAAGAGACGG AGTTGGAGCC GCACCGTCGT ACCGTACTAA AAGGGAGAAC ATTGCTGATT    4140
```

-continued

```
GTCAAGAGGA AGCAGTTGTC AATGCAGCCA ATCCACTGGG CAGACCAGGA GAAGGAGTCT    4200
GCCGTGCCAT CTATAAACGT TGGCCGAACA GTTTCACCGA TTCAGCCACA GAGACAGGTA    4260
CCGCAAAACT GACTGTGTGC CAAGGAAAGA AAGTGATCCA CGCGGTTGGC CCTGATTTCC    4320
GGAAACACCC AGAGGCAGAA GCCCTGAAAT TGCTGCAAAA CGCCTACCAT GCAGTGGCAG    4380
ACTTAGTAAA TGAACATAAT ATCAAGTCTG TCGCCATCCC ACTGCTATCT ACAGGCATTT    4440
ACGCAGCCGG AAAAGACCGC CTTGAGGTAT CACTTAACTG CTTGACAACC GCGCTAGACA    4500
GAACTGATGC GGACGTAACC ATCTACTGCC TGGATAAGAA GTGGAAGGAA AGAATCGACG    4560
CGGTGCTCCA ACTTAAGGAG TCTGTAACTG AGCTGAAGGA TGAGGATATG GAGATCGACG    4620
ACGAGTTAGT ATGGATCCAT CCGGACAGTT GCCTGAAGGG AAGAAAGGGA TTCAGTACTA    4680
CAAAAGGAAA GTTGTATTCG TACTTTGAAG GCACCAAATT CCATCAAGCA GCAAAAGATA    4740
TGGCGGAGAT AAAGGTCCTG TTCCCAAATG ACCAGGAAAG CAACGAACAA CTGTGTGCCT    4800
ACATATTGGG GGAGACCATG GAAGCAATCC GCGAAAAATG CCCGGTCGAC CACAACCCGT    4860
CGTCTAGCCC GCCAAAAACG CTGCCGTGCC TCTGTATGTA TGCCATGACG CCAGAAAGGG    4920
TCCACAGACT CAGAAGCAAT AACGTCAAAG AAGTTACAGT ATGCTCCTCC ACCCCCCTTC    4980
CAAAGTACAA AATCAAGAAT GTTCAGAAGG TTCAGTGCAC AAAAGTAGTC CTGTTTAACC    5040
CGCATACCCC CGCATTCGTT CCCGCCCGTA AGTACATAGA AGCACCAGAA CAGCCTGCAG    5100
CTCCGCCTGC ACAGGCCGAG GAGGCCCCCG GAGTTGTAGC GACACCAACA CCACCTGCAG    5160
CTGATAACAC CTCGCTTGAT GTCACGGACA TCTCACTGGA CATGGAAGAC AGTAGCGAAG    5220
GCTCACTCTT TTCGAGCTTT AGCGGATCGG ACAACTACCG AAGGCAGGTG GTGGTGGCTG    5280
ACGTCCATGC CGTCCAAGAG CCTGCCCCTG TTCCACCGCC AAGGCTAAAG AAGATGGCCC    5340
GCCTGGCAGC GGCAAGAATG CAGGAAGAGC CAACTCCACC GGCAAGCACC AGCTCTGCGG    5400
ACGAGTCCCT TCACCTTTCT TTTGATGGGG TATCTATATC CTTCGGATCC CTTTTCGACG    5460
GAGAGATGGC CCGCTTGGCA GCGGCACAAC CCCCGGCAAG TACATGCCCT ACGGATGTGC    5520
CTATGTCTTT CGGATCGTTT TCCGACGGAG AGATTGAGGA GTTGAGCCGC AGAGTAACCG    5580
AGTCGGAGCC CGTCCTGTTT GGGTCATTTG AACCGGGCGA AGTGAACTCA ATTATATCGT    5640
CCCGATCAGC CGTATCTTTT CCACCACGCA AGCAGAGACG TAGACGCAGG AGCAGGAGGA    5700
CCGAATACTG TCTAACCGGG GTAGGTGGGT ACATATTTTC GACGGACACA GGCCCTGGGC    5760
ACTTGCAAAA GAAGTCCGTT CTGCAGAACC AGCTTACAGA ACCGACCTTG GAGCGCAATG    5820
TTCTGGAAAG AATCTACGCC CCGGTGCTCG ACACGTCGAA AGAGGAACAG CTCAAACTCA    5880
GGTACCAGAT GATGCCCACC GAAGCCAACA AAAGCAGGTA CCAGTCTCGA AAAGTAGAAA    5940
ACCAGAAAGC CATAACCACT GAGCGACTGC TTTCAGGGCT ACGGCTGTAT AACTCTGCCA    6000
CAGATCAGCC AGAATGCTAT AAGATCACCT ACCCGAAACC ATCGTATTCC AGCAGTGTAC    6060
CAGCGAACTA CTCTGACCCA AAGTTTGCTG TAGCTGTTTG TAACAACTAT CTGCATGAGA    6120
ATTACCCGAC GGTAGCATCT TATCAGATCA CCGACGAGTA CGATGCTTAC TTGGATATGG    6180
TAGACGGGAC AGTCGCTTGC CTAGATACTG CAACTTTTTG CCCCGCCAAG CTTAGAAGTT    6240
ACCCGAAAAG ACACGAGTAT AGAGCCCCAA ACATCCGCAG TGCGGTTCCA TCAGCGATGC    6300
AGAACACGTT GCAAAACGTG CTCATTGCCG CGACTAAAAG AAACTGCAAC GTCACACAAA    6360
TGCGTGAACT GCCAACACTG GACTCAGCGA CATTCAACGT TGAATGCTTT CGAAAATATG    6420
CATGCAATGA CGAGTATTGG GAGGAGTTTG CCCGAAAGCC AATTAGGATC ACTACTGAGT    6480
TCGTTACCGC ATACGTGGCC AGACTGAAAG GCCCTAAGGC CGCCGCACTG TTCGCAAAGA    6540
```

```
CGCATAATTT GGTCCCATTG CAAGAAGTGC CTATGGATAG ATTCGTCATG GACATGAAAA   6600

GAGACGTGAA AGTTACACCT GGCACGAAAC ACACAGAAGA AAGACCGAAA GTACAAGTGA   6660

TACAAGCCGC AGAACCCCTG GCGACCGCTT ACCTATGCGG GATCCACCGG GAGTTAGTGC   6720

GCAGGCTTAC AGCCGTTTTG CTACCCAACA TTCACACGCT CTTTGACATG TCGGCGGAGG   6780

ACTTTGATGC AATCATAGCA GAACACTTCA AGCAAGGTGA CCCGGTACTG GAGACGGATA   6840

TCGCCTCGTT CGACAAAAGC CAAGACGACG CTATGGCGTT AACCGGCCTG ATGATCTTGG   6900

AAGACCTGGG TGTGGACCAA CCACTACTCG ACTTGATCGA GTGCGCCTTT GGAGAAATAT   6960

CATCCACCCA TCTGCCCACG GGTACCCGTT TCAAATTCGG GGCGATGATG AAATCCGGAA   7020

TGTTCCTCAC GCTCTTTGTC AACACAGTTC TGAATGTCGT TATCGCCAGC AGAGTATTGG   7080

AGGAGCGGCT TAAAACGTCC AAATGTGCAG CATTTATCGG CGACGACAAC ATTATACACG   7140

GAGTAGTATC TGACAAAGAA ATGGCTGAGA GGTGTGCCAC CTGGCTCAAC ATGGAGGTTA   7200

AGATCATTGA CGCAGTCATC GGCGAGAGAC CACCTTACTT CTGCGGTGGA TTCATCTTGC   7260

AAGATTCGGT TACCTCCACA GCGTGTCGCG TGGCGGACCC CTTGAAAAGG CTGTTTAAGT   7320

TGGGTAAACC GCTCCCAGCC GACGATGAGC AAGACGAAGA CAGAAGACGC GCTCTGCTAG   7380

ATGAAACAAA GGCGTGGTTT AGAGTAGGTA TAACAGACAC CTTAGCAGTG GCCGTGGCAA   7440

CTCGGTATGA GGTAGACAAC ATCACACCTG TCCTGCTGGC ATTGAGAACT TTTGCCCAGA   7500

GCAAAGAGC ATTTCAAGCC ATCAGAGGGG AAATAAAGCA TCTCTACGGT GGTCCTAAAT   7560

AGTCAGCATA GTACATTTCA TCTGACTAAT ACCACAACAC CACCACCATG AATAGAGGAT   7620

TCTTTAACAT GCTCGGCCGC CGCCCCTTCC CAGCCCCCAC TGCCATGTGG AGGCCGCGGA   7680

GAAGGAGGCA GGCGGCCCCG ATGCCTGCCC GCAATGGGCT GGCTTCCCAA ATCCAGCAAC   7740

TGACCACAGC CGTCAGTGCC CTAGTCATTG GACAGGCAAC TAGACCTCAA ACCCCACGCC   7800

CACGCCCGCC GCCGCGCCAG AAGAAGCAGG CGCCAAAGCA ACCACCGAAG CCGAAGAAAC   7860

CAAAACACA GGAGAAGAAG AAGAAGCAAC CTGCAAAACC CAAACCCGGA AAGAGACAGC   7920

GTATGGCACT TAAGTTGGAG GCCGACAGAC TGTTCGACGT CAAAAATGAG GACGGAGATG   7980

TCATCGGGCA CGCACTGGCC ATGGAAGGAA AGGTAATGAA ACCACTCCAC GTGAAAGGAA   8040

CTATTGACCA CCCTGTGCTA TCAAAGCTCA AATTCACCAA GTCGTCAGCA TACGACATGG   8100

AGTTCGCACA GTTGCCGGTC AACATGAGAA GTGAGGCGTT CACCTACACC AGTGAACACC   8160

CTGAAGGGTT CTACAACTGG CACCACGGAG CGGTGCAGTA TAGTGGAGGC AGATTTACCA   8220

TCCCCCGCGG AGTAGGAGGC AGAGGAGACA GTGGTCGTCC GATTATGGAT AACTCAGGCC   8280

GGGTTGTCGC GATAGTCCTC GGAGGGGCTG ATGAGGGAAC AAGAACCGCC CTTTCGGTCG   8340

TCACCTGGAA TAGCAAAGGG AAGACAATCA AGACAACCCC GGAAGGGACA GAAGAGTGGT   8400

CTGCTGCACC ACTGGTCACG GCCATGTGCT TGCTTGGAAA CGTGAGCTTC CCATGCAATC   8460

GCCCGCCCAC ATGCTACACC CGCGAACCAT CCAGAGCTCT CGACATCCTC GAAGAGAACG   8520

TGAACCACGA GGCCTACGAC ACCCTGCTCA ACGCCATATT GCGGTGCGGA TCGTCCGGCA   8580

GAAGTAAAAG AAGCGTCACT GACGACTTTA CCTTGACCAG CCCGTACTTG GGCACATGCT   8640

CGTACTGTCA CCATACTGAA CCGTGCTTTA GCCCGATTAA GATCGAGCAG GTCTGGGATG   8700

AAGCGGACGA CAACACCATA CGCATACAGA CTTCCGCCCA GTTTGGATAC GACCAAAGCG   8760

GAGCAGCAAG CTCAAATAAG TACCGCTACA TGTCGCTCGA GCAGGATCAT ACTGTCAAAG   8820

AAGGCACCAT GGATGACATC AAGATCAGCA CCTCAGGACC GTGTAGAAGG CTTAGCTACA   8880

AAGGATACTT TCTCCTCGCG AAGTGTCCTC CAGGGGACAG CGTAACGGTT AGCATAGCGA   8940
```

```
GTAGCAACTC AGCAACGTCA TGCACAATGG CCCGCAAGAT AAAACCAAAA TTCGTGGGAC    9000

GGGAAAAATA TGACCTACCT CCCGTTCACG GTAAGAAGAT TCCTTGCACA GTGTACGACC    9060

GTCTGAAAGA AACAACCGCC GGCTACATCA CTATGCACAG GCCGGGACCG CACGCCTATA    9120

CATCCTATCT GGAGGAATCA TCAGGGAAAG TTTACGCGAA GCCACCATCC GGGAAGAACA    9180

TTACGTACGA GTGCAAGTGC GGCGATTACA AGACCGGAAC CGTTACGACC CGTACCGAAA    9240

TCACGGGCTG CACCGCCATC AAGCAGTGCG TCGCCTATAA GAGCGACCAA ACGAAGTGGG    9300

TCTTCAACTC GCCGGACTCG ATCAGACACG CCGACCACAC GGCCCAAGGG AAATTGCATT    9360

TGCCTTTCAA GCTGATCCCG AGTACCTGCA TGGTCCCTGT TGCCCACGCG CCGAACGTAG    9420

TACACGGCTT TAAACACATC AGCCTCCAAT TAGACACAGA CCATCTGACA TTGCTCACCA    9480

CCAGGAGACT AGGGGCAAAC CCGGAACCAA CCACTGAATG GATCATCGGA AACACGGTTA    9540

GAAACTTCAC CGTCGACCGA GATGGCCTGG AATACATATG GGGCAATCAC GAACCAGTAA    9600

GGGTCTATGC CCAAGAGTCT GCACCAGGAG ACCCTCACGG ATGGCCACAC GAAATAGTAC    9660

AGCATTACTA TCATCGCCAT CCTGTGTACA CCATCTTAGC CGTCGCATCA GCTGCTGTGG    9720

CGATGATGAT TGGCGTAACT GTTGCAGCAT TATGTGCCTG TAAAGCGCGC CGTGAGTGCC    9780

TGACGCCATA TGCCCTGGCC CCAAATGCCG TGATTCCAAC TTCGCTGGCA CTTTTGTGCT    9840

GTGTTAGGTC GGCTAATGCT GAAACATTCA CCGAGACCAT GAGTTACTTA TGGTCGAACA    9900

GCCAGCCGTT CTTCTGGGTC CAGCTGTGTA TACCTCGGC CGCTGTCGTC GTTCTAATGC    9960

GCTGTTGCTC ATGCTGCCTG CCTTTTTTAG TGGTTGCCGG CGCCTACCTG GCGAAGGTAG   10020

ACGCCTACGA ACATGCGACC ACTGTTCCAA ATGTGCCACA GATACCGTAT AAGGCACTTG   10080

TTGAAAGGGC AGGGTACGCC CCGCTCAATT TGGAGATTAC TGTCATGTCC TCGGAGGTTT   10140

TGCCTTCCAC CAACCAAGAG TACATTACCT GCAAATTCAC CACTGTGGTC CCCTCCCCTA   10200

AAGTCAGATG CTGCGGCTCC TTGGAATGTC AGCCCGCCGC TCACGCAGAC TATACCTGCA   10260

AGGTCTTTGG AGGGGTGTAC CCCTTCATGT GGGGAGGAGC ACAATGTTTT TGCGACAGTG   10320

AGAACAGCCA GATGAGTGAG GCGTACGTCG AATTGTCAGT AGATTGCGCG ACTGACCACG   10380

CGCAGGCGAT TAAGGTGCAT ACTGCCGCGA TGAAAGTAGG ACTGCGTATA GTGTACGGGA   10440

ACACTACCAG TTTCCTAGAT GTGTACGTGA ACGGAGTCAC ACCAGGAACG TCTAAAGACC   10500

TGAAAGTCAT AGCTGGACCA ATTTCAGCAT TGTTTACACC ATTCGATCAC AAGGTCGTTA   10560

TCAATCGCGG CCTGGTGTAC AACTATGACT TTCCGGAATA CGGAGCGATG AAACCAGGAG   10620

CGTTTGGAGA CATTCAAGCT ACCTCCTTGA CTAGCAAAGA CCTCATCGCC AGCACAGACA   10680

TTAGGCTACT CAAGCCTTCC GCCAAGAACG TGCATGTCCC GTACACGCAG GCCGCATCTG   10740

GATTCGAGAT GTGGAAAAAC AACTCAGGCC GCCCACTGCA GGAAACCGCC CCTTTTGGGT   10800

GCAAGATTGC AGTCAATCCG CTTCGAGCGG TGGACTGCTC ATACGGGAAC ATTCCCATTT   10860

CTATTGACAT CCCGAACGCT GCCTTTATCA GGACATCAGA TGCACCACTG GTCTCAACAG   10920

TCAAATGTGA TGTCAGTGAG TGCACTTATT CAGCGGACTT CGGAGGGATG GCTACCCTGC   10980

AGTATGTATC CGACCGCGAA GGACAATGCC CTGTACATTC GCATTCGAGC ACAGCAACCC   11040

TCCAAGAGTC GACAGTTCAT GTCCTGGAGA AAGGAGCGGT GACAGTACAC TTCAGCACCG   11100

CGAGCCCACA GGCGAACTTC ATTGTATCGC TGTGTGGTAA GAAGACAACA TGCAATGCAG   11160

AATGCAAACC ACCAGCTGAT CATATCGTGA GCACCCCGCA CAAAAATGAC CAAGAATTCC   11220

AAGCCGCCAT CTCAAAAACT TCATGGAGTT GGCTGTTTGC CCTTTTCGGC GGCGCCTCGT   11280

CGCTATTAAT TATAGGACTT ATGATTTTTG CTTGCAGCAT GATGCTGACT AGCACACGAA   11340
```

```
GATGACCGCT ACGCCCCAAT GACCCGACCA GCAAAACTCG ATGTACTTCC GAGGAACTGA    11400

TGTGCATAAT GCATCAGGCT GGTATATTAG ATCCCCGCTT ACCGCGGGCA ATATAGCAAC    11460

ACCAAAACTC GACGTATTTC CGAGGAAGCG CAGTGCATAA TGCTGCGCAG TGTTGCCAAA    11520

TAATCACTAT ATTAACCATT TATTCAGCGG ACGCCAAAAC TCAATGTATT TCTGAGGAAG    11580

CATGGTGCAT AATGCCATGC AGCGTCTGCA TAACTTTTTA TTATTTCTTT TATTAATCAA    11640

CAAAATTTTG TTTTTAACAT TTC                                           11663
```

(2) INFORMATION FOR SEQ ID NO:8:

(i) SEQUENCE CHARACTERISTICS:
        (A) LENGTH: 11703 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

```
ATTGGCGGCG TAGTACACAC TATTGAATCA AACAGCCGAC CAATTGCACT ACCATCACA      59

ATG GAG AAG CCA GTA GTA AAC GTA GAC GTA GAC CCC CAG AGT CCG TTT     107

GTC GTG CAA CTG CAA AAA AGC TTC CCG CAA TTT GAG GTA GTA GCA CAG     155

CAG GTC ACT CCA AAT GAC CAT GCT AAT GCC AGA GCA TTT TCG CAT CTG     203

GCC AGT AAA CTA ATC GAG CTG GAG GTT CCT ACC ACA GCG ACG ATC TTG     251

GAC ATA GGC AGC GCA CCG GCT CGT AGA ATG TTT TCC GAG CAC CAG TAT     299

CAT TGT GTC TGC CCC ATG CGT AGT CCA GAA GAC CCG GAC CGC ATG ATG     347

AAA TAT GCC AGT AAA CTG GCG GAA AAA GCG TGC AAG ATT ACA AAC AAG     395

AAC TTG CAT GAG AAG ATT AAG GAT CTC CGG ACC GTA CTT GAT ACG CCG     443

GAT GCT GAA ACA CCA TCG CTC TGC TTT CAC AAC GAT GTT ACC TGC AAC     491

ATG CGT GCC GAA TAT TCC GTC ATG CAG GAC GTG TAT ATC AAC GCT CCC     539

GGA ACT ATC TAT CAT CAG GCT ATG AAA GGC GTG CGG ACC CTG TAC TGG     587

ATT GGC TTC GAC ACC ACC CAG TTC ATG TTC TCG GCT ATG GCA GGT TCG     635

TAC CCT GCG TAC AAC ACC AAC TGG GCC GAC GAG AAA GTC CTT GAA GCG     683

CGT AAC ATC GGA CTT TGC AGC ACA AAG CTG AGT GAA GGT AGG ACA GGA     731

AAA TTG TCG ATA ATG AGG AAG AAG GAG TTG AAG CCC GGG TCG CGG GTT     779

TAT TTC TCC GTA GGA TCG ACA CTT TAT CCA GAA CAC AGA GCC AGC TTG     827

CAG AGC TGG CAT CTT CCA TCG GTG TTC CAC TTG AAT GGA AAG CAG TCG     875

TAC ACT TGC CGC TGT GAT ACA GTG GTG AGT TGC GAA GGC TAC GTA GTG     923

AAG AAA ATC ACC ATC AGT CCC GGG ATC ACG GGA GAA ACC GTG GGA TAC     971

GCG GTT ACA CAC AAT AGC GAG GGC TTC TTG CTA TGC AAA GTT ACT GAC    1019

ACA GTA AAA GGA GAA CGG GTA TCG TTC CCT GTG TGC ACG TAC ATC CCG    1067

GCC ACC ATA TGC GAT CAG ATG ACT GGT ATA ATG GCC ACG GAT ATA TCA    1115

CCT GAC GAT GCA CAA AAA CTT CTG GTT GGG CTC AAC CAG CGA ATT GTC    1163

ATT AAC GGT AGG ACT AAC AGG AAC ACC AAC ACC ATG CAA AAT TAC CTT    1211

CTG CCG ATC ATA GCA CAA GGG TTC AGC AAA TGG GCT AAG GAG CGC AAG    1259

GAT GAT CTT GAT AAC GAG AAA ATG CTG GGT ACT AGA GAA CGC AAG CTT    1307
```

-continued

| | |
|---|---|
| ACG TAT GGC TGC TTG TGG GCG TTT CGC ACT AAG AAA GTA CAT TCG TTT | 1355 |
| TAT CGC CCA CCT GGA ACG CAG ACC ATC GTA AAA GTC CCA GCC TCT TTT | 1403 |
| AGC GCT TTT CCC ATG TCG TCC GTA TGG ACG ACC TCT TTG CCC ATG TCG | 1451 |
| CTG AGG CAG AAA TTG AAA CTG GCA TTG CAA CCA AAG AAG GAG GAA AAA | 1499 |
| CTG CTG CAG GTC TCG GAG GAA TTA GTC ATG GAG GCC AAG GCT GCT TTT | 1547 |
| GAG GAT GCT CAG GAG GAA GCC AGA GCG GAG AAG CTC CGA GAA GCA CTT | 1595 |
| CCA CCA TTA GTG GCA GAC AAA GGC ATC GAG GCA GCC GCA GAA GTT GTC | 1643 |
| TGC GAA GTG GAG GGG CTC CAG GCG GAC ATC GGA GCA GCA TTA GTT GAA | 1691 |
| ACC CCG CGC GGT CAC GTA AGG ATA ATA CCT CAA GCA AAT GAC CGT ATG | 1739 |
| ATC GGA CAG TAT ATC GTT GTC TCG CCA AAC TCT GTG CTG AAG AAT GCC | 1787 |
| AAA CTC GCA CCA GCG CAC CCG CTA GCA GAT CAG GTT AAG ATC ATA ACA | 1835 |
| CAC TCC GGT AGA TCA GGA AGG TAC GCG GTC GAA CCA TAC GAC GCT AAA | 1883 |
| GTA CTG ATG CCA GCA GGA GGT GCC GTA CCA TGG CCA GAA TTC CTA GCA | 1931 |
| CTG AGT GAG AGC GCC ACG TTA GTG TAC AAC GAA AGA GAG TTT GTG AAC | 1979 |
| CGC AAA CTA TAC CAC ATT GCC ATG CAT GGC CCC GCC AAG AAT ACA GAA | 2027 |
| GAG GAG CAG TAC AAG GTT ACA AAG GCA GAG CTT GCA GAA ACA GAG TAC | 2075 |
| GTG TTT GAC GTG GAC AAG AAG CGT TGC GTT AAG AAG GAA GAA GCC TCA | 2123 |
| GGT CTG GTC CTC TCG GGA GAA CTG ACC AAC CCT CCC TAT CAT GAG CTA | 2171 |
| GCT CTG GAG GGA CTG AAG ACC CGA CCT GCG GTC CCG TAC AAG GTC GAA | 2219 |
| ACA ATA GGA GTG ATA GGC ACA CCG GGG TCG GGC AAG TCA GCT ATT ATC | 2267 |
| AAG TCA ACT GTC ACG GCA CGG GAT CTT GTT ACC AGC GGA AAG AAA GAA | 2315 |
| AAT TGT CGC GAA ATT GAG GCC GAC GTG CTA AGA CTG AGG GGT ATG CAG | 2363 |
| ATT ACG TCG AAG ACA GTA GAT TCG GTT ATG CTC AAC GGA TGC CAC AAA | 2411 |
| GCC GTA GAA GTG CTG TAC GTT GAC GAA GCG TTC GCG TGC CAC GCA GGA | 2459 |
| GCA CTA CTT GCC TTG ATT GCT ATC GTC AGG CCC CGC AAG AAG GTA GTA | 2507 |
| CTA TGC GGA GAC CCC ATG CAA TGC GGA TTC TTC AAC ATG ATG CAA CTA | 2555 |
| AAG GTA CAT TTC AAT CAC CCT GAA AAA GAC ATA TGC ACC AAG ACA TTC | 2603 |
| TAC AAG TAT ATC TCC CGG CGT TGC ACA CAG CCA GTT ACA GCT ATT GTA | 2651 |
| TCG ACA CTG CAT TAC GAT GGA AAG ATG AAA ACC ACG AAC CCG TGC AAG | 2699 |
| AAG AAC ATT GAA ATC GAT ATT ACA GGG GCC ACA AAG CCG AAG CCA GGG | 2747 |
| GAT ATC ATC CTG ACA TGT TTC CGC GGG TGG GTT AAG CAA TTG CAA ATC | 2795 |
| GAC TAT CCC GGA CAT GAA GTA ATG ACA GCC GCG GCC TCA CAA GGG CTA | 2843 |
| ACC AGA AAA GGA GTG TAT GCC GTC CGG CAA AAA GTC AAT GAA AAC CCA | 2891 |
| CTG TAC GCG ATC ACA TCA GAG CAT GTG AAC GTG TTG CTC ACC CGC ACT | 2939 |
| GAG GAC AGG CTA GTG TGG AAA ACC TTG CAG GGC GAC CCA TGG ATT AAG | 2987 |
| CAG CTC ACT AAC ATA CCT AAA GGA AAC TTT CAG GCT ACT ATA GAG GAC | 3035 |
| TGG GAA GCT GAA CAC AAG GGA ATA ATT GCT GCA ATA AAC AGC CCC ACT | 3083 |
| CCC CGT GCC AAT CCG TTC AGC TGC AAG ACC AAC GTT TGC TGG GCG AAA | 3131 |
| GCA TTG GAA CCG ATA CTA GCC ACG GCC GGT ATC GTA CTT ACC GGT TGC | 3179 |
| CAG TGG AGC GAA CTG TTC CCA CAG TTT GCG GAT GAC AAA CCA CAT TCG | 3227 |

```
GCC ATT TAC GCC TTA GAC GTA ATT TGC ATT AAG TTT TTC GGC ATG GAC      3275
TTG ACA AGC GGA CTG TTT TCT AAA CAG AGC ATC CCA CTA ACG TAC CAT      3323
CCC GCC GAT TCA GCG AGG CCG GTA GCT CAT TGG GAC AAC AGC CCA GGA      3371
ACC CGC AAG TAT GGG TAC GAT CAC GCC ATT GCC GCC GAA CTC TCC CGT      3419
AGA TTT CCG GTG TTC CAG CTA GCT GGG AAG GGC ACA CAA CTT GAT TTG      3467
CAG ACG GGG AGA ACC AGA GTT ATC TCT GCA CAG CAT AAC CTG GTC CCG      3515
GTG AAC CGC AAT CTT CCT CAC GCC TTA GTC CCC GAG TAC AAG GAG AAG      3563
CAA CCC GGC CCG GTC GAA AAA TTC TTG AAC CAG TTC AAA CAC CAC TCA      3611
GTA CTT GTG GTA TCA GAG GAA AAA ATT GAA GCT CCC CGT AAG AGA ATC      3659
GAA TGG ATC GCC CCG ATT GGC ATA GCC GGT GCA GAT AAG AAC TAC AAC      3707
CTG GCT TTC GGG TTT CCG CCG CAG GCA CGG TAC GAC CTG GTG TTC ATC      3755
AAC ATT GGA ACT AAA TAC AGA AAC CAC CAC TTT CAG CAG TGC GAA GAC      3803
CAT GCG GCG ACC TTA AAA ACC CTT TCG CGT TCG GCC CTG AAT TGC CTT      3851
AAC CCA GGA GGC ACC CTC GTG GTG AAG TCC TAT GGC TAC GCC GAC CGC      3899
AAC AGT GAG GAC GTA GTC ACC GCT CTT GCC AGA AAG TTT GTC AGG GTG      3947
TCC GCA GCG AGA CCA GAT TGT GTC TCA AGC AAT ACA GAA ATG TAC CTG      3995
ATT TTC CGA CAA CTA GAC AAC AGC CGT ACA CGG CAA TTC ACC CCG CAC      4043
CAT CTG AAT TGC GTG ATT TCG TCC GTG TAT GAG GGT ACA AGA GAT GGA      4091
GTT GGA GCC GCG CCG TCA TAC CGC ACC AAA AGG GAG AAT ATT GCT GAC      4139
TGT CAA GAG GAA GCA GTT GTC AAC GCA GCC AAT CCG CTG GGT AGA CCA      4187
GGC GAA GGA GTC TGC CGT GCC ATC TAT AAA CGT TGG CCG ACC AGT TTT      4235
ACC GAT TCA GCC ACG GAG ACA GGC ACC GCA AGA ATG ACT GTG TGC CTA      4283
GGA AAG AAA GTG ATC CAC GCG GTC GGC CCT GAT TTC CGG AAG CAC CCA      4331
GAA GCA GAA GCC TTG AAA TTG CTA CAA AAC GCC TAC CAT GCA GTG GCA      4379
GAC TTA GTA AAT GAA CAT AAC ATC AAG TCT GTC GCC ATT CCA CTG CTA      4427
TCT ACA GGC ATT TAC GCA GCC GGA AAA GAC CGC CTT GAA GTA TCA CTT      4475
AAC TGC TTG ACA ACC GCG CTA GAC AGA ACT GAC GCG GAC GTA ACC ATC      4523
TAT TGC CTG GAT AAG AAG TGG AAG GAA AGA ATC GAC GCG GCA CTC CAA      4571
CTT AAG GAG TCT GTA ACA GAG CTG AAG GAT GAA GAT ATG GAG ATC GAC      4619
GAT GAG TTA GTA TGG ATC CAT CCA GAC AGT TGC TTG AAG GGA AGA AAG      4667
GGA TTC AGT ACT ACA AAA GGA AAA TTG TAT TCG TAC TTC GAA GGC ACC      4715
AAA TTC CAT CAA GCA GCA AAA GAC ATG GCG GAG ATA AAG GTC CTG TTC      4763
CCT AAT GAC CAG GAA AGT AAT GAA CAA CTG TGT GCC TAC ATA TTG GGT      4811
GAG ACC ATG GAA GCA ATC CGC GAA AAG TGC CCG GTC GAC CAT AAC CCG      4859
TCG TCT AGC CCG CCC AAA ACG TTG CCG TGC CTT TGC ATG TAT GCC ATG      4907
ACG CCA GAA AGG GTC CAC AGA CTT AGA AGC AAT AAC GTC AAA GAA GTT      4955
ACA GTA TGC TCC TCC ACC CCC CTT CCT AAG CAC AAA ATT AAG AAT GTT      5003
CAG AAG GTT CAG TGC ACG AAA GTA GTC CTG TTT AAT CCG CAC ACT CCC      5051
GCA TTC GTT CCC GCC CGT AAG TAC ATA GAA GTG CCA GAA CAG CCT ACC      5099
GCT CCT CCT GCA CAG GCC GAG GAG GCC CCC GAA GTT GTA GCG ACA CCG      5147
```

```
TCA CCA TCT ACA GCT GAT AAC ACC TCG CTT GAT GTC ACA GAC ATC TCA    5195

CTG GAT ATG GAT GAC AGT AGC GAA GGC TCA CTT TTT TCG AGC TTT AGC    5243

GGA TCG GAC AAC TCT ATT ACT AGT ATG GAC AGT TGG TCG TCA GGA CCT    5291

AGT TCA CTA GAG ATA GTA GAC CGA AGG CAG GTG GTG GTG GCT GAC GTT    5339

CAT GCC GTC CAA GAG CCT GCC CCT ATT CCA CCG CCA AGG CTA AAG AAG    5387

ATG GCC CGC CTG GCA GCG GCA AGA AAA GAG CCC ACT CCA CCG GCA AGC    5435

AAT AGC TCT GAG TCC CTC CAC CTC TCT TTT GGT GGG GTA TCC ATG TCC    5483

CTC GGA TCA ATT TTC GAC GGA GAG ACG GCC CGC CAG GCA GCG GTA CAA    5531

CCC CTG GCA ACA GGC CCC ACG GAT GTG CCT ATG TCT TTC GGA TCG TTT    5579

TCC GAC GGA GAG ATT GAT GAG CTG AGC CGC AGA GTA ACT GAG TCC GAA    5627

CCC GTC CTG TTT GGA TCA TTT GAA CCG GGC GAA GTG AAC TCA ATT ATA    5675

TCG TCC CGA TCA GCC GTA TCT TTT CCA CTA CGC AAG CAG AGA CGT AGA    5723

CGC AGG AGC AGG AGG ACT GAA TAC TGA CTA ACC GGG GTA GGT GGG TAC    5771

ATA TTT TCG ACG GAC ACA GGC CCT GGG CAC TTG CAA AAG AAG TCC GTT    5819

CTG CAG AAC CAG CTT ACA GAA CCG ACC TTG GAG CGC AAT GTC CTG GAA    5867

AGA ATT CAT GCC CCG GTG CTC GAC ACG TCG AAA GAG GAA CAA CTC AAA    5915

CTC AGG TAC CAG ATG ATG CCC ACC GAA GCC AAC AAA AGT AGG TAC CAG    5963

TCT CGT AAA GTA GAA AAT CAG AAA GCC ATA ACC ACT GAG CGA CTA CTG    6011

TCA GGA CTA CGA CTG TAT AAC TCT GCC ACA GAT CAG CCA GAA TGC TAT    6059

AAG ATC ACC TAT CCG AAA CCA TTG TAC TCC AGT AGC GTA CCG GCG AAC    6107

TAC TCC GAT CCA CAG TTC GCT GTA GCT GTC TGT AAC AAC TAT CTG CAT    6155

GAG AAC TAT CCG ACA GTA GCA TCT TAT CAG ATT ACT GAC GAG TAC GAT    6203

GCT TAC TTG GAT ATG GTA GAC GGG ACA GTC GCC TGC CTG GAT ACT GCA    6251

ACC TTC TGC CCC GCT AAG CTT AGA AGT TAC CCG AAA AAA CAT GAG TAT    6299

AGA GCC CCG AAT ATC CGC AGT GCG GTT CCA TCA GCG ATG CAG AAC ACG    6347

CTA CAA AAT GTG CTC ATT GCC GCA ACT AAA AGA AAT TGC AAC GTC ACG    6395

CAG ATG CGT GAA CTG CCA ACA CTG GAC TCA GCG ACA TTC AAT GTC GAA    6443

TGC TTT CGA AAA TAT GCA TGT AAT GAC GAG TAT TGG GAG GAG TTC GCT    6491

CGG AAG CCA ATT AGG ATT ACC ACT GAG TTT GTC ACC GCA TAT GTA GCT    6539

AGA CTG AAA GGC CCT AAG GCC GCC GCA CTA TTT GCA AAG ACG TAT AAT    6587

TTG GTC CCA TTG CAA GAA GTG CCT ATG GAT AGA TTC GTC ATG GAC ATG    6635

AAA AGA GAC GTG AAA GTT ACA CCA GGC ACG AAA CAC ACA GAA GAA AGA    6683

CCG AAA GTA CAA GTG ATA CAA GCC GCA GAA CCC CTG GCG ACT GCT TAC    6731

TTA TGC GGG ATT CAC CGG GAA TTA GTG CGT AGG CTT ACG GCC GTC TTG    6779

CTT CCA AAC ATT CAC ACG CTT TTT GAC ATG TCG GCG GAG GAT TTT GAT    6827

GCA ATC ATA GCA GAA CAC TTC AAG CAA GGC GAC CCG GTA CTG GAG ACG    6875

GAT ATC GCA TCA TTC GAC AAA AGC CAA GAC GAC GCT ATG GCG TTA ACC    6923

GGT CTG ATG ATC TTG GAG GAC CTG GGT GTG GAT CAA CCA CTA CTC GAC    6971

TTG ATC GAG TGC GCC TTT GGA GAA ATA TCA TCC ACC CAT CTA CCT ACG    7019

GGT ACT CGT TTT AAA TTC GGG GCG ATG ATG AAA TCC GGA ATG TTC CTC    7067
```

```
ACA CTT TTT GTC AAC ACA GTT TTG AAT GTC GTT ATC GCC AGC AGA GTA       7115

CTA GAA GAG CGG CTT AAA ACG TCC AGA TGT GCA GCG TTC ATT GGC GAC       7163

GAC AAC ATC ATA CAT GGA GTA GTA TCT GAC AAA GAA ATG GCT GAG AGG       7211

TGC GCC ACC TGG CTC AAC ATG GAG GTT AAG ATC ATC GAC GCA GTC ATC       7259

GGT GAG AGA CCA CCT TAC TTC TGC GGC GGA TTT ATC TTG CAA GAT TCG       7307

GTT ACT TCC ACA GCG TGC CGC GTG GCG GAC CCC CTG AAA AGG CTG TTT       7355

AAG TTG GGT AAA CCG CTC CCA GCC GAC GAC GAG CAA GAC GAA GAC AGA       7403

AGA CGC GCT CTG CTA GAT GAA ACA AAG GCG TGG TTT AGA GTA GGT ATA       7451

ACA GGC ACT TTA GCA GTG GCC GTG ACG ACC CGG TAT GAG GTA GAC AAT       7499

ATT ACA CCT GTC CTA CTG GCA TTG AGA ACT TTT GCC CAG AGC AAA AGA       7547

GCA TTC CAA GCC ATC AGA GGG GAA ATA AAG CAT CTC TAC GGT GGT CCT       7595

AAA TAGTCAGCAT AGTACATTTC ATCTGACTAA TACTACAACA CCACCACC ATG AAT      7652

AGA GGA TTC TTT AAC ATG CTC GGC CGC CGC CCC TTC CCG GCC CCC ACT       7700

GCC ATG TGG AGG CCG CGG AGA AGG AGG CAG GCG GCC CCG ATG CCT GCC       7748

CGC AAC GGG CTG GCT TCT CAA ATC CAG CAA CTG ACC ACA GCC GTC AGT       7796

GCC CTA GTC ATT GGA CAG GCA ACT AGA CCT CAA CCC CCA CGT CCA CGC       7844

CCG CCA CCG CGC CAG AAG AAG CAG GCG CCC AAG CAA CCA CCG AAG CCG       7892

AAG AAA CCA AAA ACG CAG GAG AAG AAG AAG AAG CAA CCT GCA AAA CCC       7940

AAA CCC GGA AAG AGA CAG CGC ATG GCA CTT AAG TTG GAG GCC GAC AGA       7988

TTG TTC GAC GTC AAG AAC GAG GAC GGA GAT GTC ATC GGG CAC GCA CTG       8036

GCC ATG GAA GGA AAG GTA ATG AAA CCT CTG CAC GTG AAA GGA ACC ATC       8084

GAC CAC CCT GTG CTA TCA AAG CTC AAA TTT ACC AAG TCG TCA GCA TAC       8132

GAC ATG GAG TTC GCA CAG TTG CCA GTC AAC ATG AGA AGT GAG GCA TTC       8180

ACC TAC ACC AGT GAA CAC CCC GAA GGA TTC TAT AAC TGG CAC CAC GGA       8228

GCG GTG CAG TAT AGT GGA GGT AGA TTT ACC ATC CCT CGC GGA GTA GGA       8276

GGC AGA GGA GAC AGC GGT CGT CCG ATC ATG GAT AAC TCC GGT CGG GTT       8324

GTC GCG ATA GTC CTC GGT GGA GCT GAT GAA GGA ACA CGA ACT GCC CTT       8372

TCG GTC GTC ACC TGG AAT AGT AAA GGG AAG ACA ATT AAG ACG ACC CCG       8420

GAA GGG ACA GAA GAG TGG TCC GCA GCA CCA CTG GTC ACG GCA ATG TGT       8468

TTG CTC GGA AAT GTG AGC TTC CCA TGC GAC CGC CCG CCC ACA TGC TAT       8516

ACC CGC GAA CCT TCC AGA GCC CTC GAC ATC CTT GAA GAG AAC GTG AAC       8564

CAT GAG GCC TAC GAT ACC CTG CTC AAT GCC ATA TTG CGG TGC GGA TCG       8612

TCT GGC AGA AGC AAA AGA AGC GTC ACT GAC GAC TTT ACC CTG ACC AGC       8660

CCC TAC TTG GGC ACA TGC TCG TAC TGC CAC CAT ACT GAA CCG TGC TTC       8708

AGC CCT GTT AAG ATC GAG CAG GTC TGG GAC GAA GCG GAC GAT AAC ACC       8756

ATA CGC ATA CAG ACT TCC GCC CAG TTT GGA TAC GAC CAA AGC GGA GCA       8804

GCA AGC GCA AAC AAG TAC CGC TAC ATG TCG CTT GAG CAG GAT CAC ACC       8852

GTT AAA GAA GGC ACC ATG GAT GAC ATC AAG ATT AGC ACC TCA GGA CCG       8900

TGT AGA AGG CTT AGC TAC AAA GGA TAC TTT CTC CTC GCA AAA TGC CCT       8948

CCA GGG GAC AGC GTA ACG GTT AGC ATA GTG AGT AGC AAC TCA GCA ACG       8996
```

-continued

| | |
|---|---|
| TCA TGT ACA CTG GCC CGC AAG ATA AAA CCA AAA TTC GTG GGA CGG GAA | 9044 |
| AAA TAT GAT CTA CCT CCC GTT CAC GGT AAA AAA ATT CCT TGC ACA GTG | 9092 |
| TAC GAC CGT CTG AAA GAA ACA ACT GCA GGC TAC ATC ACT ATG CAC AGG | 9140 |
| CCG GGA CCG CAC GCT TAT ACA TCC TAC CTG GAA GAA TCA TCA GGG AAA | 9188 |
| GTT TAC GCA AAG CCG CCA TCT GGG AAG AAC ATT ACG TAT GAG TGC AAG | 9236 |
| TGC GGC GAC TAC AAG ACC GGA ACC GTT TCG ACC CGC ACC GAA ATC ACT | 9284 |
| GGT TGC ACC GCC ATC AAG CAG TGC GTC GCC TAT AAG AGC GAC CAA ACG | 9332 |
| AAG TGG GTC TTC AAC TCA CCG GAC TTG ATC AGA CAT GAC GAC CAC ACG | 9380 |
| GCC CAA GGG AAA TTG CAT TTG CCT TTC AAG TTG ATC CCG AGT ACC TGC | 9428 |
| ATG GTC CCT GTT GCC CAC GCG CCG AAT GTA ATA CAT GGC TTT AAA CAC | 9476 |
| ATC AGC CTC CAA TTA GAT ACA GAC CAC TTG ACA TTG CTC ACC ACC AGG | 9524 |
| AGA CTA GGG GCA AAC CCG GAA CCA ACC ACT GAA TGG ATC GTC GGA AAG | 9572 |
| ACG TCA AGA AAC TTC ACC GTC GAC CGA GAT GGC CTG GAA TAC ATA TGG | 9620 |
| GGA AAT CAT GAG CCA GTG AGG GTC TAT GCC CAA GAG TCA GCA CCA GGA | 9668 |
| GAC CCT CAC GGA TGG CCA CAC GAA ATA GTA CAG CAT TAC TAC CAT CGC | 9716 |
| CAT CCT GTG TAC ACC ATC TTA GCC GTC GCA TCA GCT ACC GTG GCG ATG | 9764 |
| ATG ATT GGC GTA ACC GTT GCA GTG TTA TGT GCC TGT AAA GCG CGC CGT | 9812 |
| GAG TGC CTG ACG CCA TAC GCC CTG GCC CCA AAC GCC GTA ATC CCA ACT | 9860 |
| TCG CTG GCA CTC TTG TGC TGC GTT AGG TCG GCC AAT GCT GAA ACG TTC | 9908 |
| ACC GAG ACC ATG AGT TAC TTG TGG TCG AAC AGT CAG CCG TTC TTC TGG | 9956 |
| GTC CAG TTG TGC ATA CCT TTG GCC GCT TTC ATC GTT CTA ATG CGC TGC | 10004 |
| TGC TCC TGC TGC CTG CCT TTT TTA GTG GTT GCC GGC GCC TAC CTG GCG | 10052 |
| AAG GTA GAC GCC TAC GAA CAT GCG ACC ACT GTT CCA AAT GTG CCA CAG | 10100 |
| ATA CCG TAT AAG GCA CTT GTT GAA AGG GCA GGG TAT GCC CCG CTC AAT | 10148 |
| TTG GAG ATC ACT GTC ATG TCC TCG GAG GTT TTG CCT TCC ACC AAC CAA | 10196 |
| GAG TAC ATT ACC TGC AAA TTC ACC ACT GTG GTC CCC TCC CCA AAA ATC | 10244 |
| AAA TGC TGC GGC TCC TTG GAA TGT CAG CCG GCC GCT CAT GCA GAC TAT | 10292 |
| ACC TGC AAG GTC TTC GGA GGG GTC TAC CCC TTT ATG TGG GGA GGA GCG | 10340 |
| CAA TGT TTT TGC GAC AGT GAG AAC AGC CAG ATG AGT GAG GCG TAC GTC | 10388 |
| GAA CTG TCA GCA GAT TGC GCG TCT GAC CAC GCG CAG GCG ATT AAG GTG | 10436 |
| CAC ACT GCC GCG ATG AAA GTA GGA CTG CGT ATA GTG TAC GGG AAC ACT | 10484 |
| ACC AGT TTC CTA GAT GTG TAC GTG AAC GGA GTC ACA CCA GGA ACG TCT | 10532 |
| AAA GAC TTG AAA GTC ATA GCT GGA CCA ATT TCA GCA TCG TTT ACG CCA | 10580 |
| TTC GAT CAT AAG GTC GTT ATC CAT CGC GGC CTG GTG TAC AAC TAT GAC | 10628 |
| TTC CCG GAA TAT GGA GCG ATG AAA CCA GGA GCG TTT GGA GAC ATT CAA | 10676 |
| GCT ACC TCC TTG ACT AGC AAG GAT CTC ATC GCC AGC ACA GAC ATT AGG | 10724 |
| CTA CTC AAG CCT TCC GCC AAG AAC GTG CAT GTC CCG TAC ACG CAG GCC | 10772 |
| GCA TCA GGA TTT GAG ATG TGG AAA AAC AAC TCA GGC CGC CCA CTG CAG | 10820 |
| GAA ACC GCA CCT TTC GGG TGT AAG ATT GCA GTA AAT CCG CTC CGA GCG | 10868 |
| GTG GAC TGT TCA TAC GGG AAC ATT CCC ATT TCT ATT GAC ATC CCG AAC | 10916 |

```
GCT GCC TTT ATC AGG ACA TCA GAT GCA CCA CTG GTC TCA ACA GTC AAA      10964

TGT GAA GTC AGT GAG TGC ACT TAT TCA GCA GAC TTC GGC GGG ATG GCC      11012

ACC CTG CAG TAT GTA TCC GAC CGC GAA GGT CAA TGC CCC GTA CAT TCG      11060

CAT TCG AGC ACA GCA ACT CTC CAA GAG TCG ACA GTA CAT GTC CTG GAG      11108

AAA GGA GCG GTG ACA GTA CAC TTT AGC ACC GCG AGT CCA CAG GCG AAC      11156

TTT ATC GTA TCG CTG TGT GGG AAG AAG ACA ACA TGC AAT GCA GAA TGT      11204

AAA CCA CCA GCT GAC CAT ATC GTG AGC ACC CCG CAC AAA AAT GAC CAA      11252

GAA TTT CAA GCC GCC ATC TCA AAA ACA TCA TGG AGT TGG CTG TTT GCC      11300

CTT TTC GGC GGC GCC TCG TCG CTA TTA ATT ATA GGA CTT ATG ATT TTT      11348

GCT TGC AGC ATG ATG CTG ACT AGC ACA CGA AGA TGACCGCTAC GCCCCAATGA    11401

TCCGACCAGC AAAACTCGAT GTACTTCCGA GGAACTGATG TGCATAATGC ATCAGGCTGG    11461

TACATTAGAT CCCCGCTTAC CGCGGGCAAT ATAGCAACAC TAAAAACTCG ATGTACTTCC    11521

GAGGAAGCGC AGTGCATAAT GCTGCGCAGT GTTGCCACAT AACCACTATA TTAACCATTT    11581

ATCTAGCGGA CGCCAAAAAC TCAATGTATT TCTGAGGAAG CGTGGTGCAT AATGCCACGC    11641

AGCGTCTGCA TAACTTTTAT TATTTCTTTT ATTAATCAAC AAAATTTTGT TTTTAACATT    11701

TC                                                                   11703
```

(2) INFORMATION FOR SEQ ID NO:9:

(i) SEQUENCE CHARACTERISTICS:
        (A) LENGTH: 2512 amino acids
        (B) TYPE: amino acid
        (D) TOPOLOGY: linear (ii) MOLECULE TYPE: protein (xi) SEQUENCE DESCRIPTION: SEQ ID NO:9:

```
Met Glu Lys Pro Val Val Asn Val Asp Val Asp Pro Gln Ser Pro Phe
 1               5                  10                  15

Val Val Gln Leu Gln Lys Ser Phe Pro Gln Phe Glu Val Val Ala Gln
            20                  25                  30

Gln Val Thr Pro Asn Asp His Ala Asn Ala Arg Ala Phe Ser His Leu
        35                  40                  45

Ala Ser Lys Leu Ile Glu Leu Glu Val Pro Thr Thr Ala Thr Ile Leu
    50                  55                  60

Asp Ile Gly Ser Ala Pro Ala Arg Arg Met Phe Ser Glu His Gln Tyr
65                  70                  75                  80

His Cys Val Cys Pro Met Arg Ser Pro Glu Asp Pro Asp Arg Met Met
                85                  90                  95

Lys Tyr Ala Ser Lys Leu Ala Glu Lys Ala Cys Lys Ile Thr Asn Lys
            100                 105                 110

Asn Leu His Glu Lys Ile Lys Asp Leu Arg Thr Val Leu Asp Thr Pro
        115                 120                 125

Asp Ala Glu Thr Pro Ser Leu Cys Phe His Asn Asp Val Thr Cys Asn
    130                 135                 140

Met Arg Ala Glu Tyr Ser Val Met Gln Asp Val Tyr Ile Asn Ala Pro
145                 150                 155                 160

Gly Thr Ile Tyr His Gln Ala Met Lys Gly Val Arg Thr Leu Tyr Trp
                165                 170                 175

Ile Gly Phe Asp Thr Thr Gln Phe Met Phe Ser Ala Met Ala Gly Ser
            180                 185                 190
```

-continued

```
Tyr Pro Ala Tyr Asn Thr Asn Trp Ala Asp Glu Lys Val Leu Glu Ala
        195                 200                 205

Arg Asn Ile Gly Leu Cys Ser Thr Lys Leu Ser Glu Gly Arg Thr Gly
        210                 215                 220

Lys Leu Ser Ile Met Arg Lys Lys Glu Leu Lys Pro Gly Ser Arg Val
225                 230                 235                 240

Tyr Phe Ser Val Gly Ser Thr Leu Tyr Pro Glu His Arg Ala Ser Leu
                    245                 250                 255

Gln Ser Trp His Leu Pro Ser Val Phe His Leu Asn Gly Lys Gln Ser
                260                 265                 270

Tyr Thr Cys Arg Cys Asp Thr Val Ser Cys Glu Gly Tyr Val Val
            275                 280                 285

Lys Lys Ile Thr Ile Ser Pro Gly Ile Thr Gly Glu Thr Val Gly Tyr
        290                 295                 300

Ala Val Thr His Asn Ser Glu Gly Phe Leu Leu Cys Lys Val Thr Asp
305                 310                 315                 320

Thr Val Lys Gly Glu Arg Val Ser Phe Pro Val Cys Thr Tyr Ile Pro
                    325                 330                 335

Ala Thr Ile Cys Asp Gln Met Thr Gly Ile Met Ala Thr Asp Ile Ser
                340                 345                 350

Pro Asp Asp Ala Gln Lys Leu Leu Val Gly Leu Asn Gln Arg Ile Val
            355                 360                 365

Ile Asn Gly Arg Thr Asn Arg Asn Thr Asn Thr Met Gln Asn Tyr Leu
        370                 375                 380

Leu Pro Ile Ile Ala Gln Gly Phe Ser Lys Trp Ala Lys Glu Arg Lys
385                 390                 395                 400

Asp Asp Leu Asp Asn Glu Lys Met Leu Gly Thr Arg Glu Arg Lys Leu
                    405                 410                 415

Thr Tyr Gly Cys Leu Trp Ala Phe Arg Thr Lys Lys Val His Ser Phe
                420                 425                 430

Tyr Arg Pro Pro Gly Thr Gln Thr Ile Val Lys Val Pro Ala Ser Phe
            435                 440                 445

Ser Ala Phe Pro Met Ser Ser Val Trp Thr Thr Ser Leu Pro Met Ser
        450                 455                 460

Leu Arg Gln Lys Leu Lys Leu Ala Leu Gln Pro Lys Lys Glu Glu Lys
465                 470                 475                 480

Leu Leu Gln Val Ser Glu Glu Leu Val Met Glu Ala Lys Ala Ala Phe
                    485                 490                 495

Glu Asp Ala Gln Glu Glu Ala Arg Ala Glu Lys Leu Arg Glu Ala Leu
                500                 505                 510

Pro Pro Leu Val Ala Asp Lys Gly Ile Glu Ala Ala Glu Val Val
            515                 520                 525

Cys Glu Val Glu Gly Leu Gln Ala Asp Ile Gly Ala Ala Leu Val Glu
530                 535                 540

Thr Pro Arg Gly His Val Arg Ile Ile Pro Gln Ala Asn Asp Arg Met
545                 550                 555                 560

Ile Gly Gln Tyr Ile Val Val Ser Pro Asn Ser Val Leu Lys Asn Ala
                    565                 570                 575

Lys Leu Ala Pro Ala His Pro Leu Ala Asp Gln Val Lys Ile Ile Thr
                580                 585                 590

His Ser Gly Arg Ser Arg Tyr Ala Val Glu Pro Tyr Asp Ala Lys
            595                 600                 605

Val Leu Met Pro Ala Gly Gly Ala Val Pro Trp Pro Glu Phe Leu Ala
610                 615                 620
```

-continued

Leu Ser Glu Ser Ala Thr Leu Val Tyr Asn Glu Arg Glu Phe Val Asn
625                 630                 635                 640

Arg Lys Leu Tyr His Ile Ala Met His Gly Pro Ala Lys Asn Thr Glu
            645                 650                 655

Glu Glu Gln Tyr Lys Val Thr Lys Ala Glu Leu Ala Glu Thr Glu Tyr
        660                 665                 670

Val Phe Asp Val Asp Lys Lys Arg Cys Val Lys Lys Glu Glu Ala Ser
    675                 680                 685

Gly Leu Val Leu Ser Gly Glu Leu Thr Asn Pro Pro Tyr His Glu Leu
690                 695                 700

Ala Leu Glu Gly Leu Lys Thr Arg Pro Ala Val Pro Tyr Lys Val Glu
705                 710                 715                 720

Thr Ile Gly Val Ile Gly Thr Pro Gly Ser Gly Lys Ser Ala Ile Ile
                725                 730                 735

Lys Ser Thr Val Thr Ala Arg Asp Leu Val Thr Ser Gly Lys Lys Glu
            740                 745                 750

Asn Cys Arg Glu Ile Glu Ala Asp Val Leu Arg Leu Arg Gly Met Gln
        755                 760                 765

Ile Thr Ser Lys Thr Val Asp Ser Val Met Leu Asn Gly Cys His Lys
770                 775                 780

Ala Val Glu Val Leu Tyr Val Asp Glu Ala Phe Ala Cys His Ala Gly
785                 790                 795                 800

Ala Leu Leu Ala Leu Ile Ala Ile Val Arg Pro Arg Lys Lys Val Val
                805                 810                 815

Leu Cys Gly Asp Pro Met Gln Cys Gly Phe Phe Asn Met Met Gln Leu
            820                 825                 830

Lys Val His Phe Asn His Pro Glu Lys Asp Ile Cys Thr Lys Thr Phe
        835                 840                 845

Tyr Lys Tyr Ile Ser Arg Arg Cys Thr Gln Pro Val Thr Ala Ile Val
    850                 855                 860

Ser Thr Leu His Tyr Asp Gly Lys Met Lys Thr Thr Asn Pro Cys Lys
865                 870                 875                 880

Lys Asn Ile Glu Ile Asp Ile Thr Gly Ala Thr Lys Pro Lys Pro Gly
                885                 890                 895

Asp Ile Ile Leu Thr Cys Phe Arg Gly Trp Val Lys Gln Leu Gln Ile
            900                 905                 910

Asp Tyr Pro Gly His Glu Val Met Thr Ala Ala Ser Gln Gly Leu
        915                 920                 925

Thr Arg Lys Gly Val Tyr Ala Val Arg Gln Lys Val Asn Glu Asn Pro
930                 935                 940

Leu Tyr Ala Ile Thr Ser Glu His Val Asn Val Leu Leu Thr Arg Thr
945                 950                 955                 960

Glu Asp Arg Leu Val Trp Lys Thr Leu Gln Gly Asp Pro Trp Ile Lys
                965                 970                 975

Gln Leu Thr Asn Ile Pro Lys Gly Asn Phe Gln Ala Thr Ile Glu Asp
            980                 985                 990

Trp Glu Ala Glu His Lys Gly Ile Ile Ala Ala Ile Asn Ser Pro Thr
        995                 1000                1005

Pro Arg Ala Asn Pro Phe Ser Cys Lys Thr Asn Val Cys Trp Ala Lys
    1010                1015                1020

Ala Leu Glu Pro Ile Leu Ala Thr Ala Gly Ile Val Leu Thr Gly Cys
1025                1030                1035                1040

Gln Trp Ser Glu Leu Phe Pro Gln Phe Ala Asp Asp Lys Pro His Ser

-continued

```
                    1045              1050              1055
Ala  Ile  Tyr  Ala  Leu  Asp  Val  Ile  Cys  Ile  Lys  Phe  Phe  Gly  Met  Asp
                         1060              1065              1070

Leu  Thr  Ser  Gly  Leu  Phe  Ser  Lys  Gln  Ser  Ile  Pro  Leu  Thr  Tyr  His
          1075              1080              1085

Pro  Ala  Asp  Ser  Ala  Arg  Pro  Val  Ala  His  Trp  Asp  Asn  Ser  Pro  Gly
          1090              1095              1100

Thr  Arg  Lys  Tyr  Gly  Tyr  Asp  His  Ala  Ile  Ala  Ala  Glu  Leu  Ser  Arg
1105                1110              1115                        1120

Arg  Phe  Pro  Val  Phe  Gln  Leu  Ala  Gly  Lys  Thr  Gln  Leu  Asp  Leu
               1125              1130              1135

Gln  Thr  Gly  Arg  Thr  Arg  Val  Ile  Ser  Ala  Gln  His  Asn  Leu  Val  Pro
               1140              1145              1150

Val  Asn  Arg  Asn  Leu  Pro  His  Ala  Leu  Val  Pro  Glu  Tyr  Lys  Glu  Lys
          1155              1160              1165

Gln  Pro  Gly  Pro  Val  Glu  Lys  Phe  Leu  Asn  Gln  Phe  Lys  His  His  Ser
          1170              1175              1180

Val  Leu  Val  Val  Ser  Glu  Glu  Lys  Ile  Glu  Ala  Pro  Arg  Lys  Arg  Ile
1185                1190              1195                        1200

Glu  Trp  Ile  Ala  Pro  Ile  Gly  Ile  Ala  Gly  Ala  Asp  Lys  Asn  Tyr  Asn
                    1205              1210              1215

Leu  Ala  Phe  Gly  Phe  Pro  Pro  Gln  Ala  Arg  Tyr  Asp  Leu  Val  Phe  Ile
                    1220              1225              1230

Asn  Ile  Gly  Thr  Lys  Tyr  Arg  Asn  His  His  Phe  Gln  Gln  Cys  Glu  Asp
                    1235              1240              1245

His  Ala  Ala  Thr  Leu  Lys  Thr  Leu  Ser  Arg  Ser  Ala  Leu  Asn  Cys  Leu
                    1250              1255              1260

Asn  Pro  Gly  Gly  Thr  Leu  Val  Val  Lys  Ser  Tyr  Gly  Tyr  Ala  Asp  Arg
1265                1270              1275                        1280

Asn  Ser  Glu  Asp  Val  Val  Thr  Ala  Leu  Ala  Arg  Lys  Phe  Val  Arg  Val
                    1285              1290              1295

Ser  Ala  Ala  Arg  Pro  Asp  Cys  Val  Ser  Ser  Asn  Thr  Glu  Met  Tyr  Leu
                    1300              1305              1310

Ile  Phe  Arg  Gln  Leu  Asp  Asn  Ser  Arg  Thr  Arg  Gln  Phe  Thr  Pro  His
                    1315              1320              1325

His  Leu  Asn  Cys  Val  Ile  Ser  Ser  Val  Tyr  Glu  Gly  Thr  Arg  Asp  Gly
                    1330              1335              1340

Val  Gly  Ala  Ala  Pro  Ser  Tyr  Arg  Thr  Lys  Arg  Glu  Asn  Ile  Ala  Asp
1345                1350              1355                        1360

Cys  Gln  Glu  Glu  Ala  Val  Val  Asn  Ala  Ala  Asn  Pro  Leu  Gly  Arg  Pro
                    1365              1370              1375

Gly  Glu  Gly  Val  Cys  Arg  Ala  Ile  Tyr  Lys  Arg  Trp  Pro  Thr  Ser  Phe
                    1380              1385              1390

Thr  Asp  Ser  Ala  Thr  Glu  Thr  Gly  Thr  Ala  Arg  Met  Thr  Val  Cys  Leu
               1395              1400              1405

Gly  Lys  Lys  Val  Ile  His  Ala  Val  Gly  Pro  Asp  Phe  Arg  Lys  His  Pro
          1410              1415              1420

Glu  Ala  Glu  Ala  Leu  Lys  Leu  Leu  Gln  Asn  Ala  Tyr  His  Ala  Val  Ala
1425                1430              1435                        1440

Asp  Leu  Val  Asn  Glu  His  Asn  Ile  Lys  Ser  Val  Ala  Ile  Pro  Leu  Leu
                    1445              1450              1455

Ser  Thr  Gly  Ile  Tyr  Ala  Ala  Gly  Lys  Asp  Arg  Leu  Glu  Val  Ser  Leu
                    1460              1465              1470
```

-continued

```
Asn Cys Leu Thr Thr Ala Leu Asp Arg Thr Asp Ala Asp Val Thr Ile
            1475                1480                1485

Tyr Cys Leu Asp Lys Lys Trp Lys Glu Arg Ile Asp Ala Ala Leu Gln
        1490                1495                1500

Leu Lys Glu Ser Val Thr Glu Leu Lys Asp Glu Asp Met Glu Ile Asp
1505                1510                1515                1520

Asp Glu Leu Val Trp Ile His Pro Asp Ser Cys Leu Lys Gly Arg Lys
                1525                1530                1535

Gly Phe Ser Thr Thr Lys Gly Lys Leu Tyr Ser Tyr Phe Glu Gly Thr
            1540                1545                1550

Lys Phe His Gln Ala Ala Lys Asp Met Ala Glu Ile Lys Val Leu Phe
        1555                1560                1565

Pro Asn Asp Gln Glu Ser Asn Glu Gln Leu Cys Ala Tyr Ile Leu Gly
    1570                1575                1580

Glu Thr Met Glu Ala Ile Arg Glu Lys Cys Pro Val Asp His Asn Pro
1585                1590                1595                1600

Ser Ser Ser Pro Pro Lys Thr Leu Pro Cys Leu Cys Met Tyr Ala Met
                1605                1610                1615

Thr Pro Glu Arg Val His Arg Leu Arg Ser Asn Asn Val Lys Glu Val
            1620                1625                1630

Thr Val Cys Ser Ser Thr Pro Leu Pro Lys His Lys Ile Lys Asn Val
        1635                1640                1645

Gln Lys Val Gln Cys Thr Lys Val Val Leu Phe Asn Pro His Thr Pro
    1650                1655                1660

Ala Phe Val Pro Ala Arg Lys Tyr Ile Glu Val Pro Glu Gln Pro Thr
1665                1670                1675                1680

Ala Pro Pro Ala Gln Ala Glu Glu Ala Pro Glu Val Val Ala Thr Pro
                1685                1690                1695

Ser Pro Ser Thr Ala Asp Asn Thr Ser Leu Asp Val Thr Asp Ile Ser
            1700                1705                1710

Leu Asp Met Asp Asp Ser Ser Glu Gly Ser Leu Phe Ser Ser Phe Ser
        1715                1720                1725

Gly Ser Asp Asn Ser Ile Thr Ser Met Asp Ser Trp Ser Ser Gly Pro
    1730                1735                1740

Ser Ser Leu Glu Ile Val Asp Arg Arg Gln Val Val Val Ala Asp Val
1745                1750                1755                1760

His Ala Val Gln Glu Pro Ala Pro Ile Pro Pro Arg Leu Lys Lys
                1765                1770                1775

Met Ala Arg Leu Ala Ala Ala Arg Lys Glu Pro Thr Pro Pro Ala Ser
            1780                1785                1790

Asn Ser Ser Glu Ser Leu His Leu Ser Phe Gly Gly Val Ser Met Ser
        1795                1800                1805

Leu Gly Ser Ile Phe Asp Gly Glu Thr Ala Arg Gln Ala Ala Val Gln
    1810                1815                1820

Pro Leu Ala Thr Gly Pro Thr Asp Val Pro Met Ser Phe Gly Ser Phe
1825                1830                1835                1840

Ser Asp Gly Glu Ile Asp Glu Leu Ser Arg Arg Val Thr Glu Ser Glu
                1845                1850                1855

Pro Val Leu Phe Gly Ser Phe Pro Gly Glu Val Asn Ser Ile Ile
            1860                1865                1870

Ser Ser Arg Ser Ala Val Ser Phe Pro Leu Arg Lys Gln Arg Arg
        1875                1880                1885

Arg Arg Ser Arg Arg Thr Glu Tyr Leu Thr Gly Val Gly Gly Tyr Ile
    1890                1895                1900
```

```
Phe Ser Thr Asp Thr Gly Pro Gly His Leu Gln Lys Lys Ser Val Leu
1905                1910                1915                1920

Gln Asn Gln Leu Thr Glu Pro Thr Leu Glu Arg Asn Val Leu Glu Arg
            1925                1930                1935

Ile His Ala Pro Val Leu Asp Thr Ser Lys Glu Gln Leu Lys Leu
            1940                1945                1950

Arg Tyr Gln Met Met Pro Thr Glu Ala Asn Lys Ser Arg Tyr Gln Ser
            1955                1960                1965

Arg Lys Val Glu Asn Gln Lys Ala Ile Thr Thr Glu Arg Leu Leu Ser
    1970                1975                1980

Gly Leu Arg Leu Tyr Asn Ser Ala Thr Asp Gln Pro Glu Cys Tyr Lys
1985                1990                1995                2000

Ile Thr Tyr Pro Lys Pro Leu Tyr Ser Ser Val Pro Ala Asn Tyr
            2005                2010                2015

Ser Asp Pro Gln Phe Ala Val Ala Val Cys Asn Asn Tyr Leu His Glu
            2020                2025                2030

Asn Tyr Pro Thr Val Ala Ser Tyr Gln Ile Thr Asp Glu Tyr Asp Ala
            2035                2040                2045

Tyr Leu Asp Met Val Asp Gly Thr Val Ala Cys Leu Asp Thr Ala Thr
            2050                2055                2060

Phe Cys Pro Ala Lys Leu Arg Ser Tyr Pro Lys Lys His Glu Tyr Arg
2065                2070                2075                2080

Ala Pro Asn Ile Arg Ser Ala Val Pro Ser Ala Met Gln Asn Thr Leu
            2085                2090                2095

Gln Asn Val Leu Ile Ala Ala Thr Lys Arg Asn Cys Asn Val Thr Gln
            2100                2105                2110

Met Arg Glu Leu Pro Thr Leu Asp Ser Ala Thr Phe Asn Val Glu Cys
            2115                2120                2125

Phe Arg Lys Tyr Ala Cys Asn Asp Glu Tyr Trp Glu Glu Phe Ala Arg
            2130                2135                2140

Lys Pro Ile Arg Ile Thr Thr Glu Phe Val Thr Ala Tyr Val Ala Arg
2145                2150                2155                2160

Leu Lys Gly Pro Lys Ala Ala Ala Leu Phe Ala Lys Thr Tyr Asn Leu
            2165                2170                2175

Val Pro Leu Gln Glu Val Pro Met Asp Arg Phe Val Met Asp Met Lys
            2180                2185                2190

Arg Asp Val Lys Val Thr Pro Gly Thr Lys His Thr Glu Glu Arg Pro
            2195                2200                2205

Lys Val Gln Val Ile Gln Ala Ala Glu Pro Leu Ala Thr Ala Tyr Leu
    2210                2215                2220

Cys Gly Ile His Arg Glu Leu Val Arg Arg Leu Thr Ala Val Leu Leu
2225                2230                2235                2240

Pro Asn Ile His Thr Leu Phe Asp Met Ser Ala Glu Asp Phe Asp Ala
            2245                2250                2255

Ile Ile Ala Glu His Phe Lys Gln Gly Asp Pro Val Leu Glu Thr Asp
            2260                2265                2270

Ile Ala Ser Phe Asp Lys Ser Gln Asp Asp Ala Met Ala Leu Thr Gly
            2275                2280                2285

Leu Met Ile Leu Glu Asp Leu Gly Val Asp Gln Pro Leu Leu Asp Leu
    2290                2295                2300

Ile Glu Cys Ala Phe Gly Glu Ile Ser Ser Thr His Leu Pro Thr Gly
2305                2310                2315                2320

Thr Arg Phe Lys Phe Gly Ala Met Met Lys Ser Gly Met Phe Leu Thr
```

```
                        2325                2330                2335
Leu Phe Val Asn Thr Val Leu Asn Val Val Ile Ala Ser Arg Val Leu
                2340                2345                2350

Glu Glu Arg Leu Lys Thr Ser Arg Cys Ala Ala Phe Ile Gly Asp Asp
                2355                2360                2365

Asn Ile Ile His Gly Val Val Ser Asp Lys Glu Met Ala Glu Arg Cys
                2370                2375                2380

Ala Thr Trp Leu Asn Met Glu Val Lys Ile Ile Asp Ala Val Ile Gly
2385                2390                2395                2400

Glu Arg Pro Pro Tyr Phe Cys Gly Gly Phe Ile Leu Gln Asp Ser Val
                2405                2410                2415

Thr Ser Thr Ala Cys Arg Val Ala Asp Pro Leu Lys Arg Leu Phe Lys
                2420                2425                2430

Leu Gly Lys Pro Leu Pro Ala Asp Asp Glu Gln Asp Glu Asp Arg Arg
                2435                2440                2445

Arg Ala Leu Leu Asp Glu Thr Lys Ala Trp Phe Arg Val Gly Ile Thr
                2450                2455                2460

Gly Thr Leu Ala Val Ala Val Thr Thr Arg Tyr Glu Val Asp Asn Ile
2465                2470                2475                2480

Thr Pro Val Leu Leu Ala Leu Arg Thr Phe Ala Gln Ser Lys Arg Ala
                2485                2490                2495

Phe Gln Ala Ile Arg Gly Glu Ile Lys His Leu Tyr Gly Gly Pro Lys
                2500                2505                2510

(2) INFORMATION FOR SEQ ID NO:10:

(i) SEQUENCE CHARACTERISTICS:
        (A) LENGTH: 1245 amino acids
        (B) TYPE: amino acid
        (D) TOPOLOGY: linear (ii) MOLECULE TYPE: protein (xi) SEQUENCE DESCRIPTION: SEQ ID NO:10:

Met Asn Arg Gly Phe Phe Asn Met Leu Gly Arg Arg Pro Phe Pro Ala
1               5                   10                  15

Pro Thr Ala Met Trp Arg Pro Arg Arg Arg Gln Ala Ala Pro Met
                20                  25                  30

Pro Ala Arg Asn Gly Leu Ala Ser Gln Ile Gln Gln Leu Thr Thr Ala
                35                  40                  45

Val Ser Ala Leu Val Ile Gly Gln Ala Thr Arg Pro Gln Pro Pro Arg
            50                  55                  60

Pro Arg Pro Pro Pro Arg Gln Lys Lys Gln Ala Pro Lys Gln Pro Pro
65                  70                  75                  80

Lys Pro Lys Lys Pro Lys Thr Gln Glu Lys Lys Lys Gln Pro Ala
                85                  90                  95

Lys Pro Lys Pro Gly Lys Arg Gln Arg Met Ala Leu Lys Leu Glu Ala
                100                 105                 110

Asp Arg Leu Phe Asp Val Lys Asn Glu Asp Gly Asp Val Ile Gly His
                115                 120                 125

Ala Leu Ala Met Glu Gly Lys Val Met Lys Pro Leu His Val Lys Gly
                130                 135                 140

Thr Ile Asp His Pro Val Leu Ser Lys Leu Lys Phe Thr Lys Ser Ser
145                 150                 155                 160

Ala Tyr Asp Met Glu Phe Ala Gln Leu Pro Val Asn Met Arg Ser Glu
                165                 170                 175
```

-continued

```
Ala Phe Thr Tyr Thr Ser Glu His Pro Glu Gly Phe Tyr Asn Trp His
            180                 185                 190

His Gly Ala Val Gln Tyr Ser Gly Arg Phe Thr Ile Pro Arg Gly
        195                 200                 205

Val Gly Gly Arg Gly Asp Ser Gly Arg Pro Ile Met Asp Asn Ser Gly
    210                 215                 220

Arg Val Ala Ile Val Leu Gly Gly Ala Asp Glu Gly Thr Arg Thr
225                 230                 235                 240

Ala Leu Ser Val Val Thr Trp Asn Ser Lys Gly Lys Thr Ile Lys Thr
                245                 250                 255

Thr Pro Glu Gly Thr Glu Trp Ser Ala Ala Pro Leu Val Thr Ala
            260                 265                 270

Met Cys Leu Leu Gly Asn Val Ser Phe Pro Cys Asp Arg Pro Pro Thr
        275                 280                 285

Cys Tyr Thr Arg Glu Pro Ser Arg Ala Leu Asp Ile Leu Glu Glu Asn
    290                 295                 300

Val Asn His Glu Ala Tyr Asp Thr Leu Leu Asn Ala Ile Leu Arg Cys
305                 310                 315                 320

Gly Ser Ser Gly Arg Ser Lys Arg Ser Val Thr Asp Asp Phe Thr Leu
                325                 330                 335

Thr Ser Pro Tyr Leu Gly Thr Cys Ser Tyr Cys His His Thr Glu Pro
            340                 345                 350

Cys Phe Ser Pro Val Lys Ile Glu Gln Val Trp Asp Glu Ala Asp Asp
        355                 360                 365

Asn Thr Ile Arg Ile Gln Thr Ser Ala Gln Phe Gly Tyr Asp Gln Ser
    370                 375                 380

Gly Ala Ala Ser Ala Asn Lys Tyr Arg Tyr Met Ser Leu Glu Gln Asp
385                 390                 395                 400

His Thr Val Lys Glu Gly Thr Met Asp Asp Ile Lys Ile Ser Thr Ser
                405                 410                 415

Gly Pro Cys Arg Arg Leu Ser Tyr Lys Gly Tyr Phe Leu Leu Ala Lys
            420                 425                 430

Cys Pro Pro Gly Asp Ser Val Thr Val Ser Ile Val Ser Ser Asn Ser
        435                 440                 445

Ala Thr Ser Cys Thr Leu Ala Arg Lys Ile Lys Pro Lys Phe Val Gly
    450                 455                 460

Arg Glu Lys Tyr Asp Leu Pro Pro Val His Gly Lys Lys Ile Pro Cys
465                 470                 475                 480

Thr Val Tyr Asp Arg Leu Lys Glu Thr Thr Ala Gly Tyr Ile Thr Met
                485                 490                 495

His Arg Pro Gly Pro His Ala Tyr Thr Ser Tyr Leu Glu Glu Ser Ser
            500                 505                 510

Gly Lys Val Tyr Ala Lys Pro Pro Ser Gly Lys Asn Ile Thr Tyr Glu
        515                 520                 525

Cys Lys Cys Gly Asp Tyr Lys Thr Gly Thr Val Ser Thr Arg Thr Glu
    530                 535                 540

Ile Thr Gly Cys Thr Ala Ile Lys Gln Cys Val Ala Tyr Lys Ser Asp
545                 550                 555                 560

Gln Thr Lys Trp Val Phe Asn Ser Pro Asp Leu Ile Arg His Asp Asp
                565                 570                 575

His Thr Ala Gln Gly Lys Leu His Leu Pro Phe Lys Leu Ile Pro Ser
            580                 585                 590

Thr Cys Met Val Pro Val Ala His Ala Pro Asn Val Ile His Gly Phe
        595                 600                 605
```

-continued

Lys His Ile Ser Leu Gln Leu Asp Thr Asp His Leu Thr Leu Thr
       610                 615                 620

Thr Arg Arg Leu Gly Ala Asn Pro Glu Pro Thr Thr Glu Trp Ile Val
625                 630                 635                 640

Gly Lys Thr Val Arg Asn Phe Thr Val Asp Arg Asp Gly Leu Glu Tyr
                    645                 650                 655

Ile Trp Gly Asn His Glu Pro Val Arg Val Tyr Ala Gln Glu Ser Ala
                660                 665                 670

Pro Gly Asp Pro His Gly Trp Pro His Glu Ile Val Gln His Tyr Tyr
            675                 680                 685

His Arg His Pro Val Tyr Thr Ile Leu Ala Val Ala Ser Ala Thr Val
        690                 695                 700

Ala Met Met Ile Gly Val Thr Val Ala Val Leu Cys Ala Cys Lys Ala
705                 710                 715                 720

Arg Arg Glu Cys Leu Thr Pro Tyr Ala Leu Ala Pro Asn Ala Val Ile
                    725                 730                 735

Pro Thr Ser Leu Ala Leu Leu Cys Cys Val Arg Ser Ala Asn Ala Glu
                740                 745                 750

Thr Phe Thr Glu Thr Met Ser Tyr Leu Trp Ser Asn Ser Gln Pro Phe
            755                 760                 765

Phe Trp Val Gln Leu Cys Ile Pro Leu Ala Ala Phe Ile Val Leu Met
        770                 775                 780

Arg Cys Cys Ser Cys Cys Leu Pro Phe Leu Val Val Ala Gly Ala Tyr
785                 790                 795                 800

Leu Ala Lys Val Asp Ala Tyr Glu His Ala Thr Thr Val Pro Asn Val
                    805                 810                 815

Pro Gln Ile Pro Tyr Lys Ala Leu Val Glu Arg Ala Gly Tyr Ala Pro
                820                 825                 830

Leu Asn Leu Glu Ile Thr Val Met Ser Ser Glu Val Leu Pro Ser Thr
            835                 840                 845

Asn Gln Glu Tyr Ile Thr Cys Lys Phe Thr Thr Val Val Pro Ser Pro
        850                 855                 860

Lys Ile Lys Cys Cys Gly Ser Leu Glu Cys Gln Pro Ala Ala His Ala
865                 870                 875                 880

Asp Tyr Thr Cys Lys Val Phe Gly Gly Val Tyr Pro Phe Met Trp Gly
                    885                 890                 895

Gly Ala Gln Cys Phe Cys Asp Ser Glu Asn Ser Gln Met Ser Glu Ala
                900                 905                 910

Tyr Val Glu Leu Ser Ala Asp Cys Ala Ser Asp His Ala Gln Ala Ile
            915                 920                 925

Lys Val His Thr Ala Ala Met Lys Val Gly Leu Arg Ile Val Tyr Gly
        930                 935                 940

Asn Thr Thr Ser Phe Leu Asp Val Tyr Val Asn Gly Val Thr Pro Gly
945                 950                 955                 960

Thr Ser Lys Asp Leu Lys Val Ile Ala Gly Pro Ile Ser Ala Ser Phe
                    965                 970                 975

Thr Pro Phe Asp His Lys Val Val Ile His Arg Gly Leu Val Tyr Asn
                980                 985                 990

Tyr Asp Phe Pro Glu Tyr Gly Ala Met Lys Pro Gly Ala Phe Gly Asp
            995                 1000                1005

Ile Gln Ala Thr Ser Leu Thr Ser Lys Asp Leu Ile Ala Ser Thr Asp
        1010                1015                1020

Ile Arg Leu Leu Lys Pro Ser Ala Lys Asn Val His Val Pro Tyr Thr

-continued

```
               1025                1030                1035                1040

Gln Ala Ala Ser Gly Phe Glu Met Trp Lys Asn Asn Ser Gly Arg Pro
                        1045                1050                1055

Leu Gln Glu Thr Ala Pro Phe Gly Cys Lys Ile Ala Val Asn Pro Leu
                    1060                1065                1070

Arg Ala Val Asp Cys Ser Tyr Gly Asn Ile Pro Ile Ser Ile Asp Ile
                1075                1080                1085

Pro Asn Ala Ala Phe Ile Arg Thr Ser Asp Ala Pro Leu Val Ser Thr
            1090                1095                1100

Val Lys Cys Glu Val Ser Glu Cys Thr Tyr Ser Ala Asp Phe Gly Gly
        1105                1110                1115                1120

Met Ala Thr Leu Gln Tyr Val Ser Asp Arg Glu Gly Gln Cys Pro Val
                    1125                1130                1135

His Ser His Ser Ser Thr Ala Thr Leu Gln Glu Ser Thr Val His Val
                        1140                1145                1150

Leu Glu Lys Gly Ala Val Thr Val His Phe Ser Thr Ala Ser Pro Gln
                    1155                1160                1165

Ala Asn Phe Ile Val Ser Leu Cys Gly Lys Lys Thr Thr Cys Asn Ala
                1170                1175                1180

Glu Cys Lys Pro Pro Ala Asp His Ile Val Ser Thr Pro His Lys Asn
        1185                1190                1195                1200

Asp Gln Glu Phe Gln Ala Ala Ile Ser Lys Thr Ser Trp Ser Trp Leu
                        1205                1210                1215

Phe Ala Leu Phe Gly Gly Ala Ser Ser Leu Leu Ile Ile Gly Leu Met
                        1220                1225                1230

Ile Phe Ala Cys Ser Met Met Leu Thr Ser Thr Arg Arg
                    1235                1240                1245

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:11:

CTGCGGCGGA TTCATCTTGC                                                   20

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:12:

CTCCAACTTA AGTG                                                         14
```